United States Patent
Jung

(10) Patent No.: US 9,929,349 B2
(45) Date of Patent: Mar. 27, 2018

(54) ORGANIC LIGHT EMITTING DEVICE AND DISPLAY DEVICE INCLUDING THE SAME

(71) Applicant: SAMSUNG DISPLAY CO., LTD., Yongin, Gyeonggi-Do (KR)

(72) Inventor: Jiyun Jung, Seoul (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 156 days.

(21) Appl. No.: 14/961,262

(22) Filed: Dec. 7, 2015

(65) Prior Publication Data

US 2016/0163990 A1 Jun. 9, 2016

(30) Foreign Application Priority Data

Dec. 8, 2014 (KR) .................. 10-2014-0174813
May 7, 2015 (KR) .................. 10-2015-0063984

(51) Int. Cl.
*C09K 11/02* (2006.01)
*H01L 51/00* (2006.01)
(Continued)

(52) U.S. Cl.
CPC ........ *H01L 51/0055* (2013.01); *C07D 401/10* (2013.01); *C09K 11/025* (2013.01);
(Continued)

(58) Field of Classification Search
CPC ............. H01L 51/0051; H01L 51/0058; H01L 51/0061; H01L 51/0073; H01L 51/0074;
(Continued)

(56) References Cited

U.S. PATENT DOCUMENTS 8,062,769 B2 * 11/2011 Kai ................. C07D 487/04
313/504
2012/0119197 A1 * 5/2012 Nishimura ......... C07D 209/86
257/40
(Continued)

FOREIGN PATENT DOCUMENTS

CN 103570627 A * 2/2014
JP 10-017860 A 1/1998
(Continued)

OTHER PUBLICATIONS

Machine translation of CN 103570627 (no date).*
Machine translation of abstract CN 103570627 (no date).*

*Primary Examiner* — Amanda C Walke
(74) *Attorney, Agent, or Firm* — Lee & Morse, P.C.

(57) ABSTRACT

An organic light emitting device and a display device including the same, the organic light emitting device including a first electrode; a hole transport region on the first electrode; an emission layer on the hole transport region; an electron transport region on the emission layer; and a second electrode on the electron transport region, wherein the electron transport region includes a compound represented by the following Chemical Formula 1:

[Chemical Formula 1]

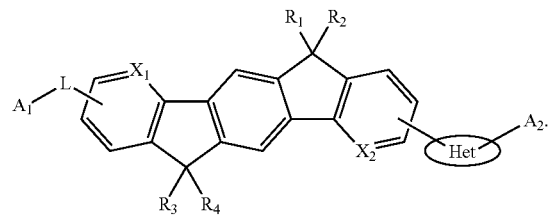

18 Claims, 5 Drawing Sheets

(51) Int. Cl.
*C09K 11/06* (2006.01)
*C07D 401/10* (2006.01)
*H01L 51/50* (2006.01)

(52) U.S. Cl.
CPC .......... *C09K 11/06* (2013.01); *H01L 51/0052* (2013.01); *H01L 51/0054* (2013.01); *H01L 51/0072* (2013.01); *H01L 51/0074* (2013.01); *H01L 51/5056* (2013.01); *H01L 51/0067* (2013.01); *H01L 51/0071* (2013.01); *H01L 51/0085* (2013.01); *H01L 51/5072* (2013.01)

(58) Field of Classification Search
CPC ... H01L 51/5056; C09K 11/025; C09K 11/06; C07D 401/10
USPC ......... 257/40; 428/690; 544/180; 548/304.4, 548/305.1, 361.1
See application file for complete search history.

(56) References Cited

U.S. PATENT DOCUMENTS

| | | | | |
|---|---|---|---|---|
| 2013/0053558 A1* | 2/2013 | Pflumm | ............... | C07D 403/10 544/180 |
| 2014/0166988 A1* | 6/2014 | Yen | .................... | H01L 51/0058 257/40 |
| 2014/0374711 A1* | 12/2014 | Cho | .................... | H01L 51/0072 257/40 |
| 2016/0013420 A1* | 1/2016 | Jung | .................. | H01L 51/0067 257/40 |
| 2016/0028021 A1* | 1/2016 | Zeng | .................. | H01L 51/0067 257/40 |
| 2016/0072073 A1* | 3/2016 | Lee | ...................... | C07D 405/14 257/40 |
| 2016/0133814 A1* | 5/2016 | Ghoshal | .................. | H01L 35/32 136/205 |
| 2016/0380207 A1* | 12/2016 | Yen | .................... | H01L 51/0072 257/40 |

FOREIGN PATENT DOCUMENTS

| | | |
|---|---|---|
| JP | 11-087067 A | 3/1999 |
| JP | 11-345686 A | 12/1999 |
| JP | 2000-182772 A | 6/2000 |
| KR | 10-2007-0004678 A | 1/2007 |
| KR | 10-2008-0104025 A | 11/2008 |
| KR | 10-2013-0113357 A | 10/2013 |
| KR | 10-2014-0021294 A | 2/2014 |
| KR | 10-2014-0029183 A | 3/2014 |
| KR | 10-2014-0079306 A | 6/2014 |
| KR | 10-2014-0087648 A | 7/2014 |

* cited by examiner

ORGANIC LIGHT EMITTING DEVICE AND DISPLAY DEVICE INCLUDING THE SAME

CROSS-REFERENCE TO RELATED APPLICATIONS

Korean Patent Application Nos. 10-2014-0174813, filed on Dec. 8, 2014, and 10-2015-0063984, filed on May 7, 2015, in the Korean Intellectual Property Office, and entitled: "Organic Light Emitting Device and Display Device Including the Same," is incorporated by reference herein in its entirety.

BACKGROUND

1. Field

Embodiments relate to an organic light emitting device and a display device including the same.

2. Description of the Related Art

Flat display devices may be mainly classified as a light emitting type and a light receiving type. The light emitting type includes a flat cathode ray tube, a plasma display panel, an organic light emitting display (OLED), etc. The OLED is a self-luminescent display and has advantages of wide viewing angles, good contrast and rapid response time.

Thus, the OLED is applicable in a display for a mobile device such as a digital camera, a video camera, a camcorder, a personal digital assistant, a smart phone, an ultrathin laptop, a tablet personal computer, a flexible display, etc., or a large-sized electronic products such as an ultra-thin television or a large-sized electric products, and receives much attention.

The OLED embodies color based on the principle that holes and electrons injected from a first electrode and a second electrode are recombined in an emission layer, and excitons obtained by the combination of the injected holes and electrons emit light during the transition thereof from an excited state to a ground state.

SUMMARY

Embodiments are directed to an organic light emitting device and a display device including the same.

The embodiments may be realized by providing an organic light emitting device including a first electrode; a hole transport region on the first electrode; an emission layer on the hole transport region; an electron transport region on the emission layer; and a second electrode on the electron transport region, wherein the electron transport region includes a compound represented by the following Chemical Formula 1:

[Chemical Formula 1]

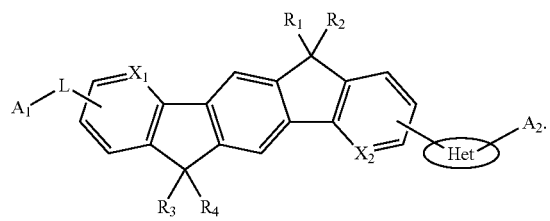

wherein, in the above Chemical Formula 1, $X_1$ and $X_2$ are each independently $CR_5$ or N, $R_1$ to $R_5$ are each independently selected from hydrogen, deuterium, an alkyl group having 1 to 40 carbon atoms, an aryl group having 6 to 40 carbon atoms, a heteroaryl group having 1 to 40 carbon atoms, an aryloxy group having 6 to 40 carbon atoms, an alkyloxy group having 1 to 40 carbon atoms, an arylamino group having 6 to 40 carbon atoms, a diarylamino group having 12 to 40 carbon atoms, an arylalkyl group having 7 to 40 carbon atoms, a cycloalkyl group having 3 to 40 carbon atoms and a heterocycloalkyl group having 3 to 40 carbon atoms, or a group forming a fused aliphatic ring, a fused aromatic ring, a fused heteroaliphatic ring or a fused heteroaromatic ring with an adjacent group, a halogen group, or a combination thereof, L is selected from a direct linkage, a substituted or unsubstituted aryl group having 6 to 30 carbon atoms, a substituted or unsubstituted fused aryl group having 10 to 30 carbon atoms, a substituted or unsubstituted heteroaryl group including 1 to 30 carbon atoms and N, S or O, and a substituted or unsubstituted fused heteroarylene group having 1 to 30 carbon atoms and N, S or O, Het is a substituted or unsubstituted heteroaryl group having 3 to 20 carbon atoms and N, and $A_1$ and $A_2$ are each independently hydrogen, a substituted or unsubstituted aryl group having 6 to 40 carbon atoms or a substituted or unsubstituted heteroaryl group having 1 to 40 carbon atoms.

The electron transport region may include at least one of the following Compounds 1 to 18:

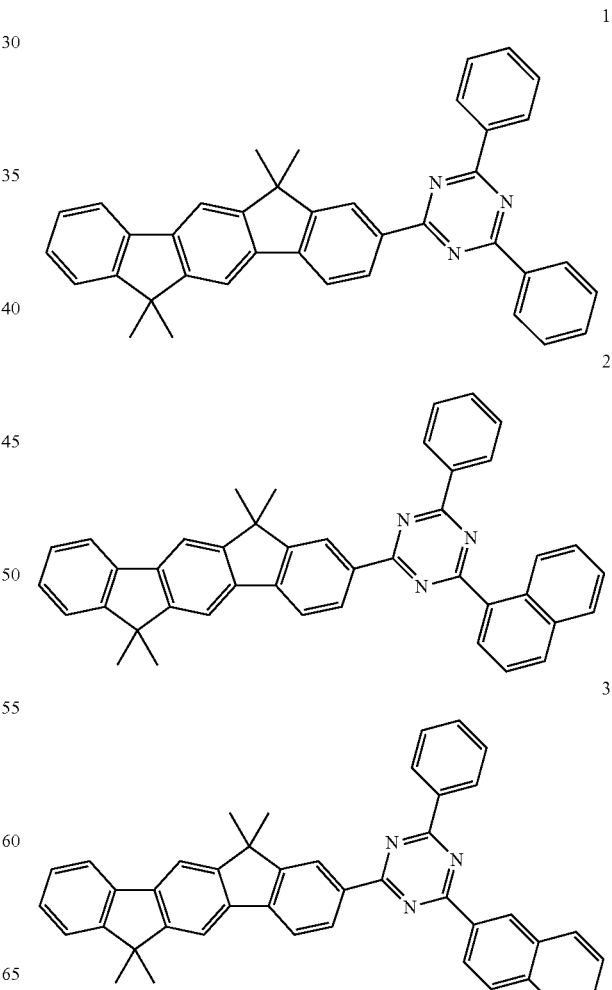

4
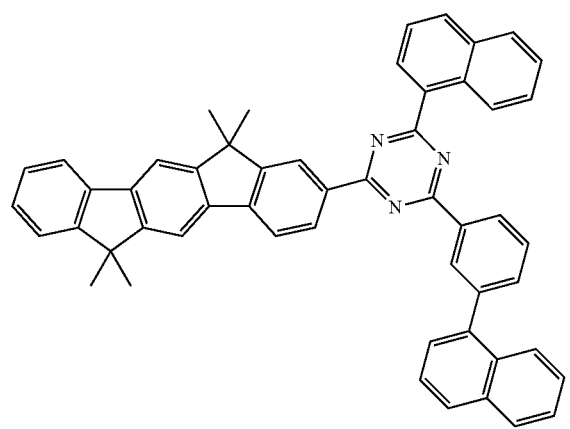
5
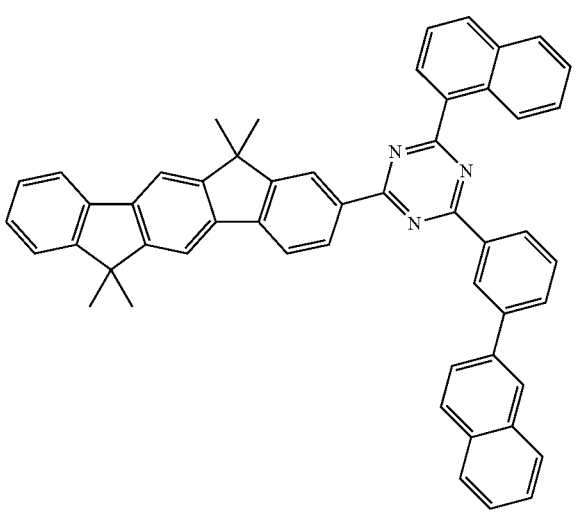
6
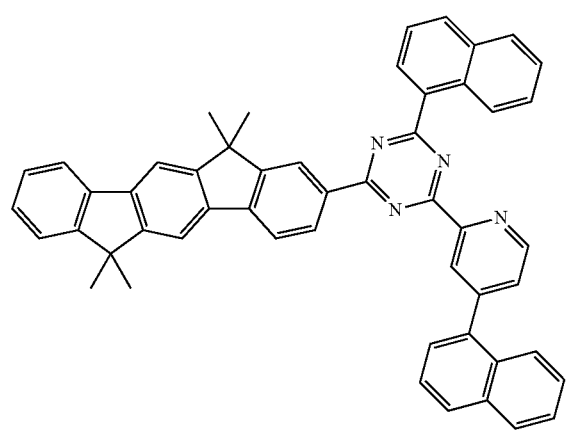
7
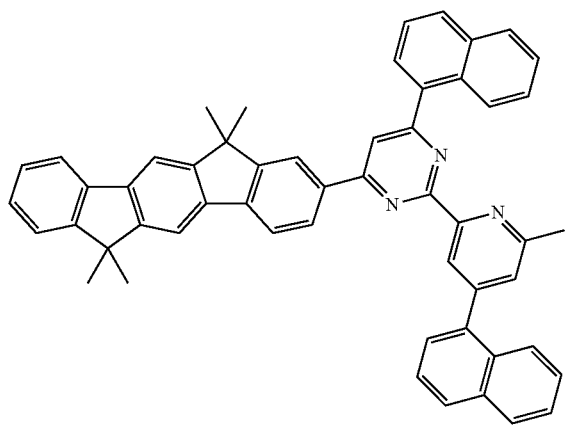
8
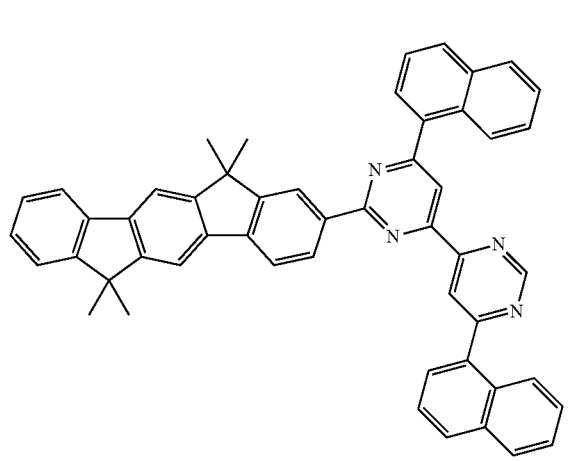
9
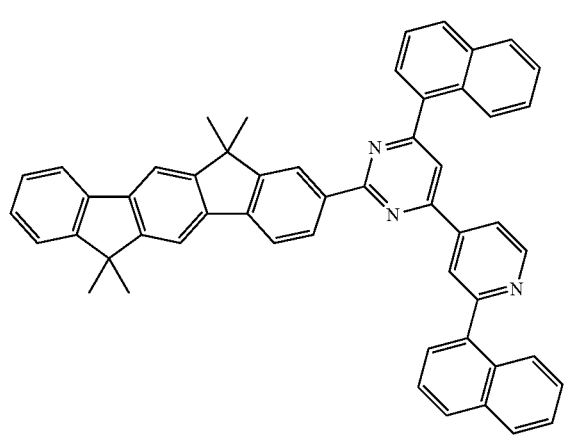

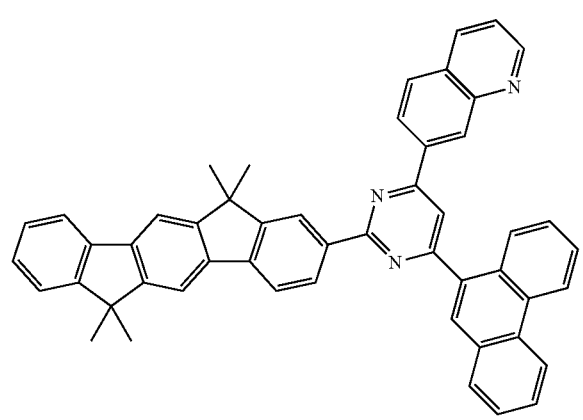
10
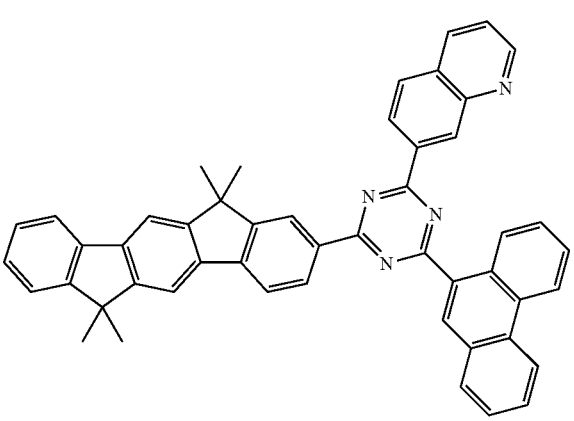
13
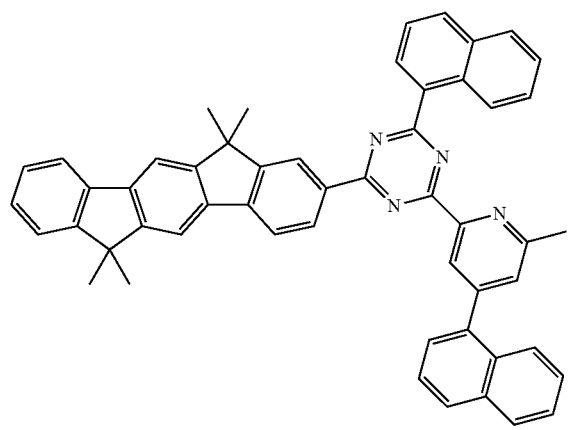
11
14
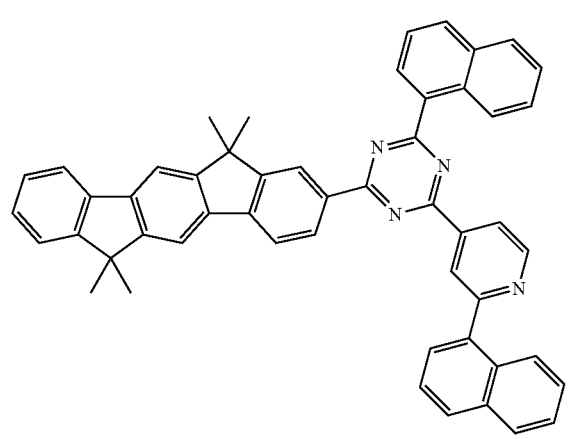
12
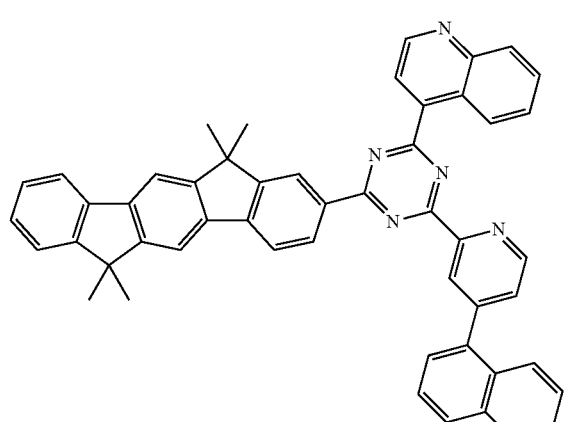
15

16

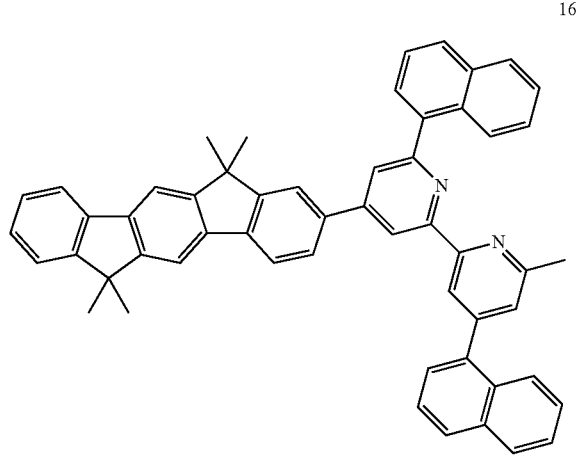

17

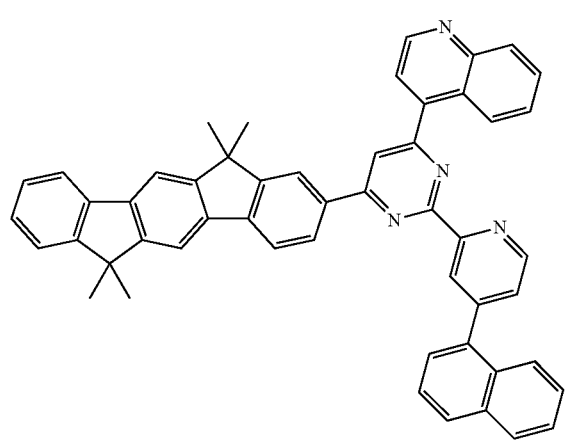

18

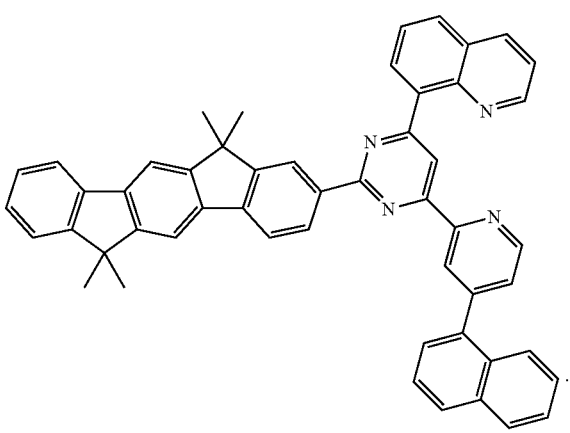

The emission layer may include a compound represented by the following Chemical Formula 2:

[Chemical Formula 2]

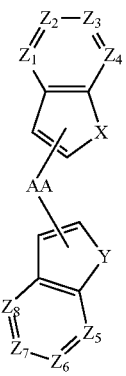

wherein, in Chemical Formula 2, AA is selected from a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, and a heteroaryl group having 1 to 60 carbon atoms, or AA has a structure such that a ring including X and a ring including Y are fused to form a fused aliphatic ring, a fused aromatic ring, a fused heteroaliphatic ring, or a fused heteroaromatic ring, X is selected from $N(Ar_3)$, O and S, Y is selected from $N(Ar_4)$, O and S, $Ar_a$ and $Ar_4$ are each independently selected from an alkyl group having 1 to 60 carbon atoms, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms and a heteroaryl group having 1 to 60 carbon atoms, $Z_1$ to $Z_8$ are each independently selected from $C(Ar_5)$ and N, and adjacent ones of $Ar_5$ are separate or are combined to each other to form a ring, each $Ar_5$ is independently selected from hydrogen, an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, a heteroaryl group having 1 to 60 carbon atoms, an arylthio group having 6 to 60 carbon atoms, an alkylthio group having 1 to 60 carbon atoms, a mono- or di-alkylamino group having 1 to 60 carbon atoms, a mono-arylamino group having 6 to 30 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group and a hydroxyl group, and the compound represented by Chemical Formula 2 does not include a compound in which X is N(Ar$_3$), Y is N(Ar$_4$), both Ar$_3$ and Ar$_4$ are the same, all Z$_1$ to Z$_8$ are C(Ar$_5$), and Ar$_5$ included in each of Z$_1$ to Z$_8$ are the same.

The alkyl group, the cycloalkyl group, the heterocycloalkyl group, the bicycloalkyl group, the adamantyl group, the alkenyl group, the alkynyl group, the aryl group, the alkoxy group, the aryloxy group, the heteroaryl group, the arylthio group, the alkylthio group, the alkylamino group, the arylamino group, the trialkylsilyl group, the dialkylarylsilyl group, the triarylsilyl group, the arylboranyl group, or the alkylboranyl group in Ar$_3$ to Ar$_5$ may be substituted with at least one substituent selected from an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, an aryl group having 6 to 60 carbon atoms and substituted with P(=O)RaRb, in which Ra and Rb are independently an alkyl group having 1 to 60 carbon atoms or an aryl group having 6 to 60 carbon atoms, a heteroaryl group having 1 to 60 carbon atoms, a heteroaryl group having 1 to 60 carbon atoms and substituted with an aryl group having 6 to 60 carbon atoms, a heteroaryl group having 1 to 60 carbon atoms and substituted with an alkyl group having 1 to 60 carbon atoms, an aralkyl group having 7 to 120 carbon atoms, an arylthio group having 6 to 60 carbon atoms, an alkylthio group having 1 to 60 carbon atoms, a mono- or di-alkylamino group having 1 to 30 carbon atoms, a mono- or di-arylamino group having 6 to 60 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group and a hydroxyl group.

The emission layer may include at least one of the following compounds, in which X, Y, and Z$_1$ to Z$_8$ are defined the same as X, Y, and Z$_1$ to Z$_8$ of Chemical Formula 2:

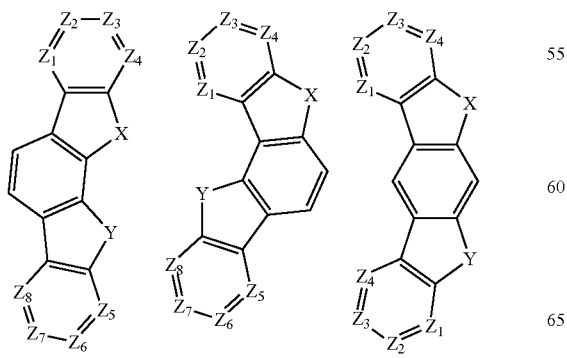

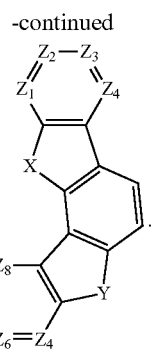

The emission layer may include at least one of the following Compounds H-1 to H-7:

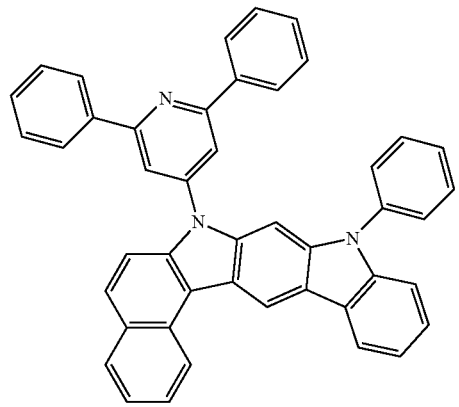

H1

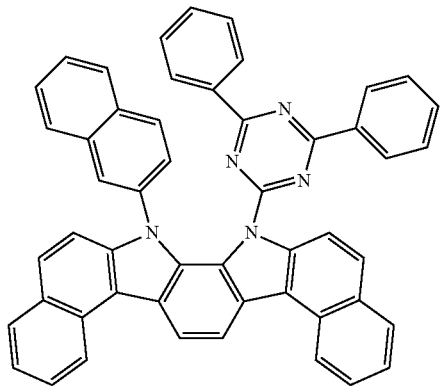

H2

H3
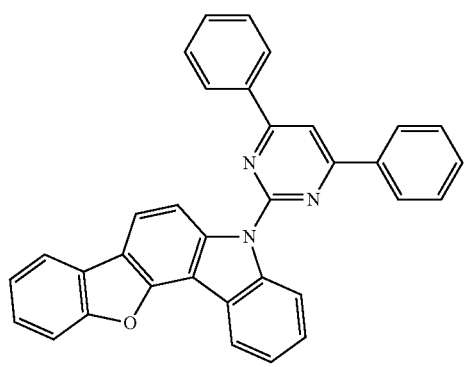
H4
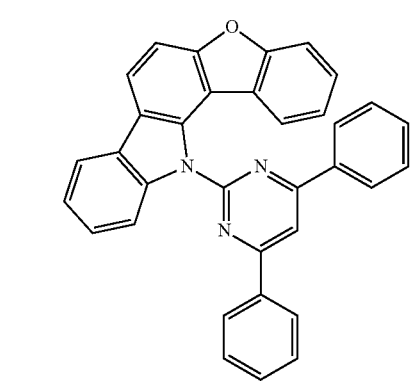
H5
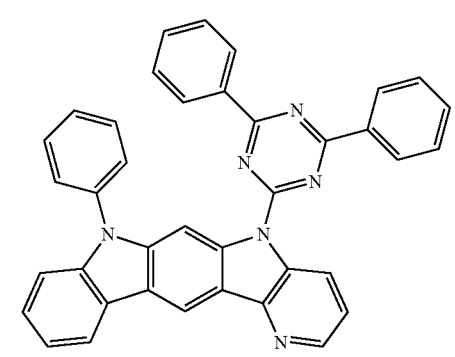
H6
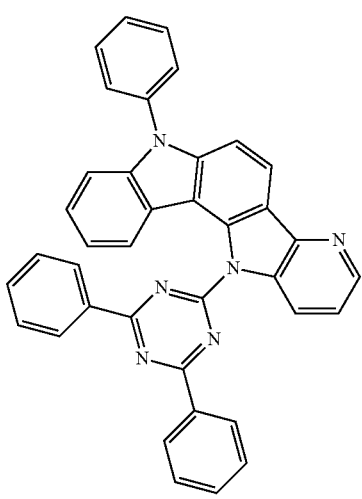
H7
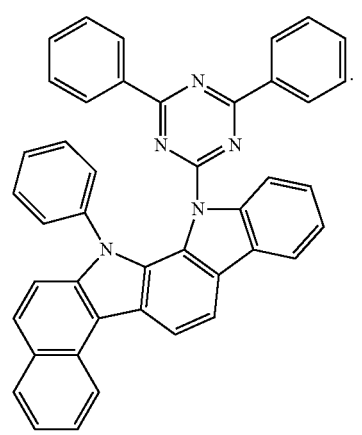
The emission layer may further include an arylamine-containing compound.
The arylamine-containing compound may be one of the following compounds:
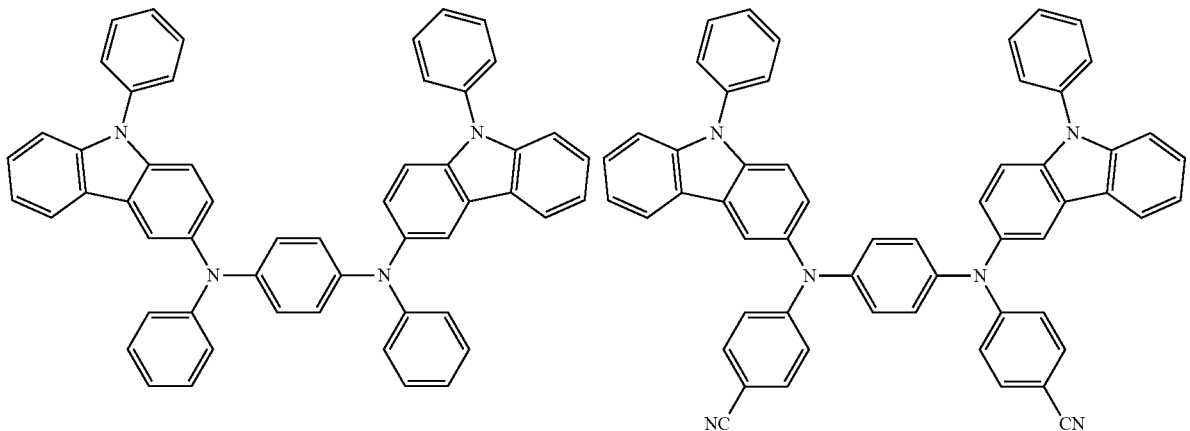

-continued
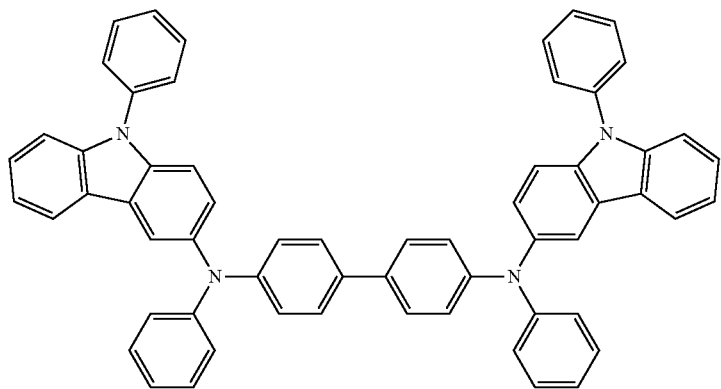
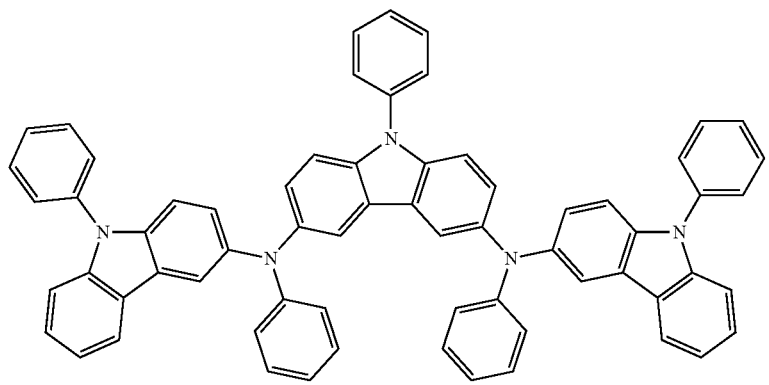
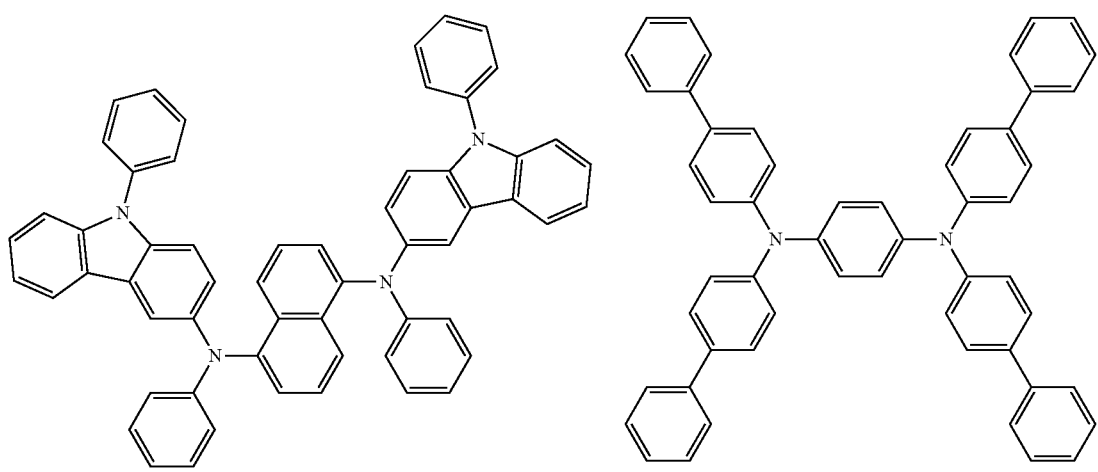
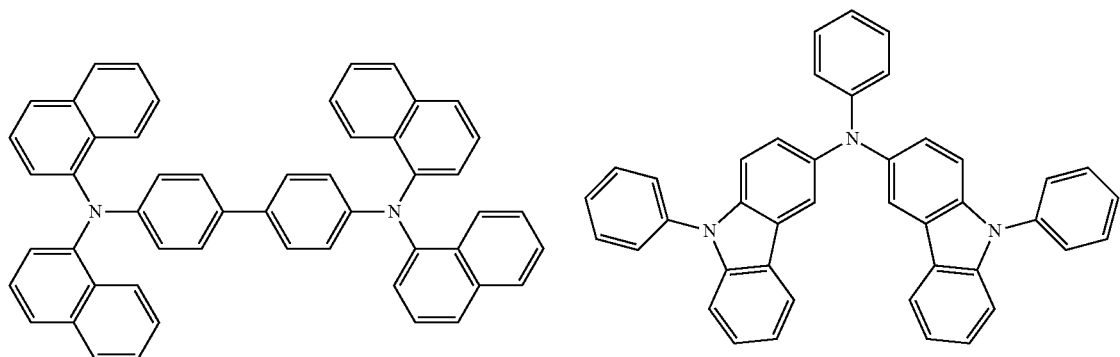

-continued
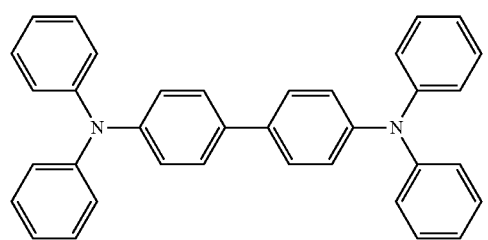
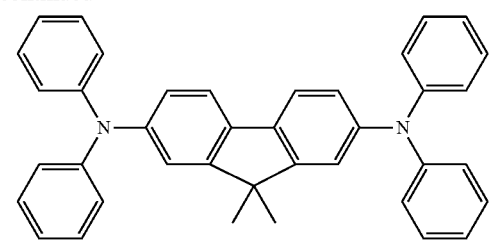
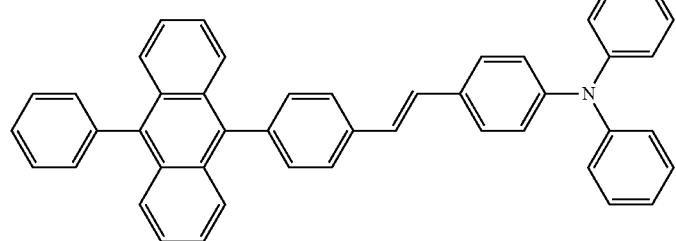
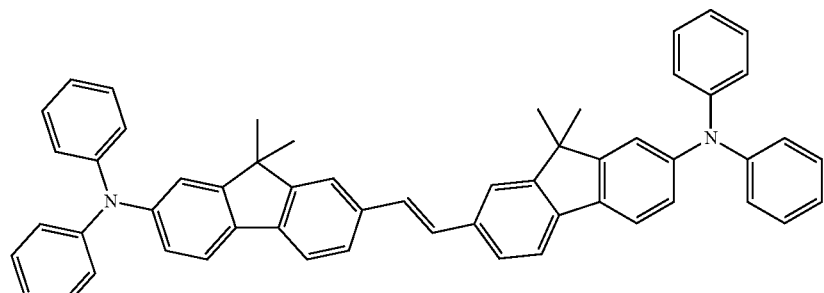
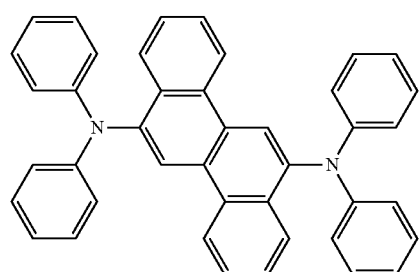
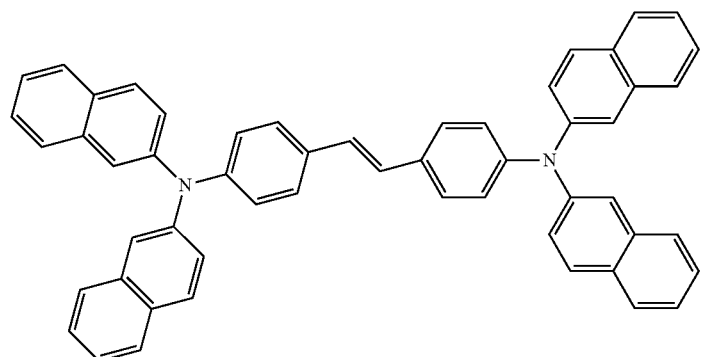
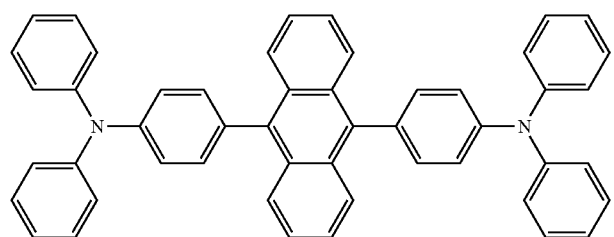

-continued
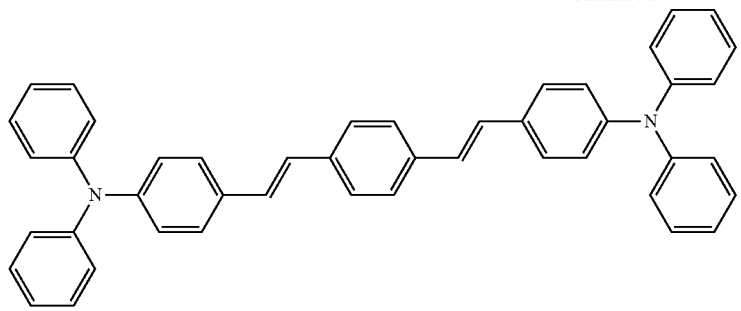
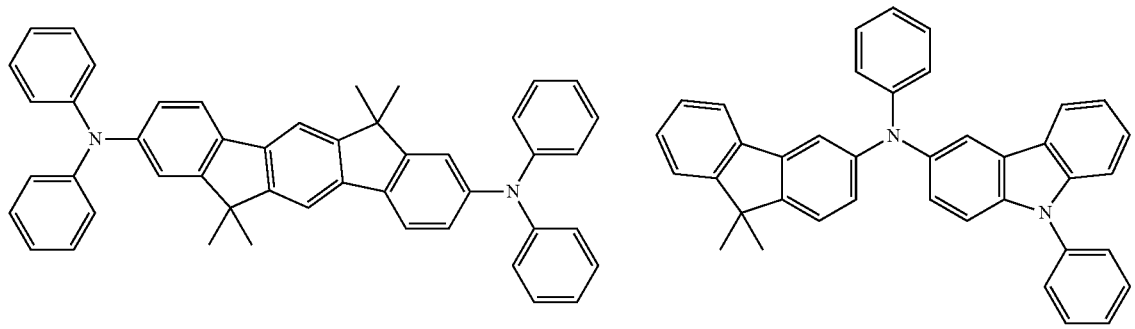
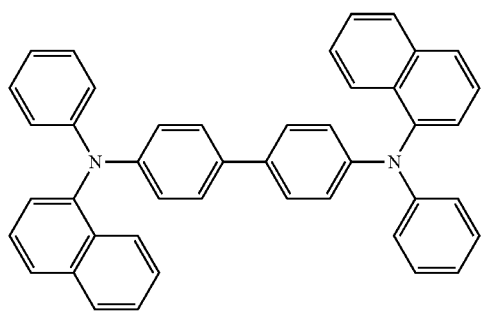
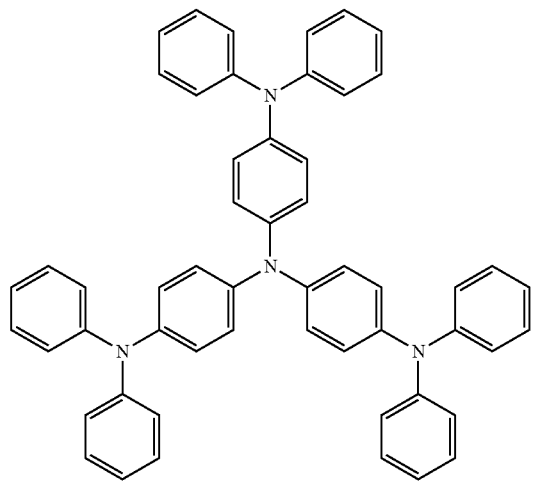
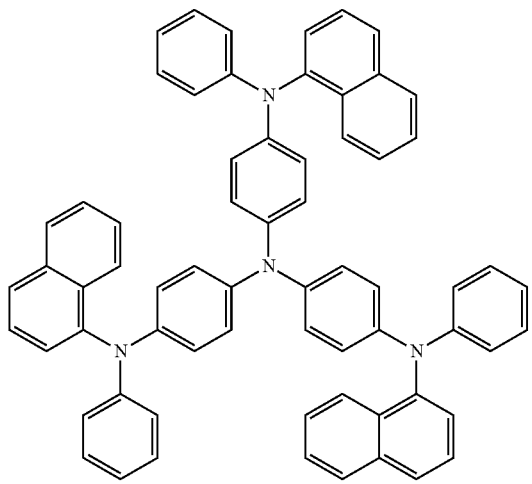
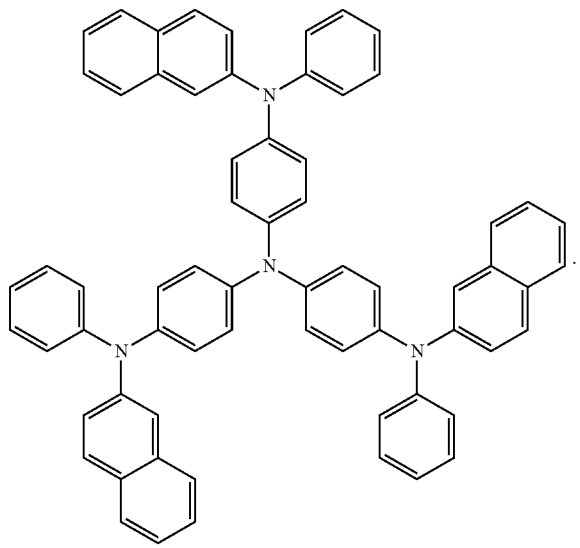

The emission layer may emit green light.

The embodiments may be realized by providing a display device including a plurality of pixels, at least one of the pixels including a hole transport region on a first electrode; an emission layer on the hole transport region; an electron transport region on the emission layer; and a second electrode on the electron transport region, wherein the electron transport region includes a compound represented by the following Chemical Formula 1:

[Chemical Formula 1]

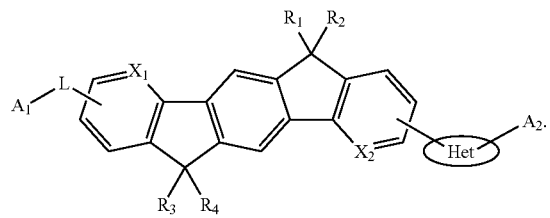

wherein, in Chemical Formula 1, $X_1$ and $X_2$ are each independently $CR_5$ or N, $R_1$ to $R_5$ are each independently selected from hydrogen, deuterium, an alkyl group having 1 to 40 carbon atoms, an aryl group having 6 to 40 carbon atoms, a heteroaryl group having 1 to 40 carbon atoms, an aryloxy group having 6 to 40 carbon atoms, an alkyloxy group having 1 to 40 carbon atoms, an arylamino group having 6 to 40 carbon atoms, a diarylamino group having 12 to 40 carbon atoms, an arylalkyl group having 7 to 40 carbon atoms, a cycloalkyl group having 3 to 40 carbon atoms and a heterocycloalkyl group having 3 to 40 carbon atoms, or a group forming a fused aliphatic ring, a fused aromatic ring, a fused heteroaliphatic ring or a fused heteroaromatic ring with an adjacent group, a halogen group or a combination thereof, L is selected from a direct linkage, a substituted or unsubstituted aryl group having 6 to 30 carbon atoms, a substituted or unsubstituted fused aryl group having 10 to 30 carbon atoms, a substituted or unsubstituted heteroaryl group including 1 to 30 carbon atoms and N, S or O, and a substituted or unsubstituted fused heteroarylene group having 1 to 30 carbon atoms and N, S or O, Het is a substituted or unsubstituted heteroaryl group having 3 to 20 carbon atoms and N, and $A_1$ and $A_2$ are each independently hydrogen, a substituted or unsubstituted aryl group having 6 to 40 carbon atoms or a substituted or unsubstituted heteroaryl group having 1 to 40 carbon atoms.

The electron transport region may include at least one of the following Compounds 1 to 18:

1

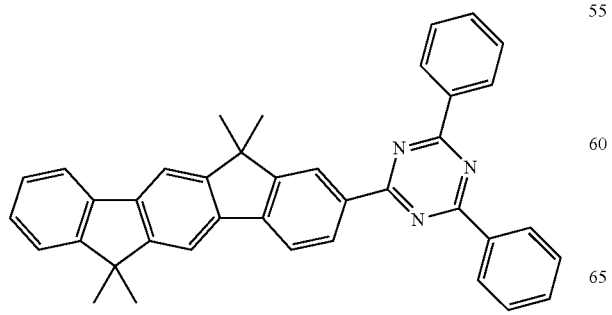

2

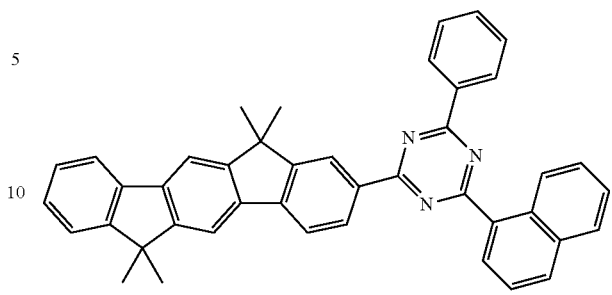

3

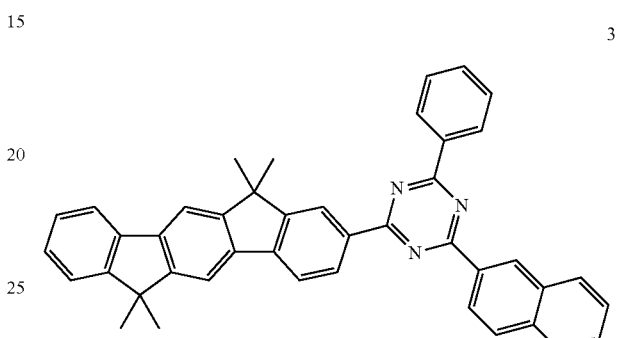

4

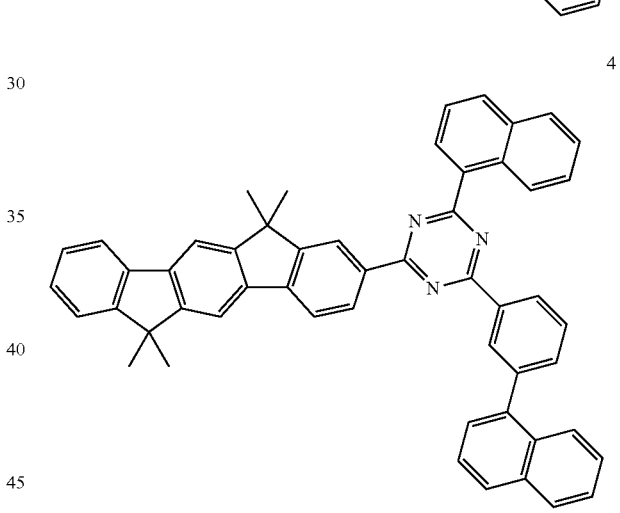

5

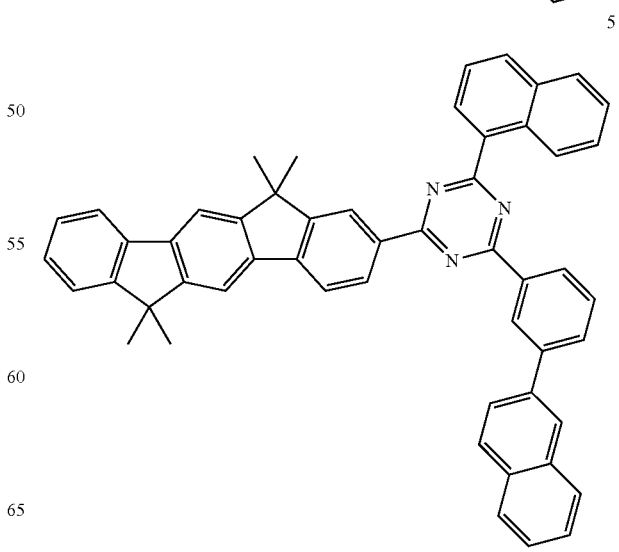

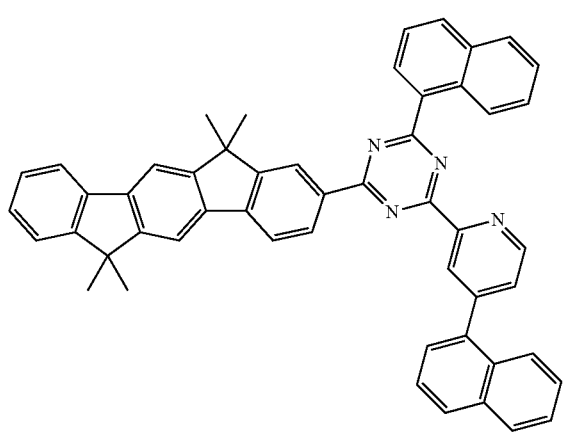
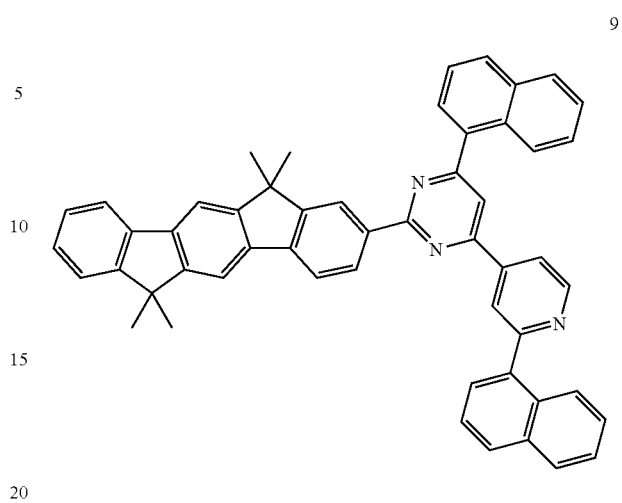
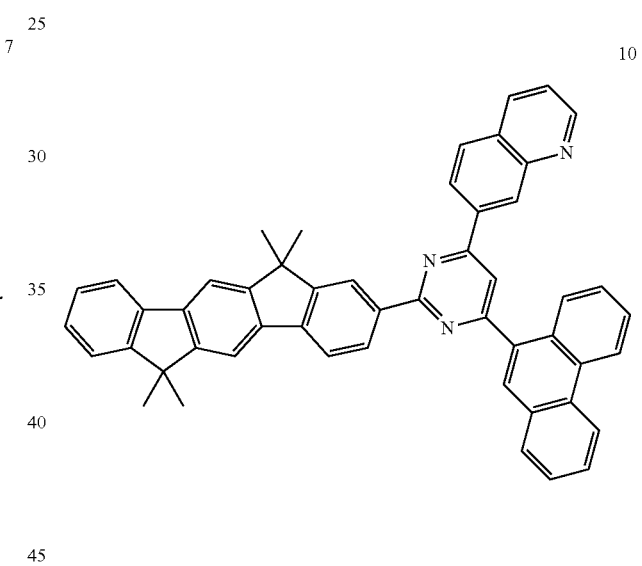
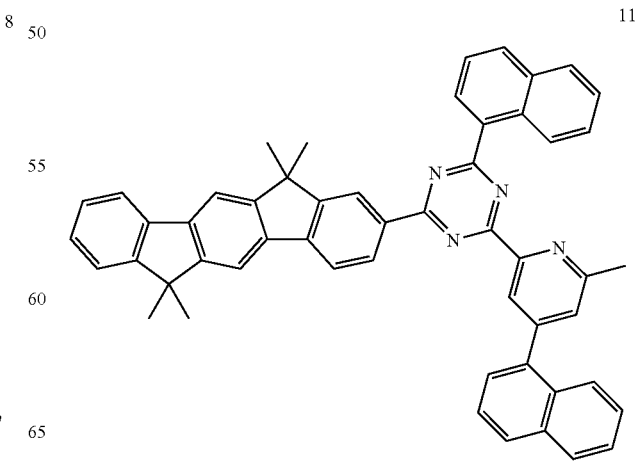

12
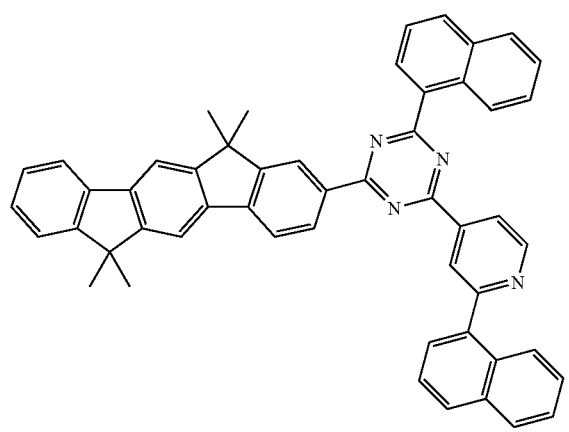
13
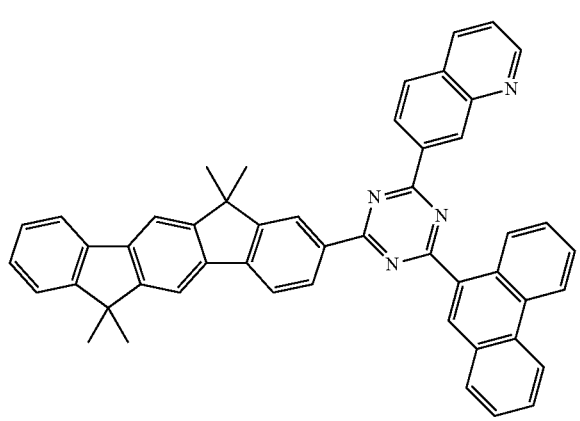
14
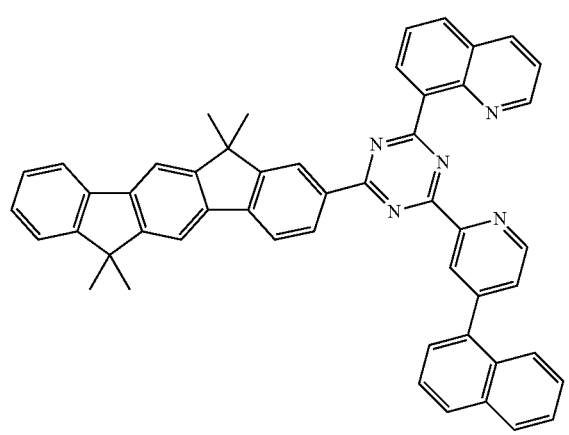
15
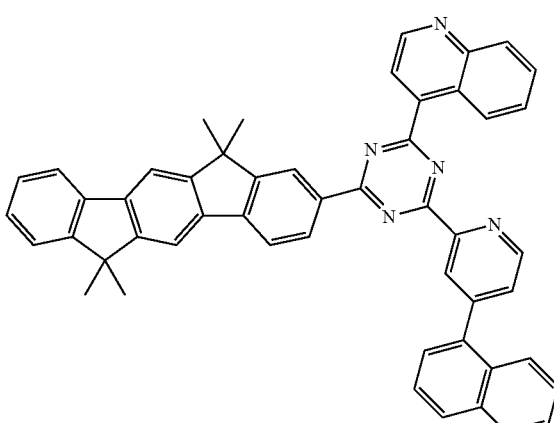
16
17
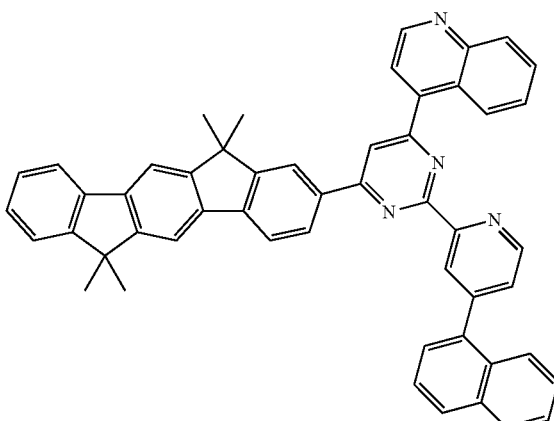

-continued

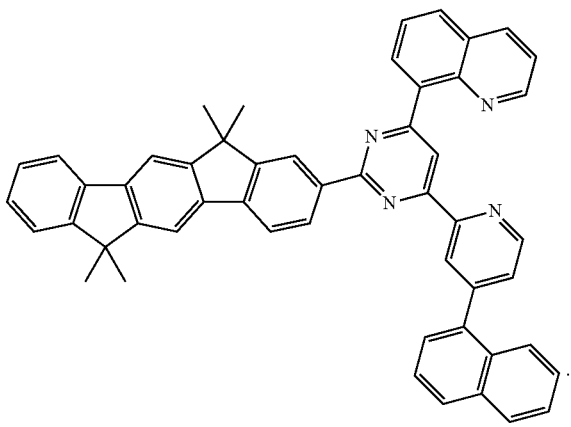

18

The emission layer may include a compound represented by the following Chemical Formula 2:

[Chemical Formula 2]

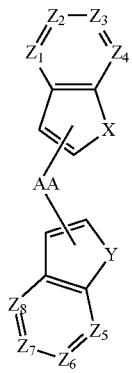

wherein, in Chemical Formula 2, AA is selected from a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, and a heteroaryl group having 1 to 60 carbon atoms, or AA has a structure such that a ring including X and a ring including Y are fused to form a fused aliphatic ring, a fused aromatic ring, a fused heteroaliphatic ring, or a fused heteroaromatic ring, X is selected from $N(Ar_3)$, O and S, Y is selected from $N(Ar_4)$, O and S, $Ar_3$ and $Ar_4$ are each independently selected from an alkyl group having 1 to 60 carbon atoms, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms and a heteroaryl group having 1 to 60 carbon atoms, $Z_1$ to $Z_8$ are each independently selected from $C(Ar_5)$ and N, and adjacent ones of $Ar_5$ are separate or are combined to each other to form a ring, each $Ar_5$ is independently selected from hydrogen, an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, a heteroaryl group having 1 to 60 carbon atoms, an arylthio group having 6 to 60 carbon atoms, an alkylthio group having 1 to 60 carbon atoms, a mono- or di-alkylamino group having 1 to 60 carbon atoms, a mono-arylamino group having 6 to 30 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group and a hydroxyl group, and the compound represented by Chemical Formula 2 does not include a compound in which X is $N(Ar_3)$, Y is $N(Ar_4)$, both $Ar_3$ and $Ar_4$ are the same, all $Z_1$ to $Z_8$ are $C(Ar_5)$, and $Ar_5$ included in each of $Z_1$ to $Z_8$ are the same.

The alkyl group, the cycloalkyl group, the heterocycloalkyl group, the bicycloalkyl group, the adamantyl group, the alkenyl group, the alkynyl group, the aryl group, the alkoxy group, the aryloxy group, the heteroaryl group, the arylthio group, the alkylthio group, the alkylamino group, the arylamino group, the trialkylsilyl group, the dialkylarylsilyl group, the triarylsilyl group, the arylboranyl group, or the alkylboranyl group in $Ar_3$ to $Ar_5$ may be substituted with at least one substituent selected from an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, an aryl group having 6 to 60 carbon atoms and substituted with $P(=O)RaRb$, in which Ra and Rb are independently an alkyl group having 1 to 60 carbon atoms or an aryl group having 6 to 60 carbon atoms, a heteroaryl group having 1 to 60 carbon atoms, a heteroaryl group having 1 to 60 carbon atoms and substituted with an aryl group having 6 to 60 carbon atoms, a heteroaryl group having 1 to 60 carbon atoms and substituted with an alkyl group having 1 to 60 carbon atoms, an aralkyl group having 7 to 120 carbon atoms, an arylthio group having 6 to 60 carbon atoms, an alkylthio group having 1 to 60 carbon atoms, a mono- or di-alkylamino group having 1 to 30 carbon atoms, a mono- or di-arylamino group having 6 to 60 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group and a hydroxyl group.

The emission layer may include at least one of the following compounds, in which X, Y, and $Z_1$ to $Z_8$ are defined the same as X, Y, and $Z_1$ to $Z_8$ of Chemical Formula 2:

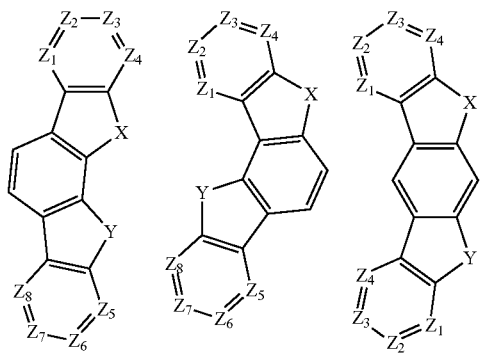

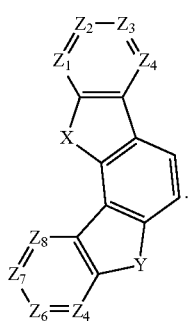

The emission layer may include at least one of the following Compounds H-1 to H-7:

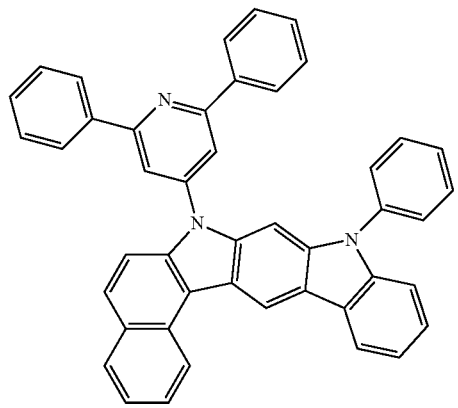

H1

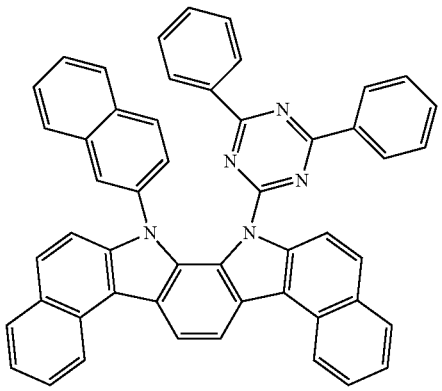

H2

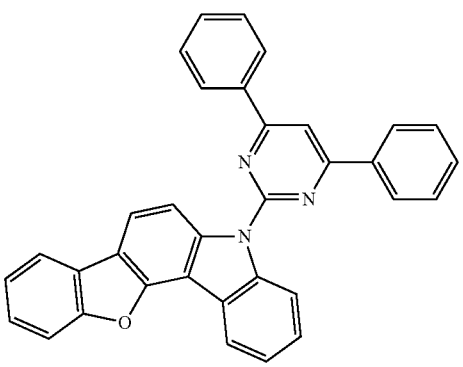

H3

H4
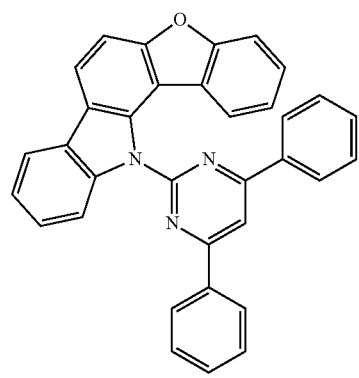
H6
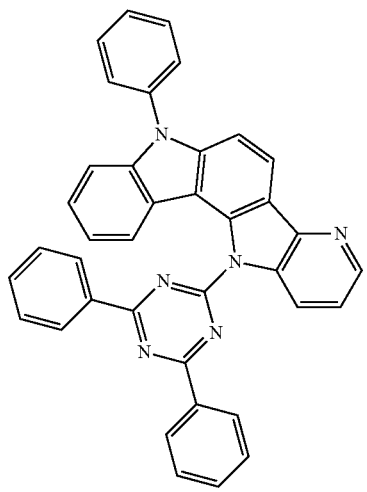
H5
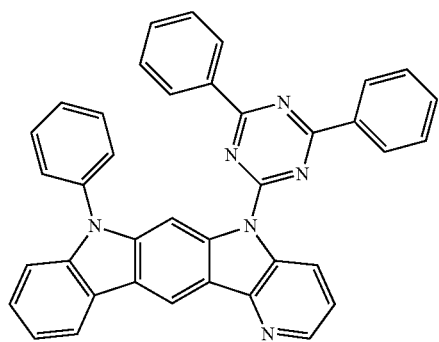
H7
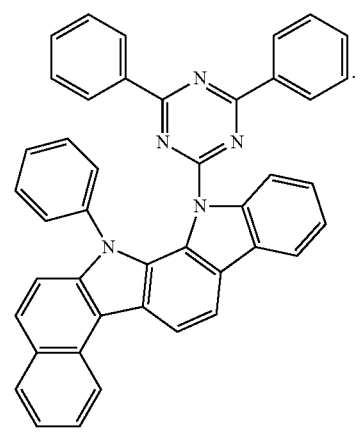
The emission layer may further include an arylamine-containing compound.
The arylamine-containing compound may be one of the following compounds:
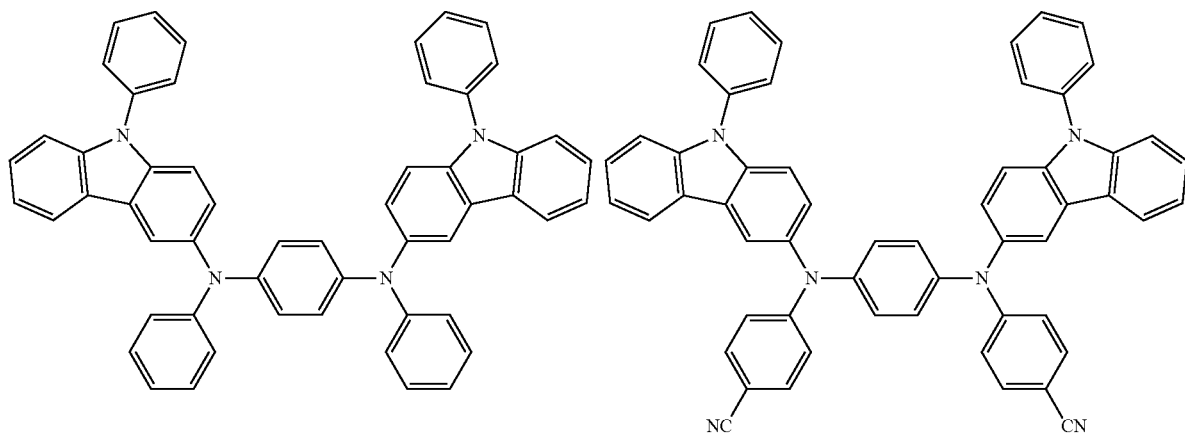

-continued
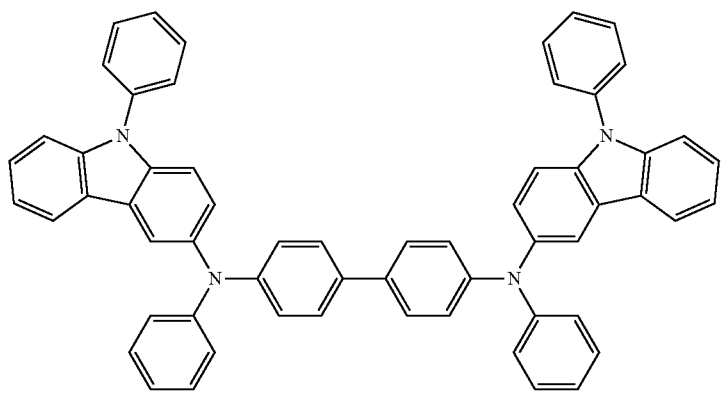
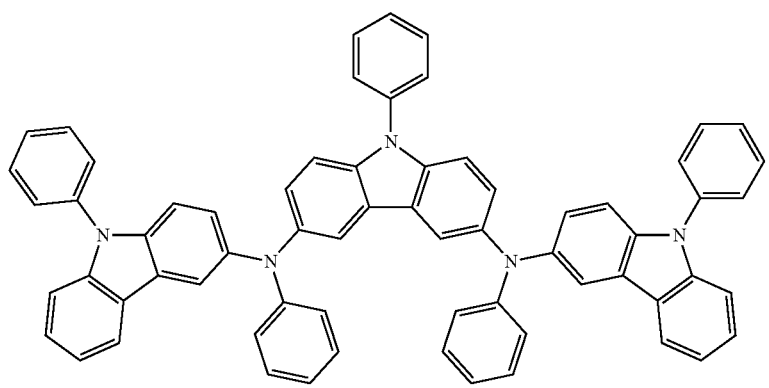
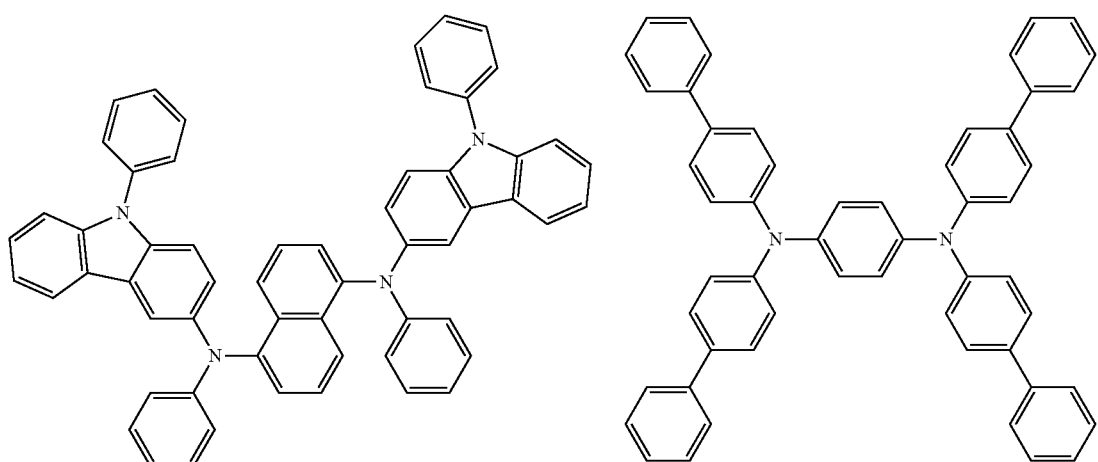
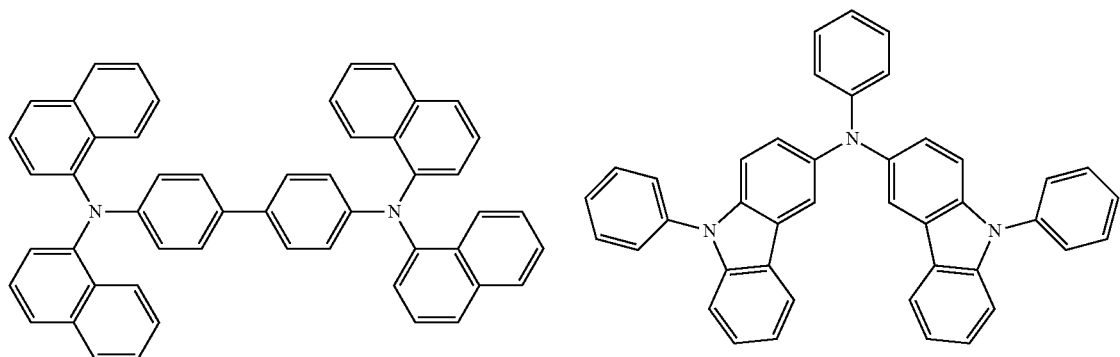

-continued
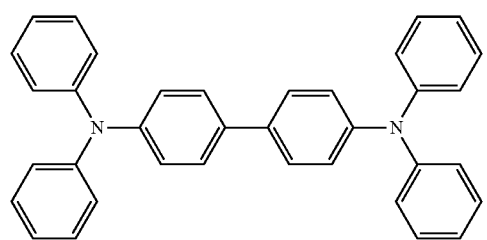
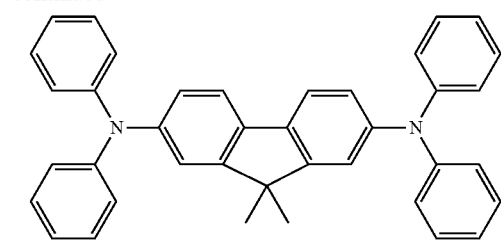
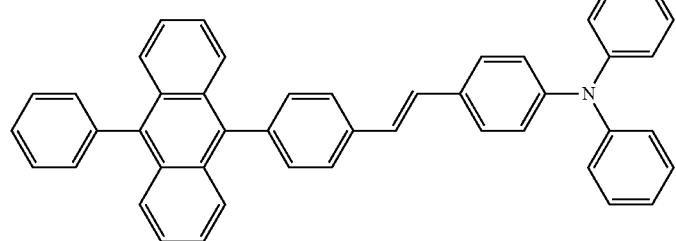
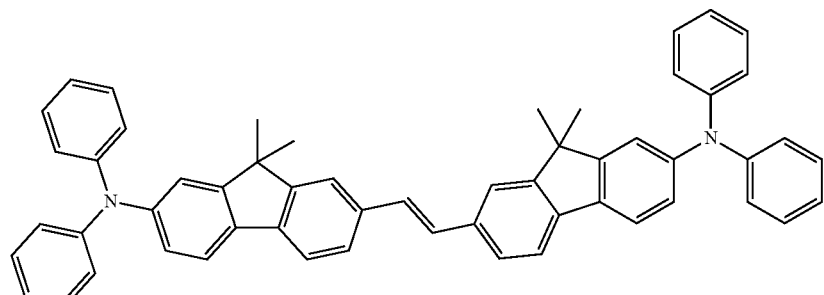
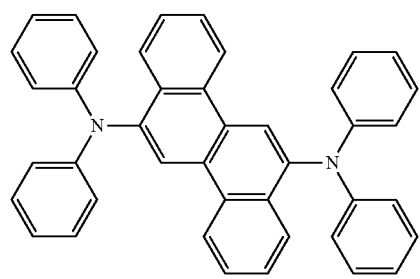
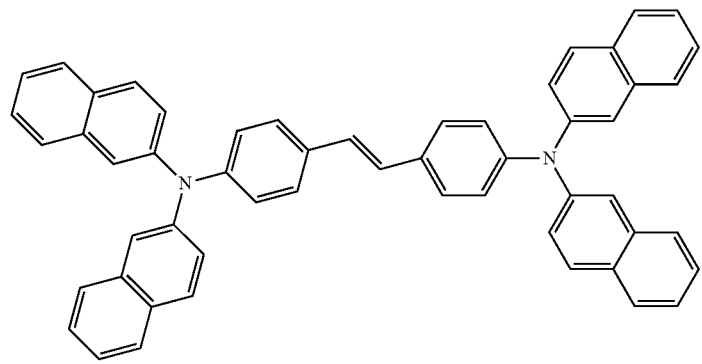
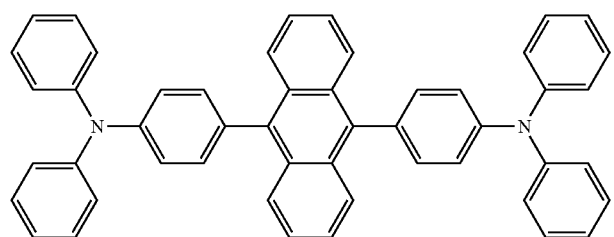

-continued
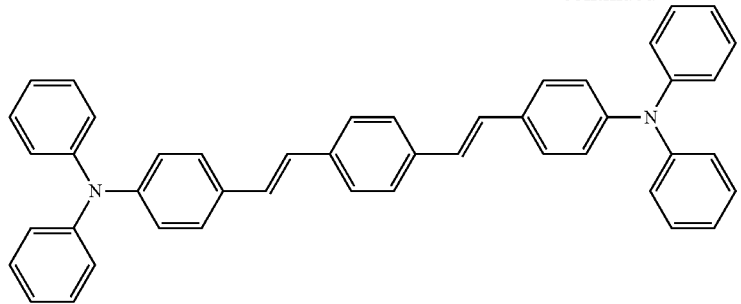
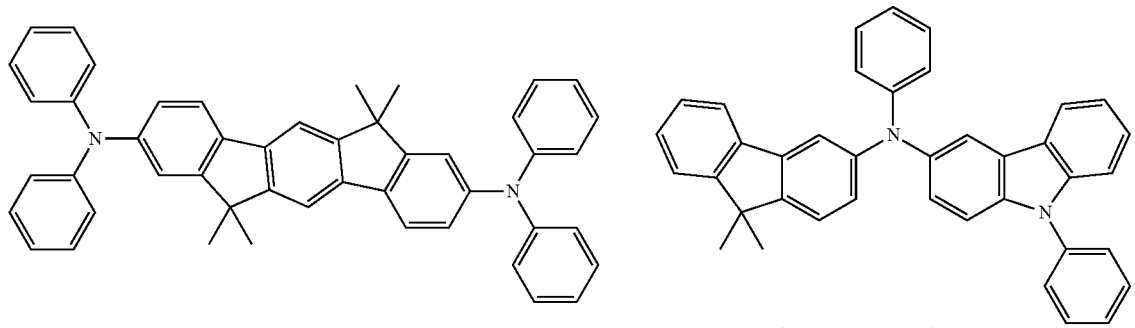
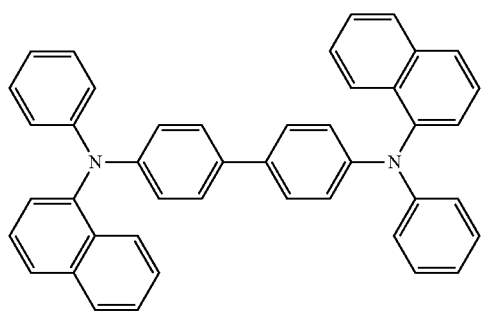
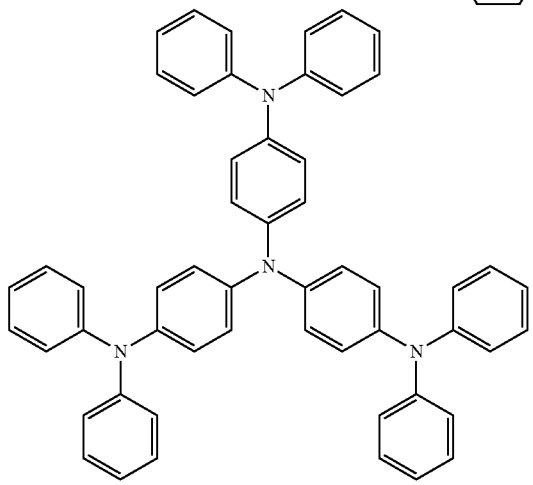
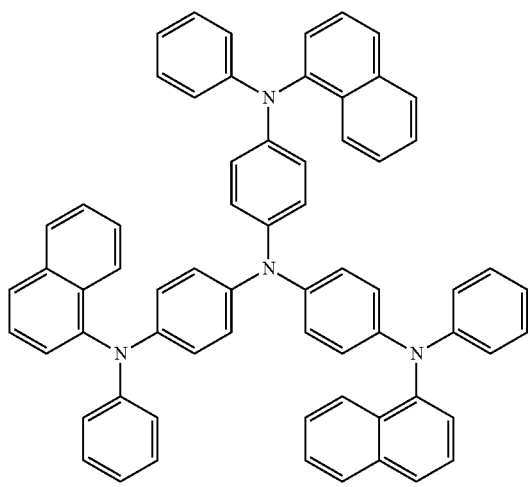
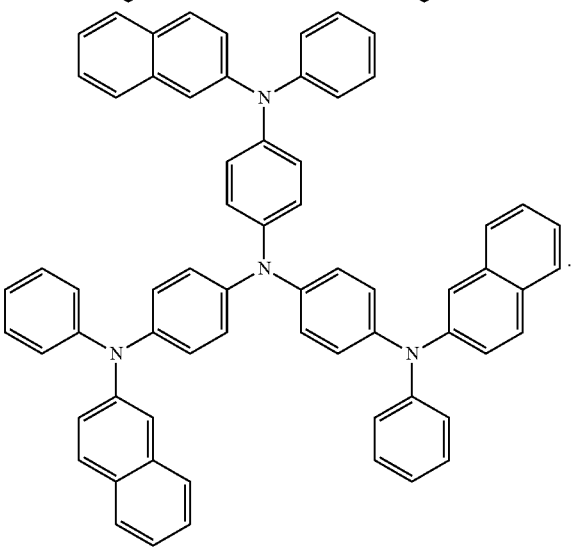
The emission layer may emit green light.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
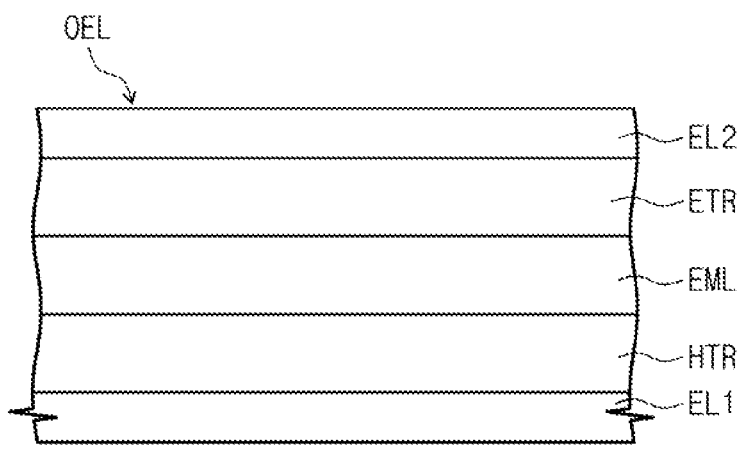
FIG. 1 illustrates a schematic cross-sectional view of an organic light emitting device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or substrate, or intervening layers may also be present. In addition, it will also be understood that when a layer is referred to as being "between" two layers, it can be the only layer between the two layers, or one or more intervening layers may also be present. Like reference numerals refer to like elements throughout.

It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "includes," "including," "comprises" and/or "comprising," when used in this specification, specify the presence of stated features, steps, operations, and/or devices, but do not preclude the presence or addition of one or more other features, steps, operations, and/or devices thereof.

Hereinafter, exemplary embodiments of the organic light emitting device will be described in detail.

Figure 2:
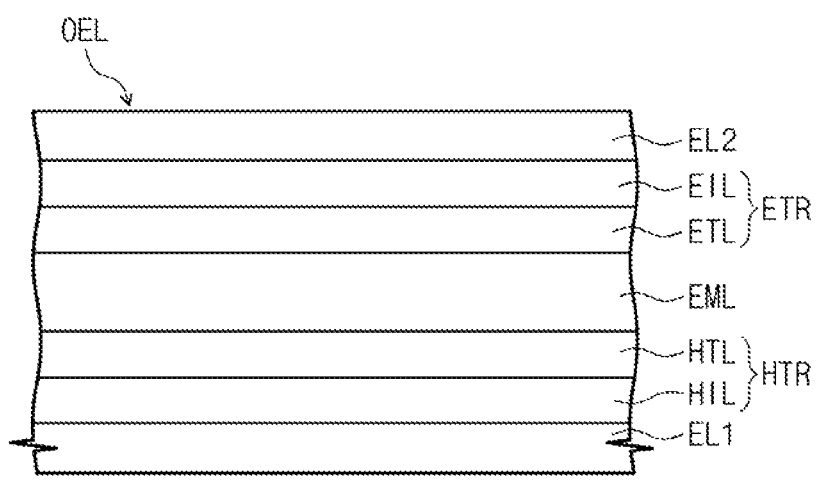
FIG. 2 illustrates a schematic cross-sectional view of an organic light emitting device according to an embodiment.

FIG. 1 illustrates a schematic cross-sectional view of an organic light emitting device OEL according to an embodiment. FIG. 2 illustrates a schematic cross-sectional view of an organic light emitting device according to an embodiment Referring to FIGS. 1 and 2, an organic light emitting device OEL according to an embodiment may include a first electrode EL1, a hole transport region HTR, an emission layer EML and an electron transport region ETR and a second electrode EL2.

The first electrode EL1 has conductivity. The first electrode EL1 may be a pixel electrode or an anode. The first electrode EL1 may be formed as a transmissive type electrode, a transflective type electrode or a reflective type electrode. When the first electrode EL1 is formed as the transmissive type electrode, the first electrode EL1 may be formed using a transparent metal oxide, e.g., indium tin oxide (ITO), indium zinc oxide (IZO), zinc oxide (ZnO), indium tin zinc oxide (ITZO), etc. When the first electrode EL1 is formed as the transflective type electrode or the reflective type electrode, the first electrode EL1 may include, e.g., Ag, Mg, Al, Pt, Pd, Au, Ni, Nd, Ir, Cr, or a mixture of metals.

On the first electrode EL1, an organic layer may be disposed. The organic layer may include the emission layer EML. The organic layer may further include the hole transport region HTR and the electron transport region ETR.

The hole transport region HTR may be provided on the first electrode EL1. The hole transport region HTR may include at least one of a hole injection layer HIL, a hole transport layer HTL, a buffer layer, and an electron blocking layer.

The hole transport region HTR may have a single layer formed by using a single material, a single layer formed by using a plurality of different materials or a multilayered structure including a plurality of layers formed by using a plurality of different materials.

For example, the hole transport region HTR may have the structure of a single layer formed by using a plurality of different materials, or a laminated structure from the first electrode EL1, of hole injection layer HIL/hole transport layer HTL, hole injection layer HIL/hole transport layer HTL/buffer layer, hole injection layer HIL/buffer layer, hole transport layer HTL/buffer layer or hole injection layer HIL/hole transport layer HTL/electron blocking layer.

The hole transport region HTR may be formed by using various methods such as a vacuum deposition method, a spin coating method, a cast method, a Langmuir-Blodgett (LB) method, an inkjet printing method, a laser printing method, a laser induced thermal imaging (LITI) method, etc.

When the hole transport region HTR includes the hole injection layer HIL, the hole transport region HTR may include a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), etc.

When the hole transport region HTR includes the hole transport layer HTL, the hole transport region HTR may include a carbazole derivative such as N-phenylcarbazole and polyvinyl carbazole, a fluorine-based derivative, N,N'-bis(3-methylphenyl)-N,N'-diphenyl-[1,1-biphenyl]-4,4'-diamine (TPD), a triphenylamine-based derivative such as 4,4',4"-tris(N-carbazolyl)triphenylamine (TCTA), N,N'-di(1-naphthyl)-N,N'-diphenylbenzidine (NPB), 4,4'-cyclohexylidene bis[N,N-bis(4-methylphenyl)benzeneamine] (TAPC), etc.

The thickness of the hole transport region HTR may be from about 100 Å to about 10,000 Å, e.g., from about 100 Å to about 1,000 Å. When the hole transport region HTR includes both the hole injection layer HIL and the hole transport layer HTL, the thickness of the hole injection layer HIL may be from about 100 Å to about 10,000 Å, e.g., from about 100 Å to about 1,000 Å, and the thickness of the hole transport layer HTL may be from about 50 Å to about 2,000 Å, e.g., from about 100 Å to about 1,500 Å. When the thicknesses of the hole transport region HTR, the hole injection layer HIL and the hole transport layer HTL satisfy the above-described ranges, satisfactory hole transport properties may be obtained without substantial increase of a driving voltage.

The hole transport region HTR may further include a charge generating material other than the above-described materials to improve conductivity. The charge generating material may be dispersed in the hole transport region HTR uniformly or non-uniformly. The charge generating material may be, e.g., a p-dopant. The p-dopant may be one of a quinone derivative, a metal oxide and a cyano group-containing compound. Non-limiting examples of the p-dopant may include a quinone derivative such as tetracyanoquinodimethane (TCNQ), 2,3,5,6-tetrafluoro-tetracyanoquinodimethane (F4-TCNQ), etc., a metal oxide such as tungsten oxide, molybdenum oxide, etc.

As described above, the hole transport region HTR may further include one of a buffer layer and an electron blocking layer other than the hole injection layer HIL and the hole transport layer HTL. The buffer layer may compensate an optical resonance range according to the wavelength of light emitted from the emission layer EML and increase light emission efficiency. Materials included in the hole transport region HTR may be used as materials included in the buffer layer. The electron blocking layer is a layer that helps reduce and/or prevent electron injection from the electron transport region ETR to the hole transport region HTR.

The emission layer EML may be provided on the hole transport region HTR. The emission layer EML may have a single layer formed by using a single material, a single layer formed by using a plurality of different materials, or a multilayered structure including a plurality of layers formed by using a plurality of layers formed by using a plurality of different materials.

The emission layer EML may be formed by using various methods such as a vacuum deposition method, a spin coating method, a cast method, an LB method, an inkjet printing method, a laser printing method, an LITI method, etc.

The emission layer EML may emit, e.g., green light. The emission layer EML may be formed using a material emitting green light and may include a phosphorescent material or a fluorescent material. In addition, the emission layer EML may include a host or a dopant.

In an implementation, the host may include a compound represented by the following Chemical Formula 2.

[Chemical Formula 2]

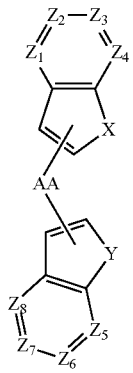

In the above Chemical Formula 2, AA may be selected from, e.g., a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, and a heteroaryl group having 1 to 60 carbon atoms. In an implementation, AA may represent or form a fused structure, e.g., a ring including X and a ring including Y may be fused via AA to form a fused aliphatic ring, a fused aromatic ring, a fused heteroaliphatic ring, or a fused heteroaromatic ring.

X may be selected from $N(Ar_3)$, O, and S, Y may be selected from $N(Ar_4)$, O and S. $Ar_3$ and $Ar_4$ may each independently be selected from, e.g., an alkyl group having 1 to 60 carbon atoms, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, and a heteroaryl group having 1 to 60 carbon atoms. $Z_1$ to $Z_8$ may each independently be selected from $C(Ar_5)$ and N. Each $Ar_5$, e.g., included in $Z_1$ to $Z_8$, may be different from each other. Adjacent ones of $Ar_5$ may be separate or may be combined or bonded to each other to form a ring. Each $Ar_5$ (included in $Z_1$ to $Z_8$) may each independently be selected from hydrogen, an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, a heteroaryl group having 1 to 60 carbon atoms, an arylthio group having 6 to 60 carbon atoms, an alkylthio group having 1 to 60 carbon atoms, a mono- or di-alkylamino group having 1 to 60 carbon atoms, a mono-arylamino group having 6 to 30 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group, and a hydroxyl group.

In an implementation, the compound represented by Chemical Formula 2 may not include a compound in which X is $N(Ar_3)$, Y is $N(Ar_4)$, both $Ar_3$ and $Ar_4$ are the same, all $Z_1$ to $Z_8$ are $C(Ar_5)$, and all $Ar_5$ in $Z_1$ to $Z_8$ are the same.

The alkyl group, the cycloalkyl group, the heterocycloalkyl group, the bicycloalkyl group, the adamantyl group, the alkenyl group, the alkynyl group, the aryl group, the alkoxy group, the aryloxy group, the heteroaryl group, the arylthio group, the alkylthio group, the alkylamino group, the arylamino group, the trialkylsilyl group, the dialkylarylsilyl group, the triarylsilyl group, the arylboranyl group, or the alkylboranyl group in Ar₃ to Ar₄, if substituted, may each independently be substituted with at least one substituent selected from an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, an aryl group having 6 to 60 carbon atoms and substituted with P(=O)RaRb [in which Ra and Rb are independently an alkyl group having 1 to 60 carbon atoms or an aryl group having 6 to 60 carbon atoms], a heteroaryl group having 1 to 60 carbon atoms, a heteroaryl group having 1 to 60 carbon atoms and substituted with an aryl group having 6 to 60 carbon atoms, a heteroaryl group having 1 to 60 carbon atoms and substituted with an alkyl group having 1 to 60 carbon atoms, an aralkyl group having 7 to 120 carbon atoms, an arylthio group having 6 to 60 carbon atoms, an alkylthio group having 1 to 60 carbon atoms, a mono- or di-alkylamino group having 1 to 30 carbon atoms, a mono- or di-arylamino group having 6 to 60 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group, and a hydroxyl group.

In an implementation, the host may include at least one of the following compounds, in which X, Y, and $Z_1$ to $Z_8$ are defined the same as X, Y, and $Z_1$ to $Z_8$ of Chemical Formula 2. For example, the compound represented by Chemical Formula 2 may be one of the following compounds.

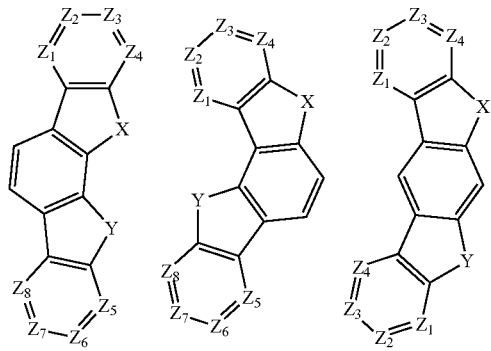

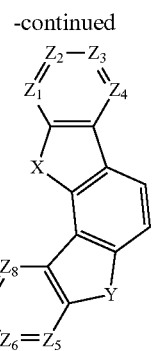

In an implementation, the host may include at least one of the following Compounds H-1 to H-7. For example, the compound represented by Chemical Formula 2 may be one of the following Compounds H-1 to H-7.

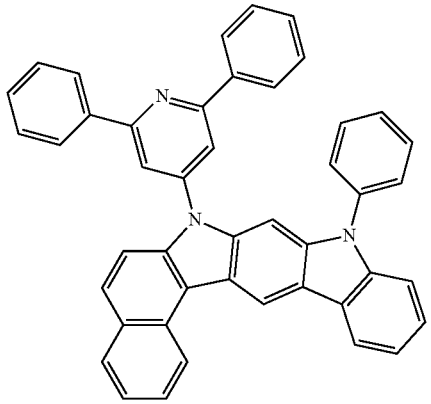

H-1

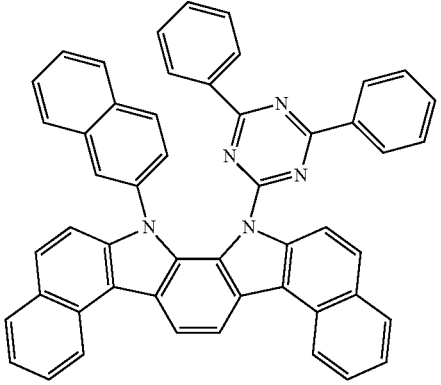

H-2

H-3
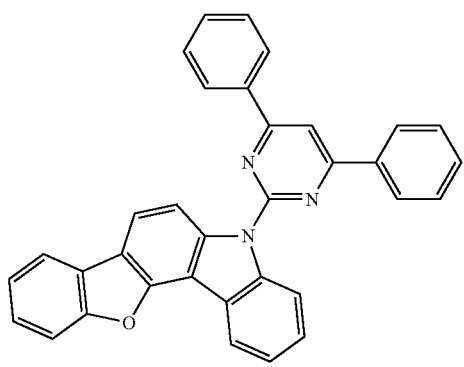
H-4
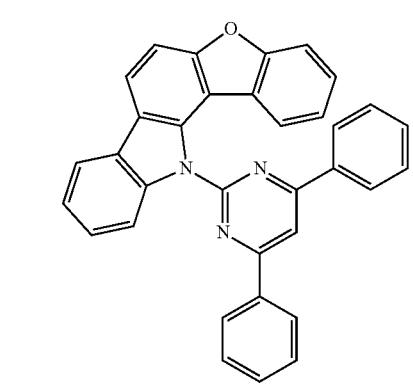
H-5
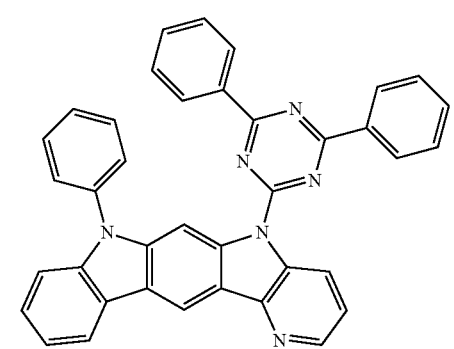
H-6
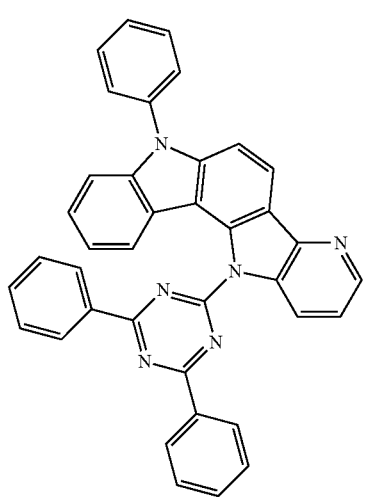
H-7
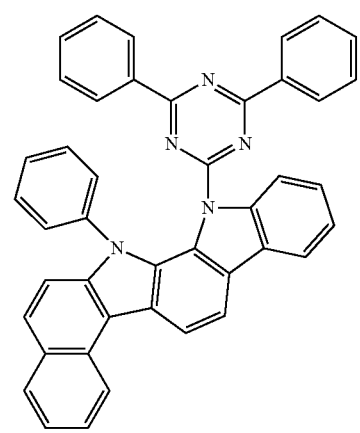
The emission layer may further include at least one of an arylamine-containing or arylamine-based compound and a styryl arylamine-containing compound.
The arylamine-containing compound may include at least one of the following compounds.
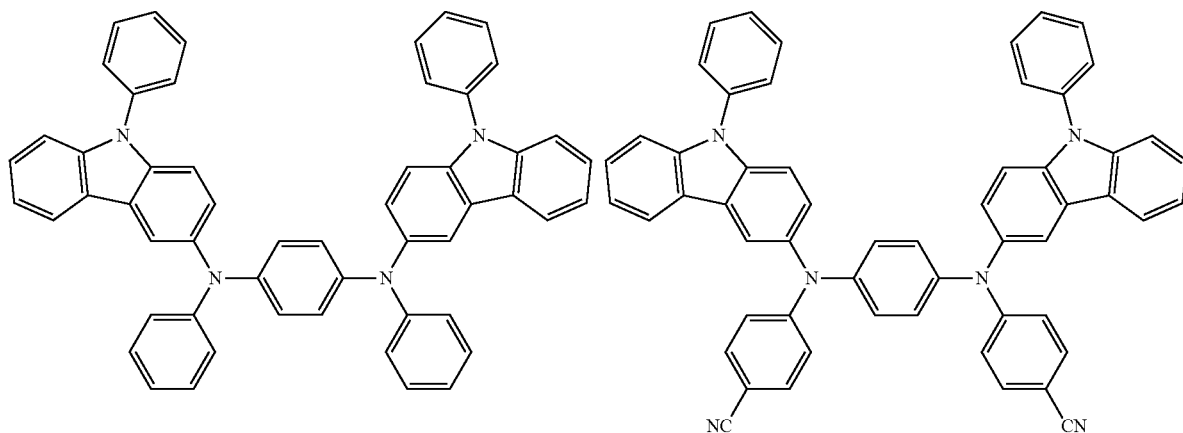

-continued
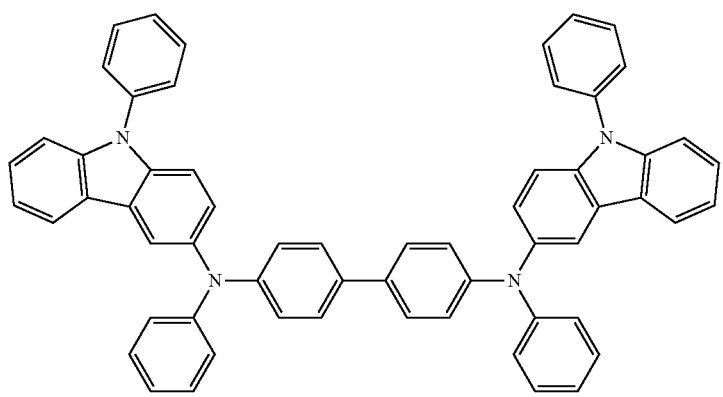
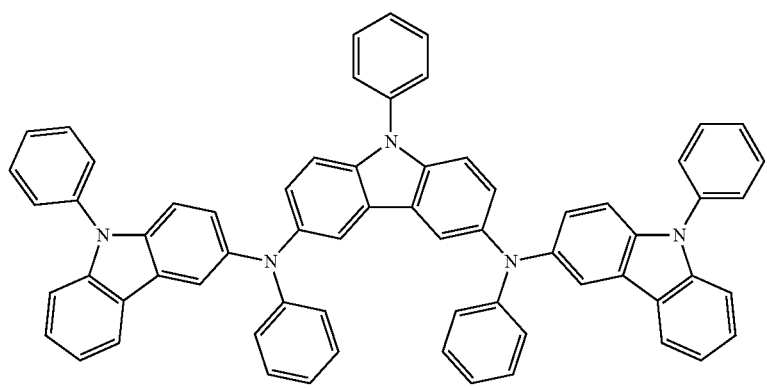
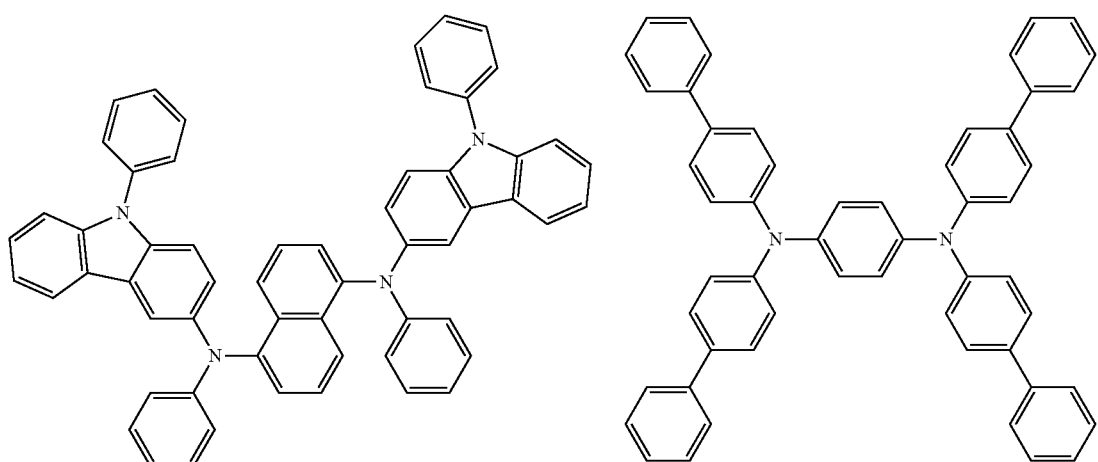
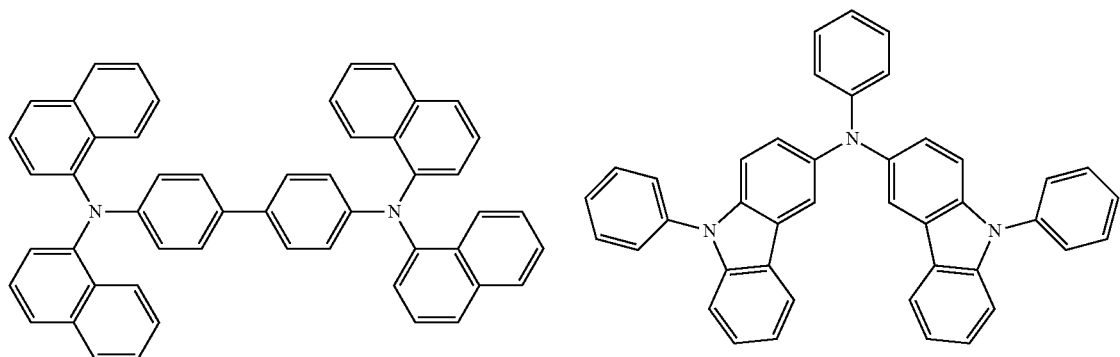

-continued
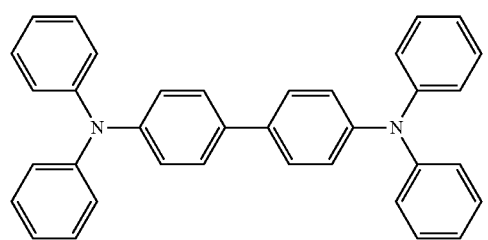
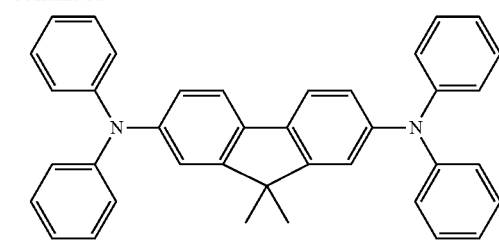
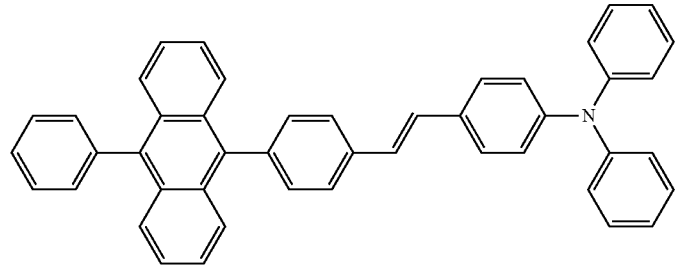
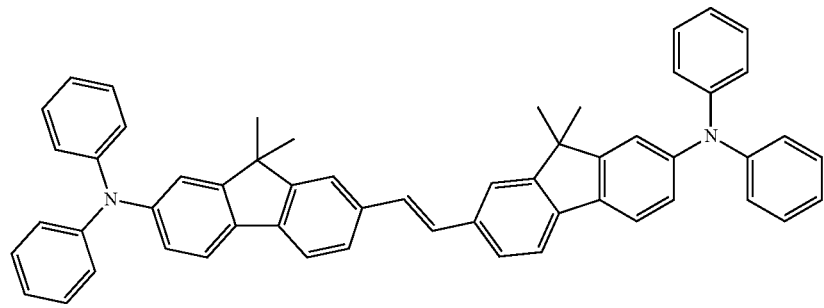
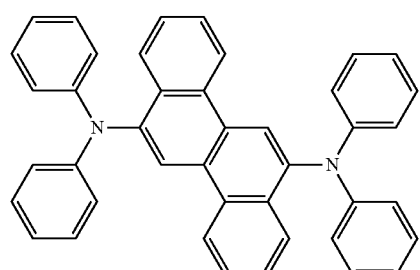
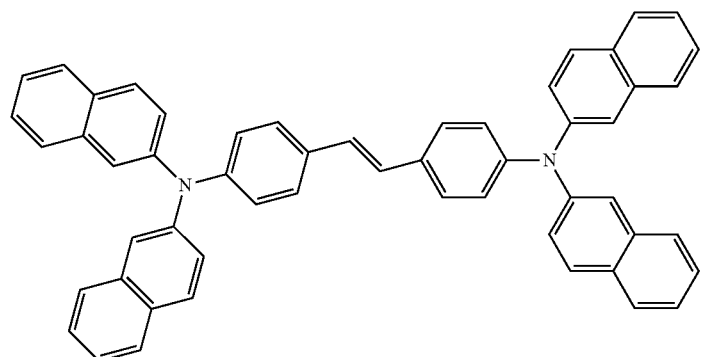
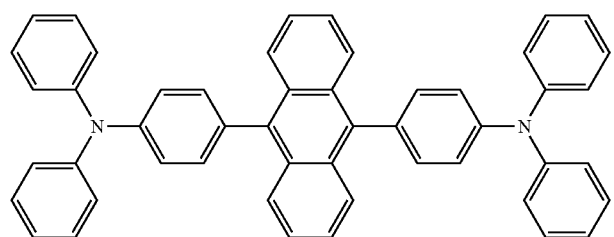

-continued
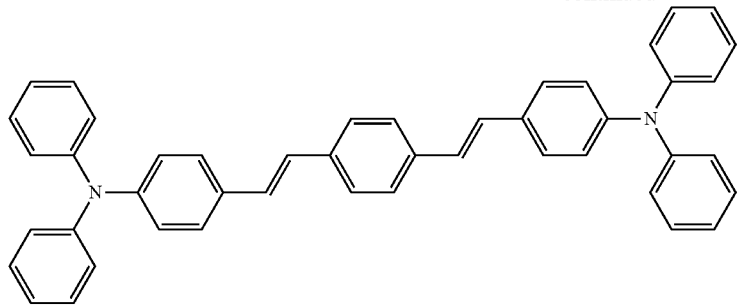
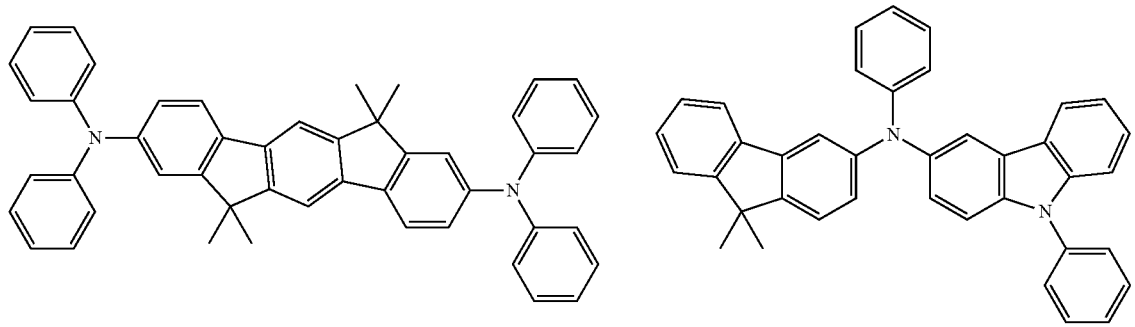
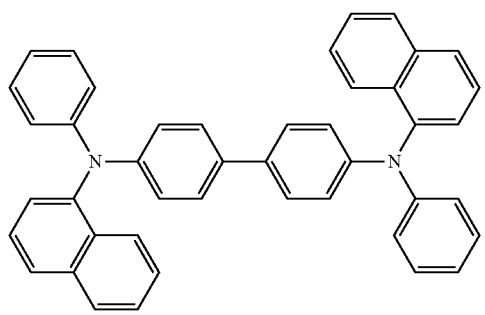
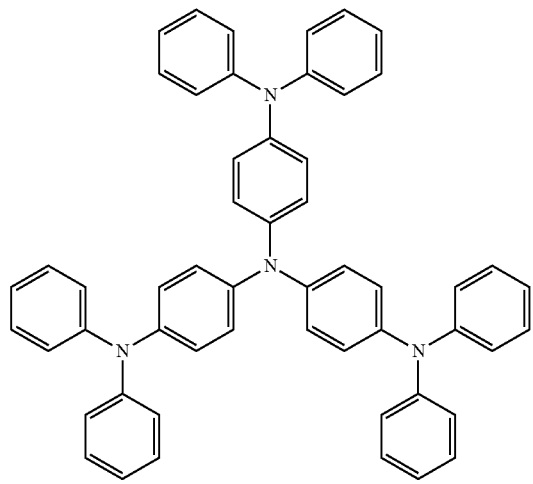
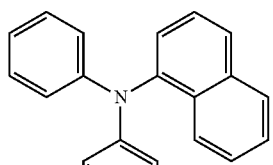
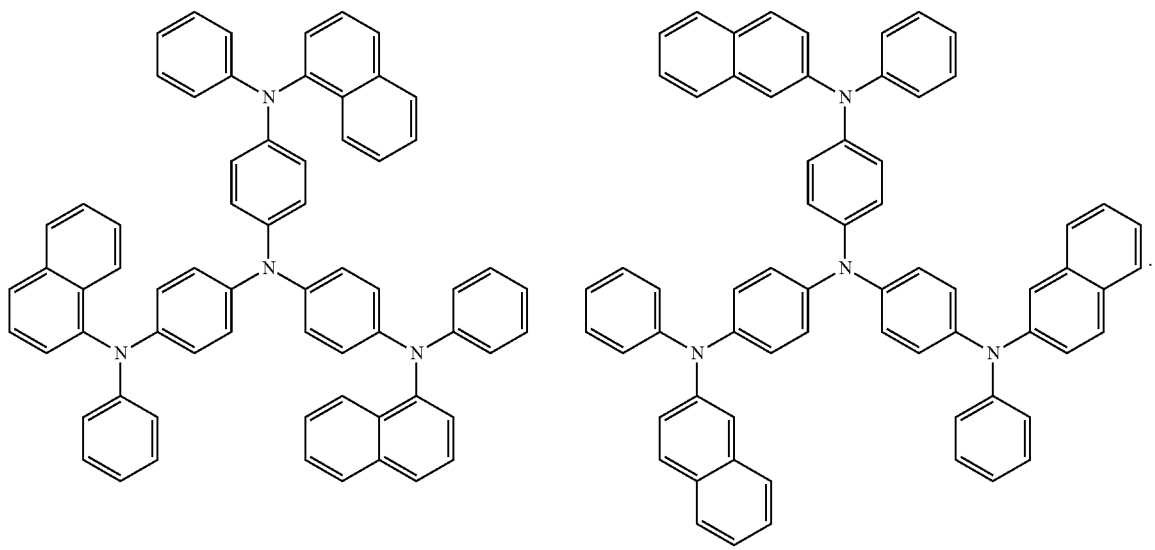

The electron transport region ETR may be provided on the emission layer EML. The electron transport region ETR may include at least one of a hole blocking layer, an electron transport layer ETL and an electron injection layer EIL.

For example, the electron transport region ETR may have the structure of a laminated structure from the emission layer EML, of electron transport layer ETL/electron injection layer EIL, or hole blocking layer/electron transport layer ETL/electron injection layer EIL, or a single layer formed by using a mixture of at least two layers.

The electron transport region ETR may be formed by using various methods such as a vacuum deposition method, a spin coating method, a cast method, an LB method, an inkjet printing method, a laser printing method, an LITI method, etc.

When the electron transport region ETR includes the electron transport layer ETL, the electron transport region ETR may include a compound represented by the following Chemical Formula 1.

[Chemical Formula 1]

In Chemical Formula 1, $X_1$ and $X_2$ may each independently be $CR_5$ or N. $R_1$ to $R_5$ may each independently be selected from, e.g., hydrogen, deuterium, an alkyl group having 1 to 40 carbon atoms, an aryl group having 6 to 40 carbon atoms, a heteroaryl group having 1 to 40 carbon atoms, an aryloxy group having 6 to 40 carbon atoms, an alkyloxy group having 1 to 40 carbon atoms, an arylamino group having 6 to 40 carbon atoms, a diarylamino group having 12 to 40 carbon atoms, an arylalkyl group having 7 to 40 carbon atoms, a cycloalkyl group having 3 to 40 carbon atoms and a heterocycloalkyl group having 3 to 40 carbon atoms, or a group forming a fused aliphatic ring, a fused aromatic ring, a fused heteroaliphatic ring or a fused heteroaromatic ring with an adjacent group, a halogen group or a combination thereof. L may be selected from or include, e.g., a direct linkage, a substituted or unsubstituted aryl group having 6 to 30 carbon atoms, a substituted or unsubstituted fused aryl group having 10 to 30 carbon atoms, a substituted or unsubstituted heteroaryl group including 1 to 30 carbon atoms and N, S or O, and a substituted or unsubstituted fused heteroarylene group having 1 to 30 carbon atoms and N, S or O.

In an implementation, L may include, e.g., an aryl group, a fused aryl group, a heteroaryl group or a condensed heteroarylene group substituted with at least one substituent selected from, e.g., an alkyl group, a hydroxyl group, a cyano group, an alkoxy group, a halogen group, a carboxyl group, an alkoxycarbonyl group, a thionyl group, a thiol group, and a sulfone group.

Het may be or may include, e.g., a substituted or unsubstituted heteroaryl group having 3 to 20 carbon atoms and N. $A_1$ and $Ar_2$ may each independently be selected from or include, e.g., hydrogen, a substituted or unsubstituted aryl group having 6 to 40 carbon atoms or a substituted or unsubstituted heteroaryl group having 1 to 40 carbon atoms.

The electron transport region ETR may include at least one of the following Compounds 1 to 18. For example, the compound represented by Chemical Formula 1 may include one of the following Compounds 1 to 18.

1

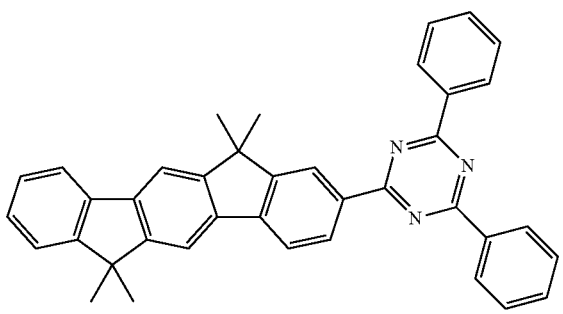

2

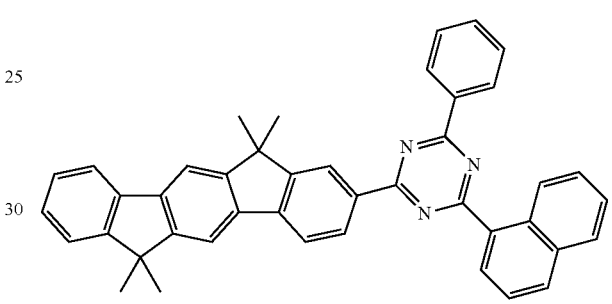

3

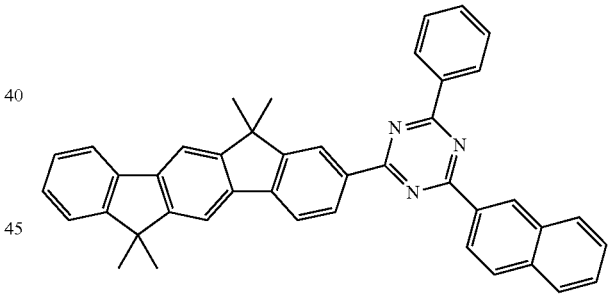

4

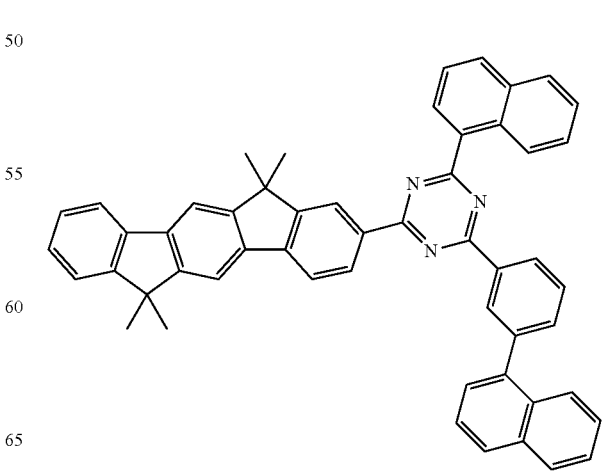

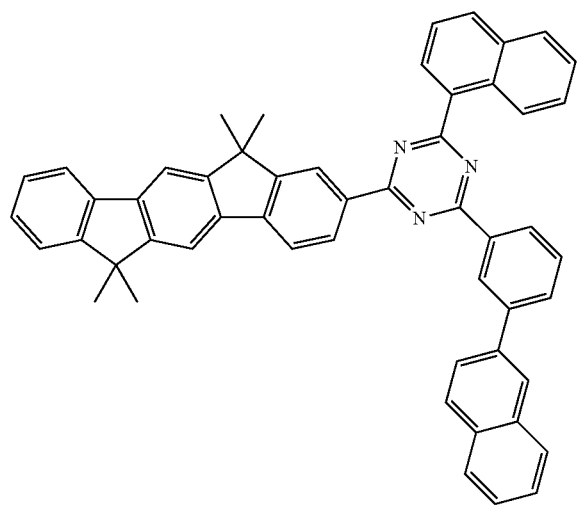
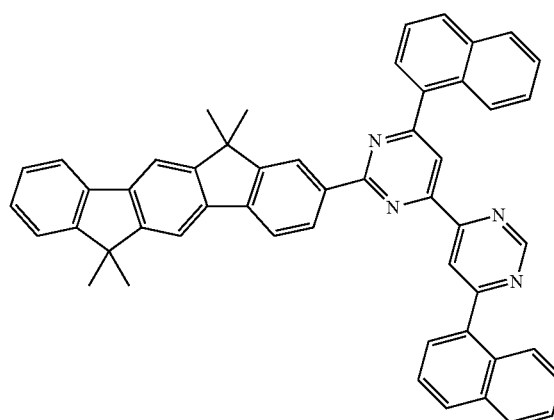
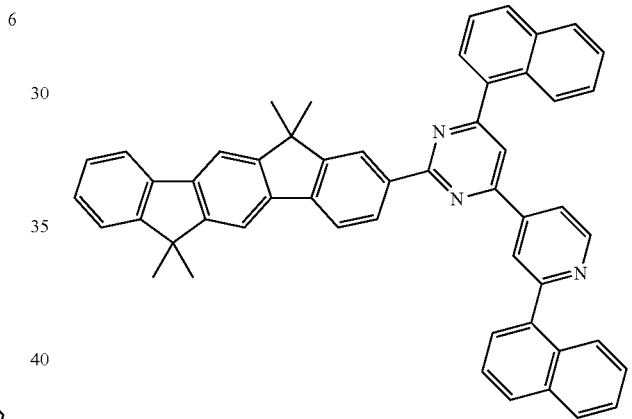
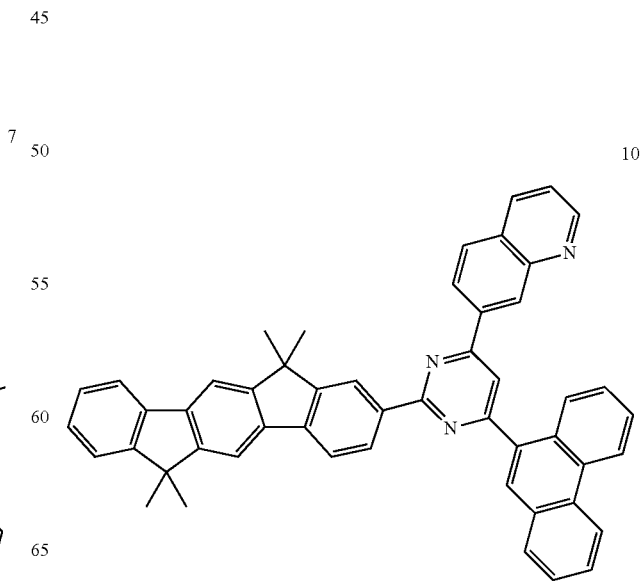

11
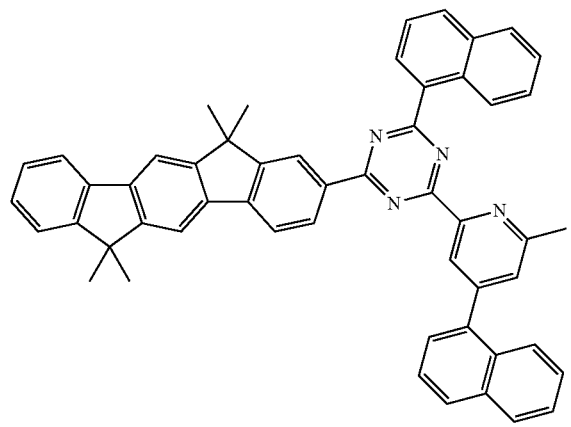
12
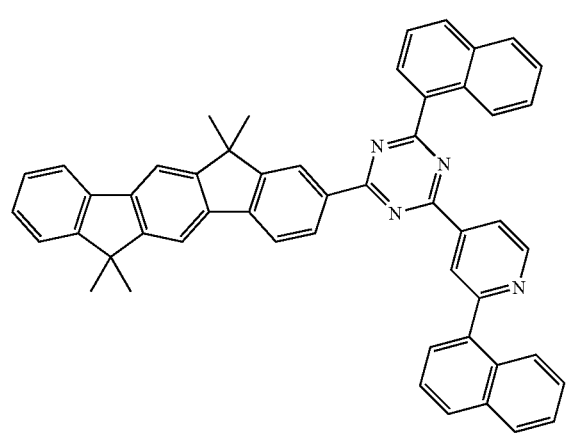
13
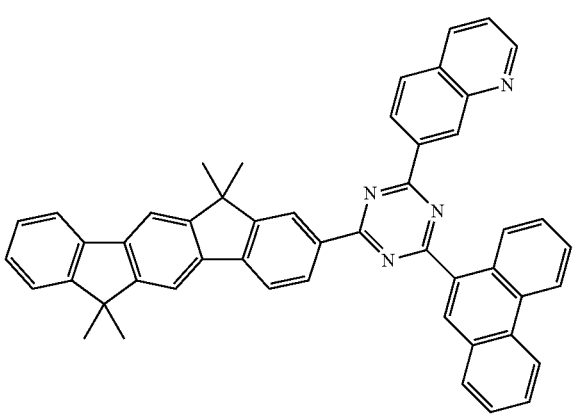
14
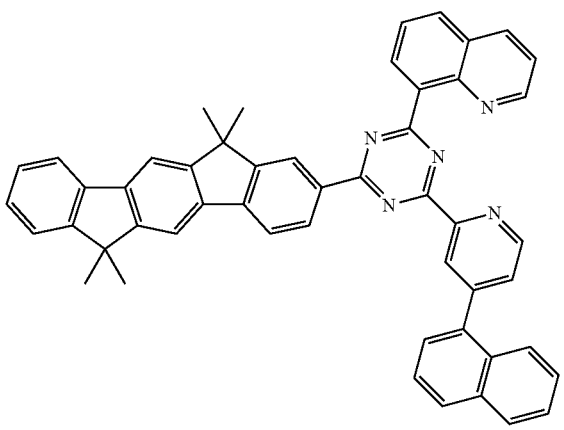
15
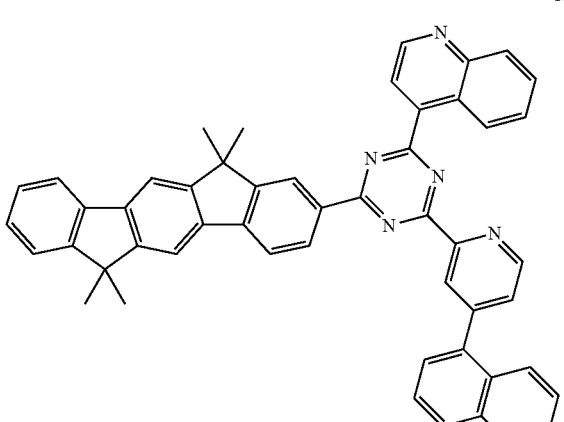
16
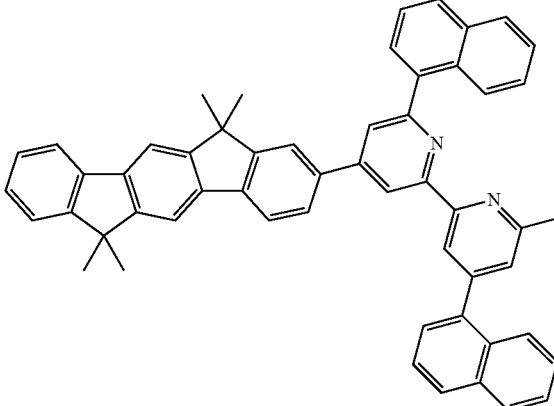

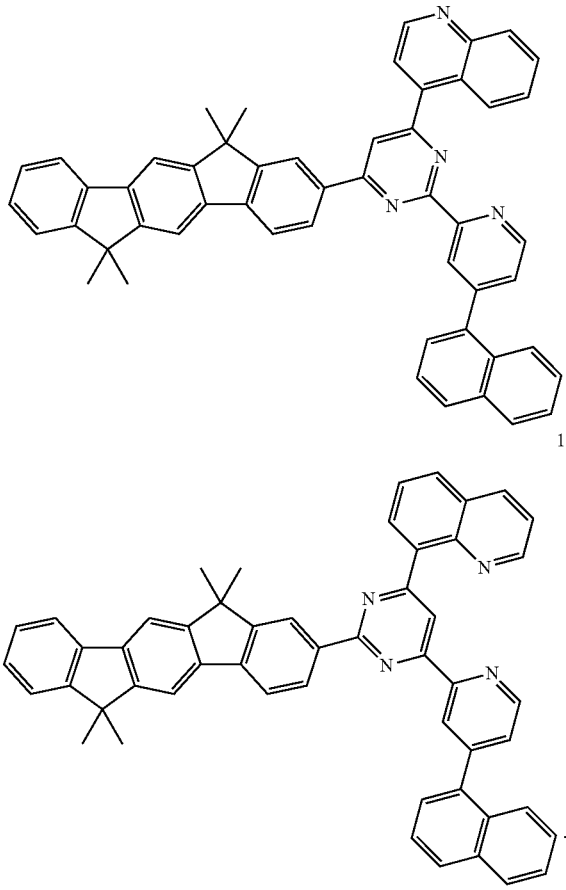

A thickness of the electron transport layer ETL may be from about 100 Å to about 1,000 Å, e.g., from about 150 Å to about 500 Å. When the thickness of the electron transport layer ETL satisfies the above described range, satisfactory electron transport properties may be obtained without inducing substantial increase of a driving voltage.

When the electron transport region ETR includes the electron injection layer EIL, the electron transport region ETR may include a metal compound, e.g., LiF, lithium quinolate (LiQ), $Li_2O$, BaO, NaCl, CsF, and Yb or a metal halide such as RbCl and RbI. The electron injection layer EIL also may be formed using a mixture material of an electron transport material and an insulating organo metal salt. The organo metal salt may be a material having an energy band gap of more than about 4 eV. In an implementation, the organo metal salt may include, e.g., a metal acetate, a metal benzoate, a metal acetoacetate, a metal acetylacetonate or a metal stearate.

A thickness of the electron injection layer EIL may be from about 1 Å to about 100 Å, e.g., about 3 Å to about 90 Å. When the thickness of the electron injection layer EIL satisfies the above described range, satisfactory electron injection properties may be obtained without inducing the substantial increase of a driving voltage.

The electron transport region ETR may include a hole blocking layer, as described above. The hole blocking layer may include, for example, at least one of 2,9-dimethyl-4,7-diphenyl-1,10-phenanthroline (BCP) and 4,7-diphenyl-1,10-phenanthroline (Bphen). The thickness of the hole blocking layer may be from about 20 Å to about 1,000 Å, e.g., from about 30 Å to about 300 Å. When the thickness of the hole blocking layer satisfies the above described range, satisfactory electron injection properties may be obtained without inducing the substantial increase of a driving voltage.

The second electrode EL2 is provided on the electron transport region ETR. The second electrode EL2 may be a common electrode or a cathode. The second electrode EL2 may be a transmissive type electrode, a transflective type electrode or a reflective type electrode.

When the second electrode EL2 is the transmissive type electrode, the second electrode EL2 may include Li, Ca, LiF/Ca, LiF/Al, Al, Mg, BaF, Ba, Ag, a compound thereof or a mixture thereof (e.g., a mixture of Ag and Mg).

The second electrode EL2 may include an auxiliary electrode. The auxiliary electrode may include a layer formed by depositing the above-described material toward an emission layer and a transparent metal oxide on the layer, for example, ITO, IZO, ZnO, ITZO, Mo, Ti, etc.

When the second electrode EL2 is the transflective type electrode or the reflective type electrode, the second electrode EL2 may include Ag, Mg, Al, Pt, Pd, Au, Ni, Nd, Ir, Cr, Li, Ca, LiF/Ca, LiF/Al, Mo, Ti, a compound thereof or a mixture thereof (e.g., a mixture of Ag and Mg). The second electrode El2 may be a reflective layer or a transflective layer formed using the above materials and a multilayered structure including a transparent conductive layer formed using ITO, IZO, ZnO, ITZO, etc.

In the organic light emitting device OEL according to an embodiment, according to the application of a voltage to the first electrode EL1 and the second electrode EL2, respectively, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light is emitted during the transition of the excitons from an excited state to a ground state The organic light emitting device according to an embodiment may include an electron transport region containing a compound represented by the above Chemical Formula 1. The organic light emitting device according to an embodiment may include an emission layer containing a compound represented by the above Chemical Formula 2. Thus, the band gap between the energy band of the hole transport region and the energy band of the emission layer may be decreased, and the hole injection to the emission layer may be facilitated in the organic light emitting device. In addition, the band gap between the energy band of the emission layer and the energy band of the electron transport region may be decreased, and the electron injection into the emission layer may be facilitated. Accordingly, the organic light emitting device according to an embodiment may realize high efficiency and long life.

Hereinafter, a display device according to an embodiment will be explained. The explanation will be concentrated on different points from the organic light emitting device OEL according to the embodiment described above, and unexplained parts will follow the explanation on the organic light emitting device OEL according to an embodiment described above.

Figure 3:
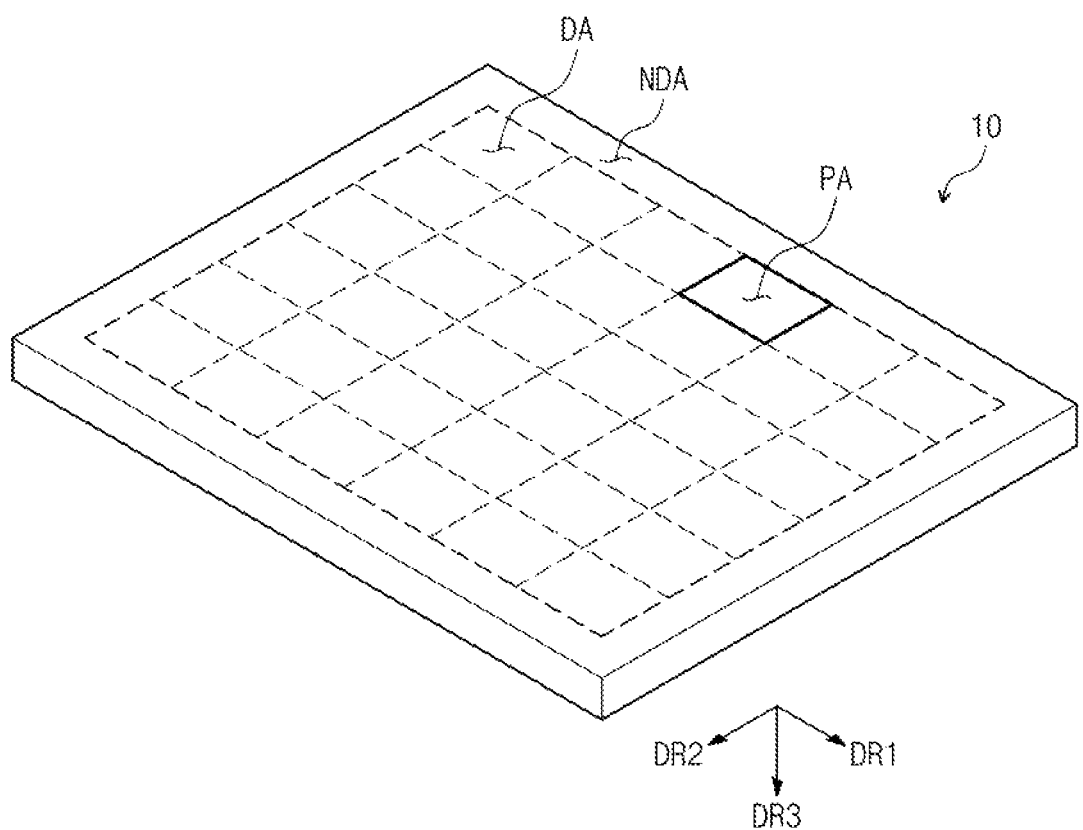
FIG. 3 illustrates a perspective view of an organic light emitting display according to an embodiment.

FIG. 3 illustrates a perspective view of a display device according to an embodiment.

Referring to FIG. 3, a display device 10 according to an embodiment may include a display area DA and a non-display area NDA.

The display area DA displays an image. When seen from the direction of the thickness of the display device 10 (for example, in DR3), the display area DA may have approximately a rectangle shape.

The display area DA may include a plurality of pixel areas PA. The pixel areas PA may be disposed in a matrix shape. The pixel areas PA may be defined by a pixel defining layer (PDL in FIG. 6). Pixel areas PA may include a plurality of pixels (PX in FIG. 4), respectively.

A non-display area NDA may not display an image. When seen from the direction of the thickness of the display device 10 (in DR3), the non-display area NDA may surround, e.g., the display area DA. The non-display area NDA may be adjacent to the display area DA in a first direction (for example, in DR1) and a second direction (for example, in DR2) which is perpendicular to the first direction (for example, DR1).

Figure 4:
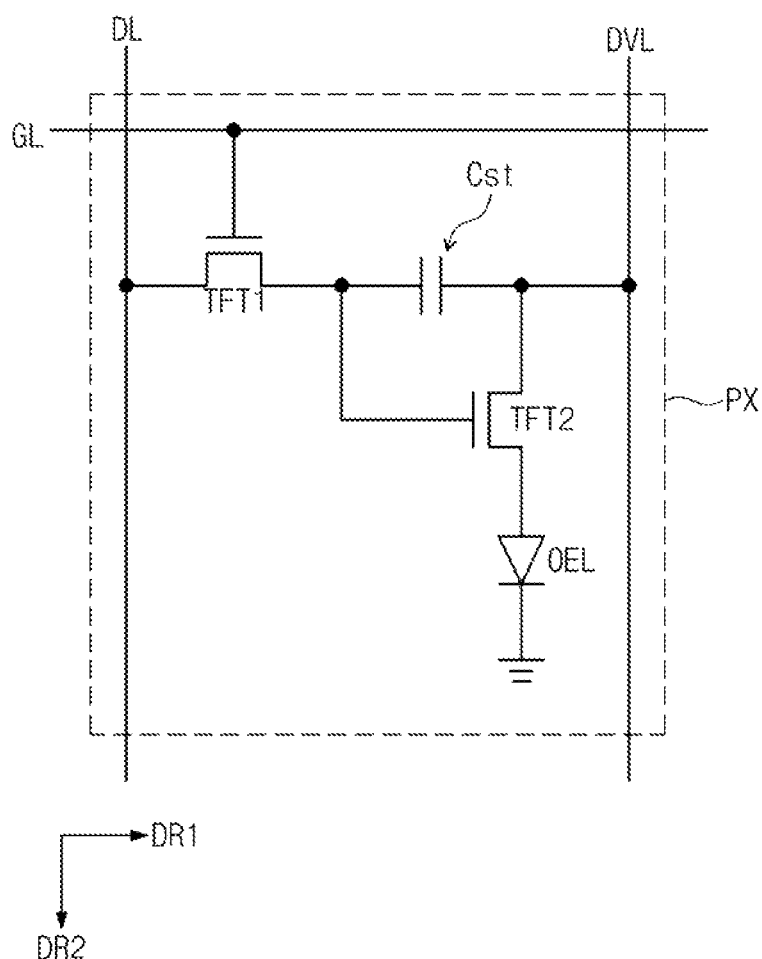
FIG. 4 illustrates a circuit diagram of a pixel included in a display device according to an embodiment.

FIG. 4 illustrates a circuit diagram of a pixel included in the display device according to an embodiment.

Figure 5:
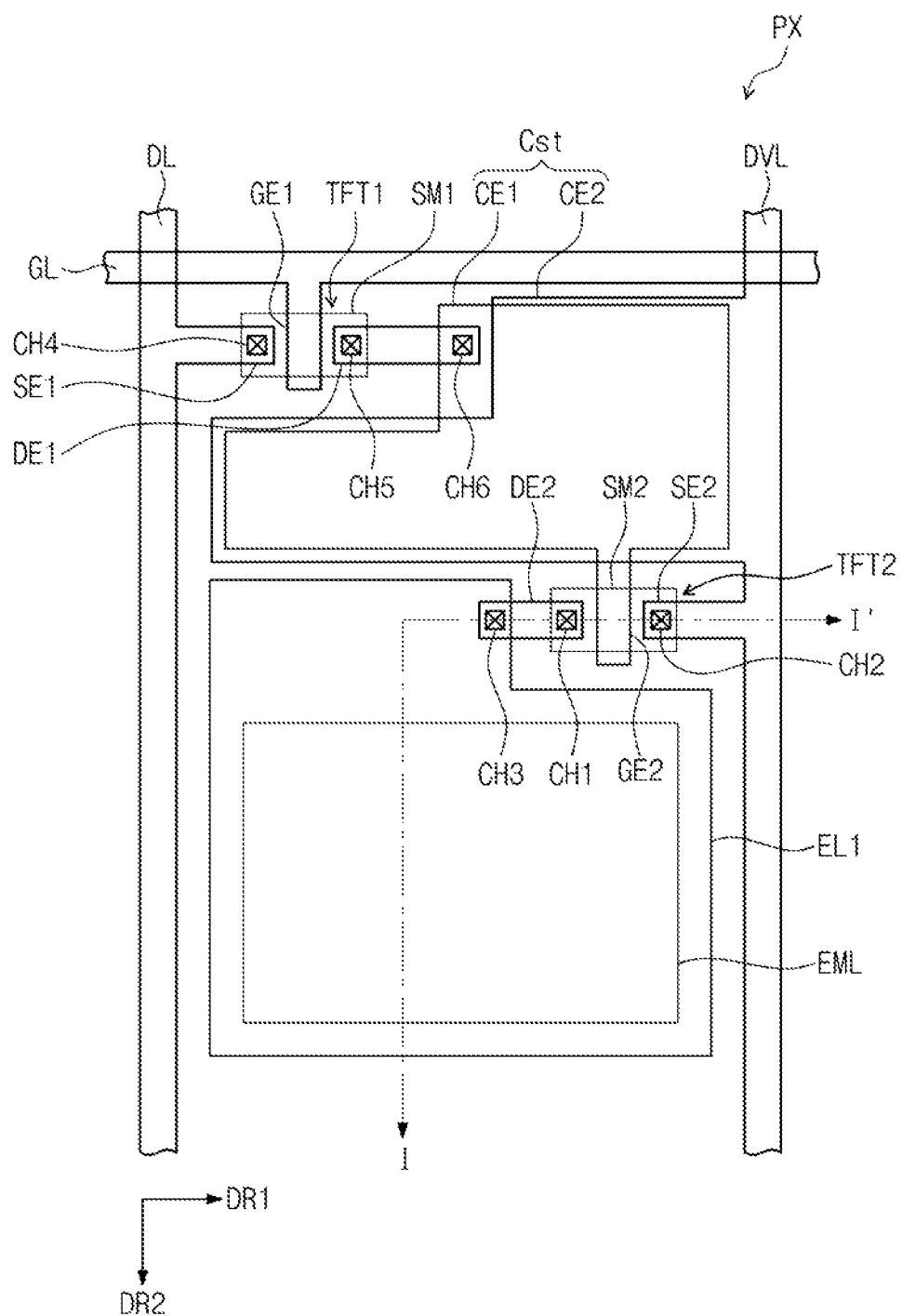
FIG. 5 illustrates a plan view of a pixel included in a display device according to an embodiment.

FIG. 5 illustrates a plan view of a pixel included in the display device according to an embodiment.

Figure 6:
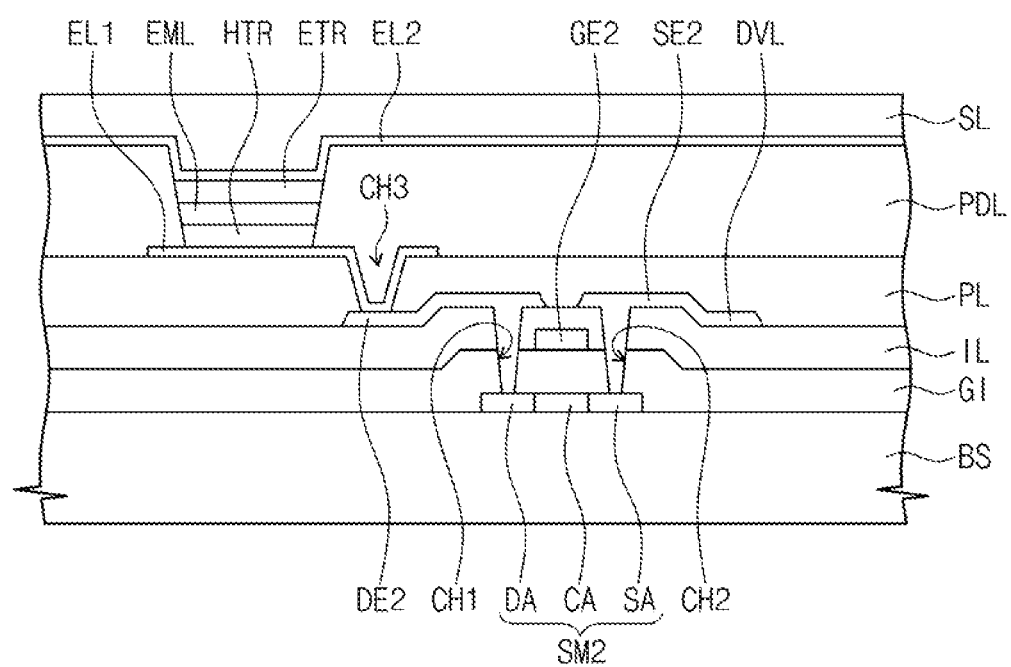
FIG. 6 illustrates a schematic cross-sectional view taken along line I-I' in FIG. 5.

FIG. 6 illustrates a schematic cross-sectional view taken along line I-I' in FIG. 5.

Referring to FIGS. 4 to 6, each pixel PX may include a wire part including a gate line GL, a data line DL and a driving voltage line DVL, thin film transistors TFT1 and TFT2 connected to the wire part, an organic light emitting device OEL connected to the thin film transistors TFT1 and TFT2, and a capacitor Cst.

Each pixel PX may emit light having a specific color, for example, one of red light, green light and blue light. The kind of color light is not limited thereto, and may further include, for example, cyan light, magenta light, yellow light, etc.

The gate line GL is extended in the first direction DR1. The data line DL is extended in the second direction DR2 crossing the gate line GL. The driving voltage line DVL is extended in substantially the same direction as the data line DL, i.e., the second direction DR2. The gate line GL transmits scanning signals to the thin film transistors TFT1 and TFT2, and the data line DL transmits data signals to the thin film transistors TFT1 and TFT2, and the driving voltage line DVL provides a driving voltage to the thin film transistors.

The thin film transistors TFT1 and TFT2 may include a driving thin film transistor TFT2 for controlling the organic light emitting device OEL and a switching thin film transistor TFT1 for switching the driving thin film transistor TFT2. In an embodiment, each pixel PX includes two thin film transistors TFT1 and TFT2. Each pixel PX may include one thin film transistor and one capacitor, or each pixel PX may include at least three thin film transistors and at least two capacitors.

The switching thin film transistor TFT1 includes a first gate electrode GE1, a first source electrode SE1 and a first drain electrode DE1. The first gate electrode GE1 is connected to the gate line GL, and the first source electrode SE1 is connected to the data line DL. The first drain electrode DE1 is connected to a first common electrode CE1 via a fifth contact hole CH5. The switching thin film transistor TFT1 transmits data signals applied to the data line DL to the driving thin film transistor TFT2 according to scanning signals applied to the gate line GL.

The driving thin film transistor TFT2 includes a second gate electrode GE2, a second source electrode SE2 and a second drain electrode DE2. The second gate electrode GE2 is connected to the first common electrode CE1. The second source electrode SE2 is connected to the driving voltage line DVL. The second drain electrode DE2 is connected to the first electrode EL1 by a third contact hole CH3.

The first electrode EL1 is connected to a second drain electrode DE2 of the driving thin film transistor TFT2. To the second electrode EL2, a common voltage is applied, and the emission layer EML emits blue light according to the output signals of the driving thin film transistor TFT2, thereby displaying images. The first electrode EL1 and the second electrode EL2 will be described in particular herein below.

The capacitor Cst is connected between the second gate electrode GE2 and the second source electrode SE2 of the driving thin film transistor TFT2 and charges and maintains data signals inputted to the second gate electrode GE2 of the driving thin film transistor TFT2. The capacitor Cst may include the first common electrode CE1 connected to the first drain electrode DE1 via a sixth contact hole CH6 and a second common electrode CE2 connected to the driving voltage line DVL.

Referring to FIGS. 5 and 6, the display device 10 according to an embodiment includes a base substrate BS on which a thin film transistor and the organic light emitting device OEL are laminated. Any commonly used base substrates may be used as the base substrate BS, and may be formed using an insulating material, for example, glass, plastics, quartz, etc. As an organic polymer forming the base substrate BS, polyethylene terephthalate (PET), polyethylene naphthalate (PEN), polyimide, polyethersulfone, etc. may be used. The base substrate BS may be selected in consideration of mechanical strength, thermal stability, transparency, surface smoothness, easiness of handling, water-proof properties, etc.

On the base substrate BS, a substrate buffer layer (not shown) may be provided. The substrate buffer layer (not shown) prevents the diffusion of impurities into the switching thin film transistor TFT1 and the driving thin film transistor TFT2. The substrate buffer layer (not shown) may be formed using silicon nitrides (SiNx), silicon oxides (SiOx), silicon oxynitrides (SiOxNy), etc., and may be omitted according to the material of the base substrate BS and process conditions.

On the base substrate BS, a first semiconductor layer SM1 and a second semiconductor layer SM2 are provided. The first semiconductor layer SM1 and the second semiconductor layer SM2 are formed using a semiconductor material and function as an active layer of a switching thin film transistor TFT1 and a driving thin film transistor TFT2, respectively. Each of the first semiconductor layer SM1 and the second semiconductor layer SM2 includes a source area SA, a drain area DA and a channel area CA provided between the source area SA and the drain area DA. Each of the first semiconductor layer SM1 and the second semiconductor layer SM2 may be formed by selecting an inorganic semiconductor or an organic semiconductor, respectively. The source area SA and the drain area DA may be doped with n-type impurities or p-type impurities.

On the first semiconductor layer SM1 and the second semiconductor layer SM2, a gate insulating layer GI is provided. The gate insulating layer GI covers the first semiconductor layer SM1 and the second semiconductor layer SM2. The gate insulating layer GI may be formed using an organic insulating material or an inorganic insulating material.

On the gate insulating layer GI, a first gate electrode GE1 and a second gate electrode GE2 are provided. Each of the first gate electrode GE1 and the second gate electrode GE2 are formed to cover a corresponding area in the channel area CA of the first semiconductor layer SM1 and the second semiconductor layer SM2.

On the first gate electrode GE1 and the second gate electrode GE2, an insulating interlayer IL is provided. The insulating interlayer IL covers the first gate electrode GE1 and the second gate electrode GE2. The insulating interlayer IL may be formed using an organic insulating material or an inorganic insulating material.

On the insulating interlayer IL, a first source electrode SE1, a first drain electrode DE1, a second source electrode SE2 and a second drain electrode DE2 are provided. The second drain electrode DE2 makes a contact with the drain area DA of the second semiconductor layer SM2 via a first contact hole CH1 formed in a gate insulating layer GI and the insulating interlayer IL, and the second source electrode SE2 makes a contact with the source area SA of a second semiconductor layer SM2 via a second contact hole CH2 formed in the gate insulating layer GI and the insulating interlayer IL. The first source electrode SE1 makes a contact with the source area (not shown) of the first semiconductor layer SM1 via a fourth contact hole CH4 formed in the gate insulating layer GI and the insulating interlayer IL, and the first drain electrode DE1 makes a contact with the drain area (not shown) of the first semiconductor layer SM1 via a fifth contact hole CH5 formed in the gate insulating layer GI and the insulating interlayer IL.

On the first source electrode SE1 and the first drain electrode DE1, and the second source electrode SE2 and the second drain electrode DE2, a passivation layer PL is provided. The passivation layer PL may play the role of the switching thin film transistor TFT1 and the driving thin film transistor TFT2, or the role of a planarization layer for planarizing the top surface thereof.

On the passivation layer PL, a first electrode EL1 is provided. The first electrode EL1 may be, for example, an anode. The first electrode EL1 is connected to the second drain electrode DE2 of the driving thin film transistorTR2 via the third contact hole CH3 formed in the passivation layer PL.

On the passivation layer PL, a pixel defining layer PDL for partitioning pixel areas (PA in FIG. 3) corresponding to each of the pixels PX is provided. The pixel defining layer PDL exposes the top surface of the first electrode EL1 and is extruded from the base substrate BS along the circumference of each pixel PX. The pixel defining layer PDL may include a metal-fluoride ion compound, without limitation. For example, the pixel defining layer PDL may be formed using one metal-fluoride ion compound of LiF, $BaF_2$ and CsF. When the metal-fluoride ion compound has a certain thickness, insulating properties may be obtained. The thickness of the pixel defining layer PDL may be, for example, from about 10 nm to about 100 nm.

To each pixel area (PA in FIG. 3) surrounded by the pixel defining layer PDL, an organic light emitting device OEL is provided. The organic light emitting device OEL includes a first electrode EL1, a hole transport region HTR, an emission layer EML, an electron transport region ETR and a second electrode EL2.

The first electrode EL1 may have conductivity. The first electrode EL1 may be a pixel electrode or an anode. The first electrode EL1 may be formed as a transmissive type electrode, a transflective type electrode or a reflective type electrode. When the first electrode EL1 is formed as the transmissive type electrode, the first electrode EL1 may be formed using a transparent metal oxide, for example, ITO, IZO, ZnO, ITZO, etc. When the first electrode EL1 is formed as the transflective type electrode or the reflective type electrode, the first electrode EL1 may include Ag, Mg, Al, Pt, Pd, Au, Ni, Nd, Ir, Cr or a mixture of metals.

On the first electrode EL1, an organic layer may be disposed. The organic layer includes the emission layer EML. The organic layer may further include the hole transport region HTR and the electron transport region ETR.

The hole transport region HTR is provided on the first electrode EL1. The hole transport region HTR may include at least one of a hole injection layer HIL, a hole transport layer HTL, a buffer layer, and an electron blocking layer.

The hole transport region HTR may have a single layer formed by using a single material, a single layer formed by using a plurality of different materials or a multilayered structure including a plurality of layers formed by using a plurality of different materials.

For example, the hole transport region HTR may have the structure of a single layer formed by using a plurality of different materials, or a laminated structure from the first electrode EL1, of hole injection layer HIL/hole transport layer HTL, hole injection layer HIL/hole transport layer HTL/buffer layer, hole injection layer HIL/buffer layer, hole transport layer HTL/buffer layer or hole injection layer HIL/hole transport layer HTL/electron blocking layer.

The hole transport region HTR may be formed by using various methods such as a vacuum deposition method, a spin coating method, a cast method, an LB method, an inkjet printing method, a laser printing method, an LITI method, etc.

When the hole transport region HTR includes the hole injection layer HIL, the hole transport region HTR may include a phthalocyanine such as copper phthalocyanine, DNTPD, m-MTDATA, TDATA, 2-TNATA, PEDOT/PSS, PANI/DBSA, PANI/CSA, PANI/PSS.

When the hole transport region HTR includes the hole transport layer HTL, the hole transport region HTR may include a carbazole derivative such as N-phenylcarbazole and polyvinyl carbazole, a fluorine-based derivative, TPD, a triphenylamine-based derivative such as TCTA, NPB, TAPC, etc.

The thickness of the hole transport region HTR may be from about 100 Å to about 10,000 Å, e.g., from about 100 Å to about 1,000 Å. When the hole transport region HTR includes both the hole injection layer HIL and the hole transport layer HTL, the thickness of the hole injection layer HIL may be from about 100 Å to about 10,000 Å, e.g., from about 100 Å to about 1,000 Å, and the thickness of the hole transport layer HTL may be from about 50 Å to about 2,000 Å, e.g., from about 100 Å to about 1,500 Å. When the thicknesses of the hole transport region HTR, the hole injection layer HIL and the hole transport layer HTL satisfy the above-described ranges, satisfactory hole transport properties may be obtained without substantial increase of a driving voltage.

The hole transport region HTR may further include a charge generating material other than the above-described materials to improve conductivity. The charge generating material may be dispersed in the hole transport region HTR uniformly or non-uniformly. The charge generating material may be, for example, p-dopant. The p-dopant may be one of a quinone derivative, a metal oxide and a cyano group-containing compound, without limitation. Examples of the p-dopant may include a quinone derivative such as TCNQ, F4-TCNQ, etc., a metal oxide such as tungsten oxide, molybdenum oxide, etc.

As described above, the hole transport region HTR may further include one of a buffer layer and an electron blocking layer other than the hole injection layer HIL and the hole transport layer HTL. The buffer layer may compensate an optical resonance range according to the wavelength of light emitted from the emission layer EML and increase light emission efficiency. Materials included in the hole transport region HTR may be used as materials included in the buffer layer. The electron blocking layer is a layer preventing electron injection from the electron transport region ETR to the hole transport region HTR.

The emission layer EML is provided on the hole transport region HTR. The emission layer EML may have a single layer formed by using a single material, a single layer formed by using a plurality of different materials, or a multilayered structure including a plurality of layers formed by using a plurality of layers formed by using a plurality of different materials.

The emission layer EML may be formed by using various methods such as a vacuum deposition method, a spin coating method, a cast method, an LB method, an inkjet printing method, a laser printing method, an LITI method, etc.

The emission layer EML may emit green light. The emission layer EML may be formed using a material emitting green light and may include a phosphorescent material or a fluorescent material. In addition, the emission layer EML may include a host or a dopant.

The host may include a compound represented by the following Chemical Formula 2.

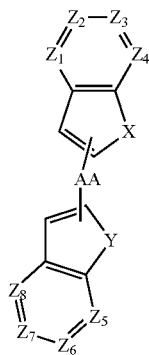

[Chemical Formula 2]

In Chemical Formula 2, AA may be selected from a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms and a heteroaryl group having 1 to 60 carbon atoms. In an implementation, AA may have a structure such that a ring including X and a ring including Y are fused to form a fused aliphatic ring, a fused aromatic ring, a fused heteroaliphatic ring, or a fused heteroaromatic ring.

X may be selected from $N(Ar_3)$, O and S. Y may be selected from $N(Ar_4)$, O and S. $Ar_3$ and $Ar_4$ may each independently be selected from an alkyl group having 1 to 60 carbon atoms, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, and a heteroaryl group having 1 to 60 carbon atoms. $Z_1$ to $Z_8$ may each independently be selected from $C(Ar_5)$ and N. Each $Ar_5$ of $Z_1$ to $Z_8$ may be different from each other. Adjacent ones of $Ar_5$ may be separate or may be combined or bonded to each other to form a ring. Each $Ar_5$ may be independently selected from hydrogen, an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, a heteroaryl group having 1 to 60 carbon atoms, an arylthio group having 6 to 60 carbon atoms, an alkylthio group having 1 to 60 carbon atoms, a mono- or di-alkylamino group having 1 to 60 carbon atoms, a mono-arylamino group having 6 to 30 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group and a hydroxyl group.

In an implementation, the compound represented by Chemical Formula 2 does not include a compound in which X is $N(Ar_3)$, Y is $N(Ar_4)$, both $Ar_3$ and $Ar_4$ are the same, all $Z_1$ to $Z_8$ are $C(Ar_5)$, and $Ar_5$ included in each of $Z_1$ to $Z_8$ are the same.

The alkyl group, the cycloalkyl group, the heterocycloalkyl group, the bicycloalkyl group, the adamantyl group, the alkenyl group, the alkynyl group, the aryl group, the alkoxy group, the aryloxy group, the heteroaryl group, the arylthio group, the alkylthio group, the alkylamino group, the arylamino group, the trialkylsilyl group, the dialkylarylsilyl group, the triarylsilyl group, the arylboranyl group or the alkylboranyl group in $Ar_3$ to $Ar_5$, if substituted, may each independently be substituted with at least one substituent selected from an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, an aryl group having 6 to 60 carbon atoms and substituted with $P(=O)RaRb$ [in which Ra and Rb are independently an alkyl group having 1 to 60 carbon atoms or an aryl group having 6 to 60 carbon atoms], a heteroaryl group having 1 to 60 carbon atoms, a heteroaryl group having 1 to 60 carbon atoms and substituted with an aryl group having 6 to 60 carbon atoms, a heteroaryl group having 1 to 60 carbon atoms and substituted with an alkyl group having 1 to 60 carbon atoms, an aralkyl group having 7 to 120 carbon atoms, an arylthio group having 6 to 60 carbon atoms, an alkylthio group having 1 to 60 carbon atoms, a mono- or di-alkylamino group having 1 to 30 carbon atoms, a mono- or di-arylamino group having 6 to 60 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group, and a hydroxyl group.

In an implementation, the host may include one of the following compounds, in which X, Y, and $Z_1$ to $Z_8$ are defined the same as X, Y, and $Z_1$ to $Z_8$ of Chemical Formula 2.

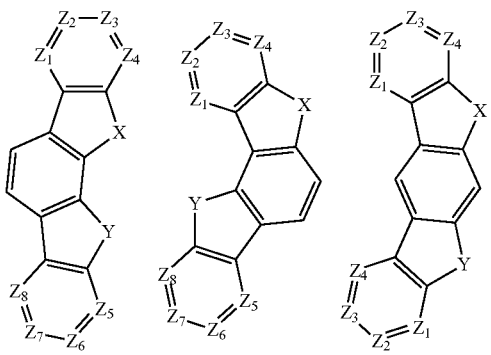

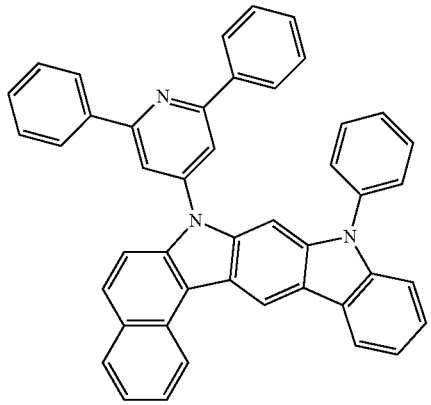

In an implementation, the host may include one of the following Compounds H-1 to H-7.

H-1

H-2

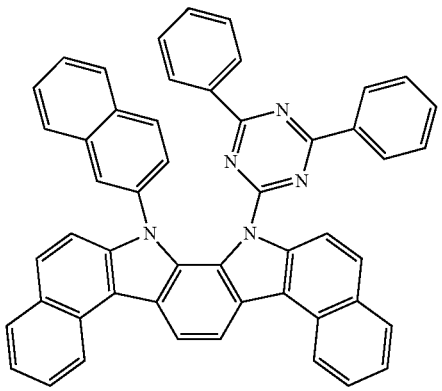

H-3

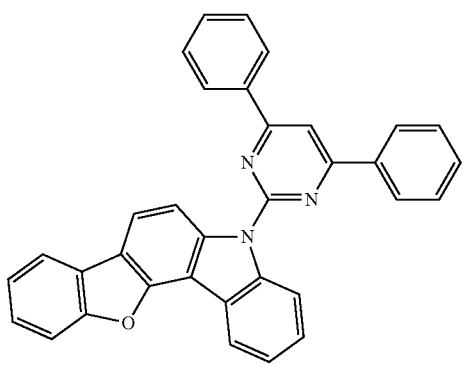

H-4

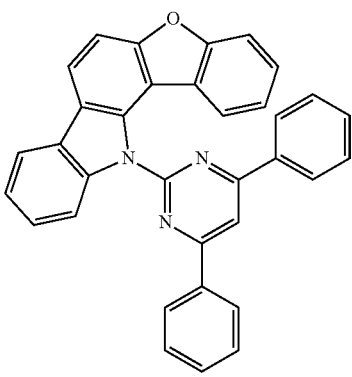

H-5

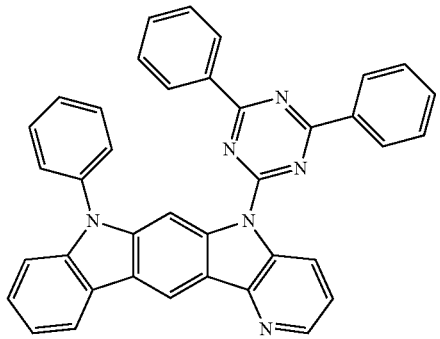

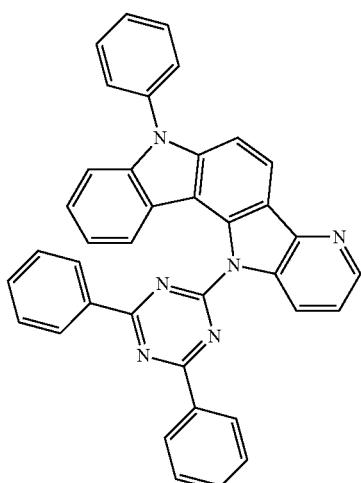
H-6
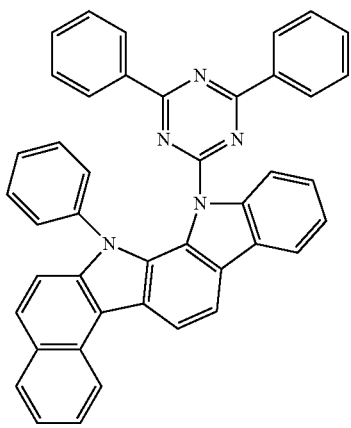
H-7
The emission layer may further include at least one of an arylamine-containing or arylamine-based compound and a styryl arylamine-containing or arylamine-based compound.
In an implementation, the arylamine-containing compound may include at least one of the following compounds.
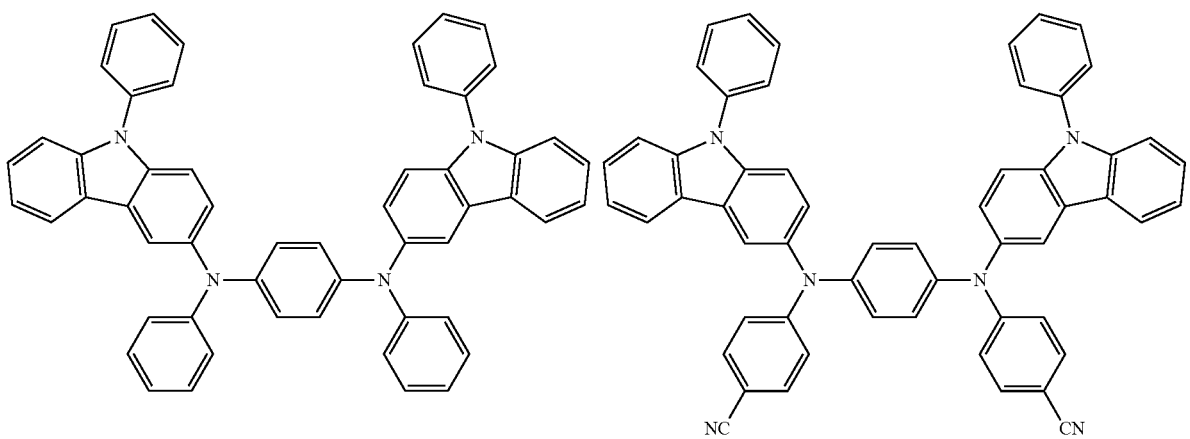
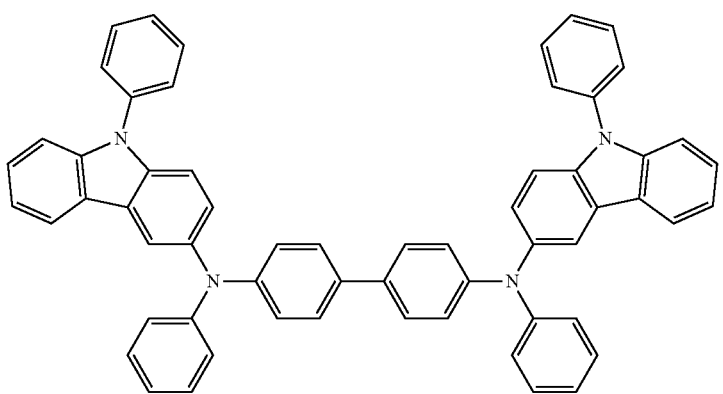

-continued
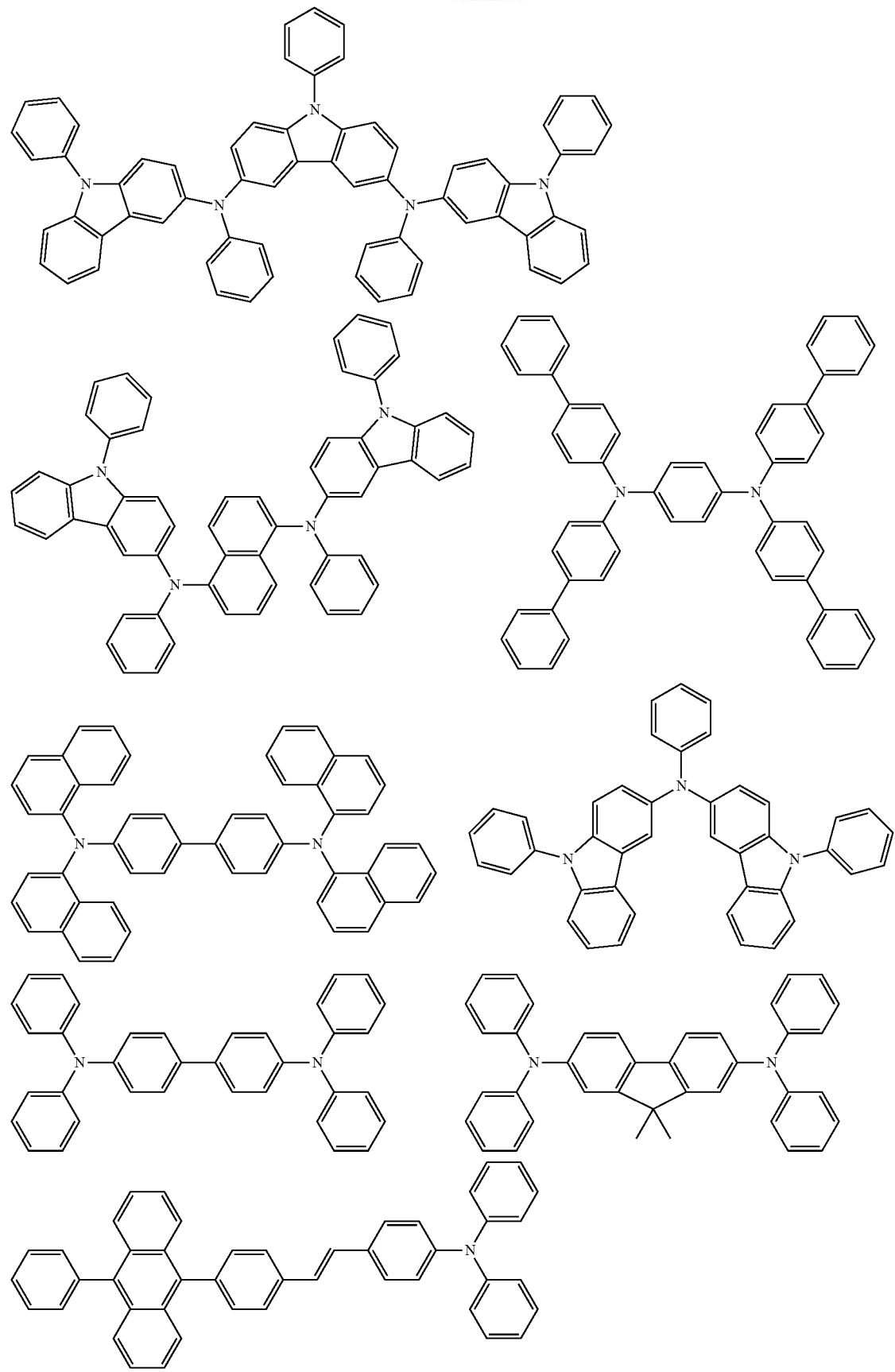

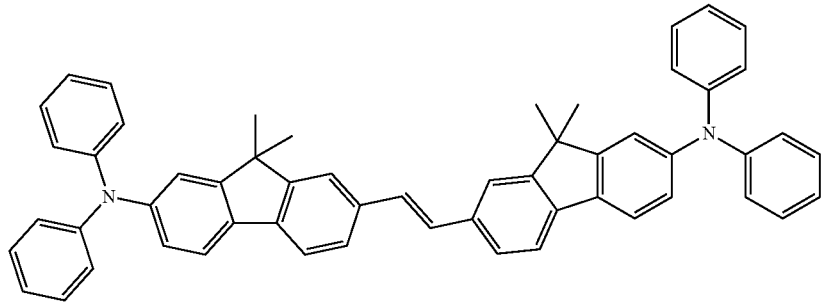
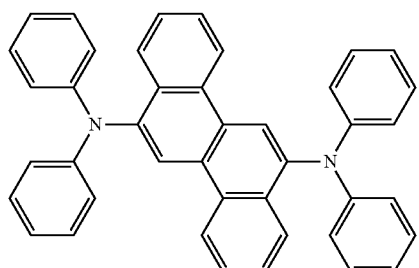
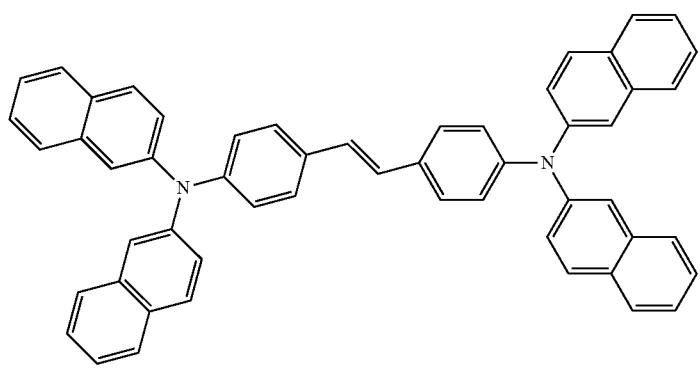
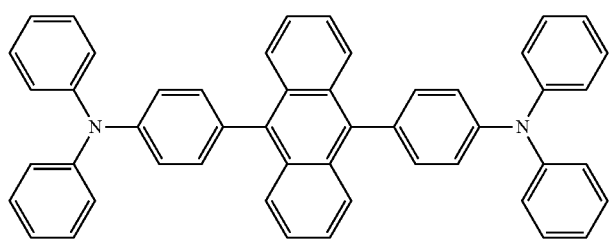
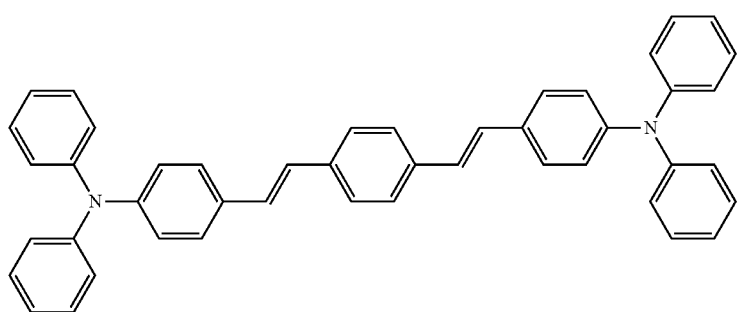

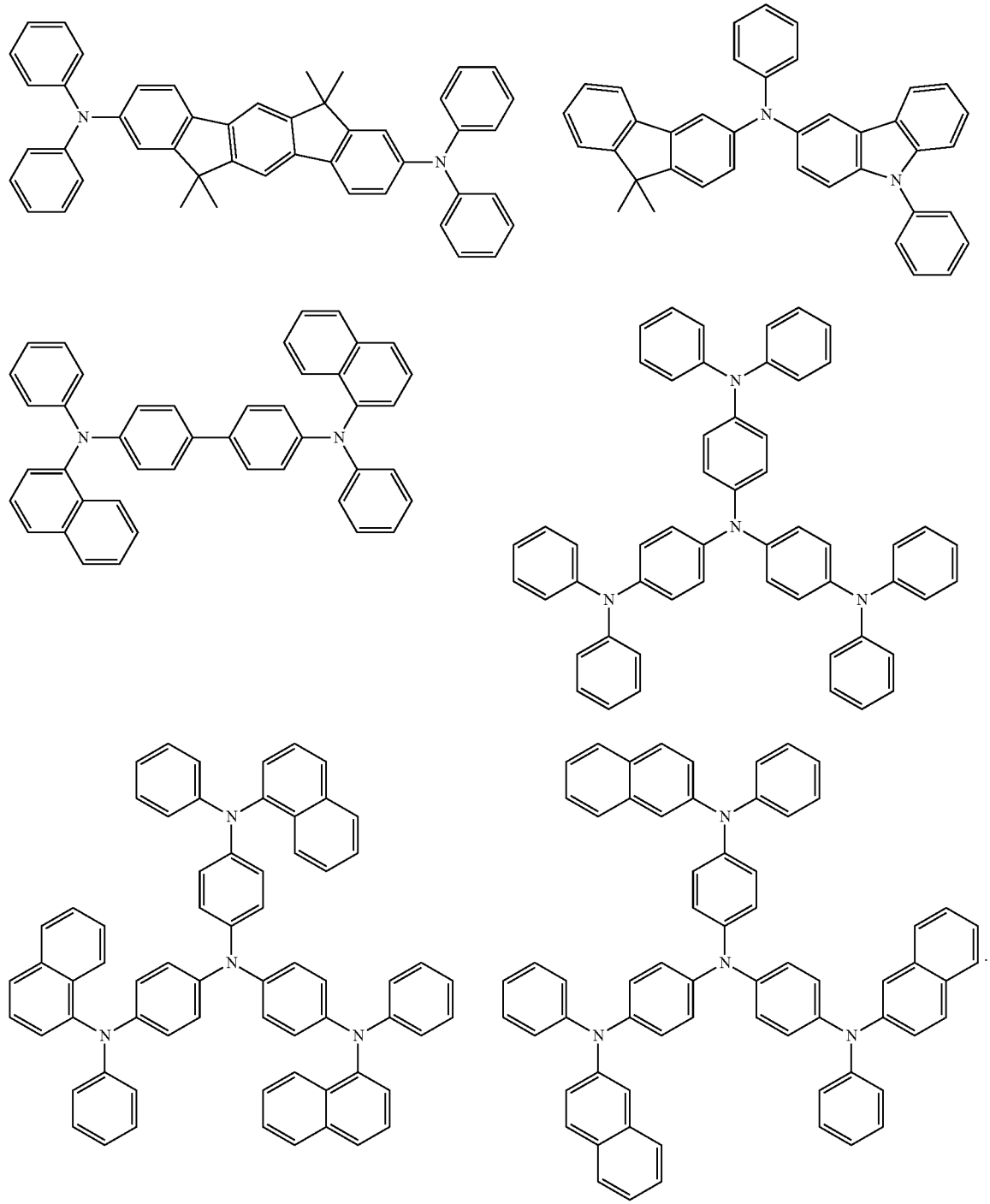

The electron transport region ETR may be provided on the emission layer EML. The electron transport region ETR may include at least one of a hole blocking layer, an electron transport layer ETL and an electron injection layer EIL, without limitation.

For example, the electron transport region ETR may have the structure of a laminated structure from the emission layer EML, of electron transport layer ETL/electron injection layer EIL or hole blocking layer/electron transport layer ETL/electron injection layer EIL, or a single layer formed by using a mixture of at least two layers.

The electron transport region ETR may be formed by using various methods such as a vacuum deposition method, a spin coating method, a cast method, an LB method, an inkjet printing method, a laser printing method, an LITI method, etc.

When the electron transport region ETR includes the electron transport layer ETL, the electron transport region ETR may include a compound represented by the following Chemical Formula 1.

[Chemical Formula 1]

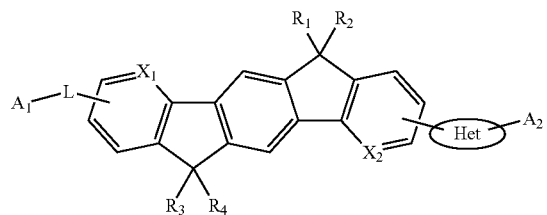

In Chemical Formula 1, $X_1$ and $X_2$ may each independently be $CR_5$ or N. $R_1$ to $R_5$ may each independently be selected from, e.g., hydrogen, deuterium, an alkyl group having 1 to 40 carbon atoms, an aryl group having 6 to 40 carbon atoms, a heteroaryl group having 1 to 40 carbon atoms, an aryloxy group having 6 to 40 carbon atoms, an alkyloxy group having 1 to 40 carbon atoms, an arylamino group having 6 to 40 carbon atoms, a diarylamino group having 12 to 40 carbon atoms, an arylalkyl group having 7 to 40 carbon atoms, a cycloalkyl group having 3 to 40 carbon atoms and a heterocycloalkyl group having 3 to 40 carbon atoms, or a group forming a fused aliphatic ring, a fused aromatic ring, a fused heteroaliphatic ring or a fused heteroaromatic ring with an adjacent group, a halogen group, or a combination thereof. L may be selected from, e.g., a direct linkage, a substituted or unsubstituted aryl group having 6 to 30 carbon atoms, a substituted or unsubstituted fused aryl group having 10 to 30 carbon atoms, a substituted or unsubstituted heteroaryl group including 1 to 30 carbon atoms and N, S or O, and a substituted or unsubstituted fused heteroarylene group having 1 to 30 carbon atoms and N, S or O.

In an implementation, L may be an aryl group, a fused aryl group, a heteroaryl group or a condensed heteroarylene group substituted with at least one substituent selected from, e.g., an alkyl group, a hydroxyl group, a cyano group, an alkoxy group, a halogen group, a carboxyl group, an alkoxycarbonyl group, a thionyl group, a thiol group and a sulfone group.

Het may be or may include, e.g., a substituted or unsubstituted heteroaryl group having 3 to 20 carbon atoms and N. $A_1$ and $Ar_2$ may each independently be or include, e.g., hydrogen, a substituted or unsubstituted aryl group having 6 to 40 carbon atoms or a substituted or unsubstituted heteroaryl group having 1 to 40 carbon atoms.

In an implementation, the electron transport region ETR may include at least one of the following Compounds 1 to 18. For example, the compound represented by Chemical Formula 1 may include one of the following Compounds 1 to 18.

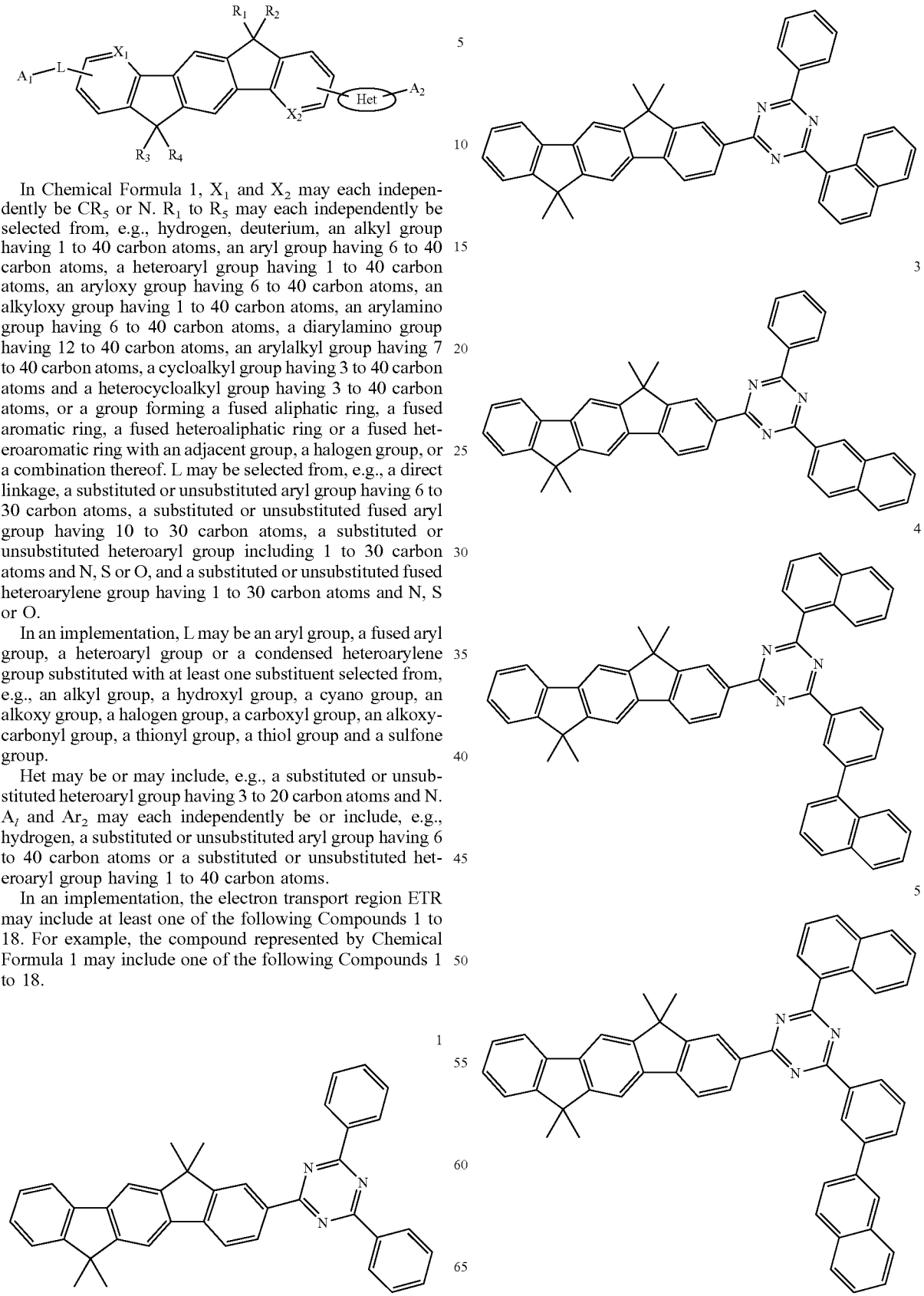

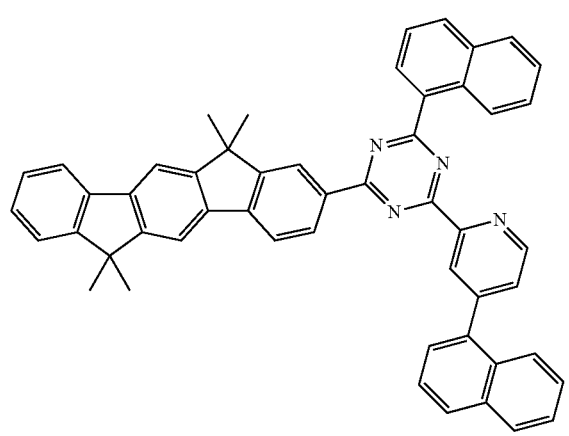
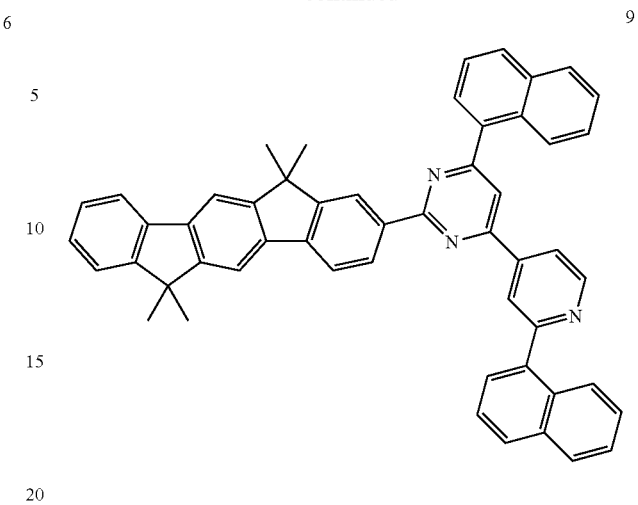
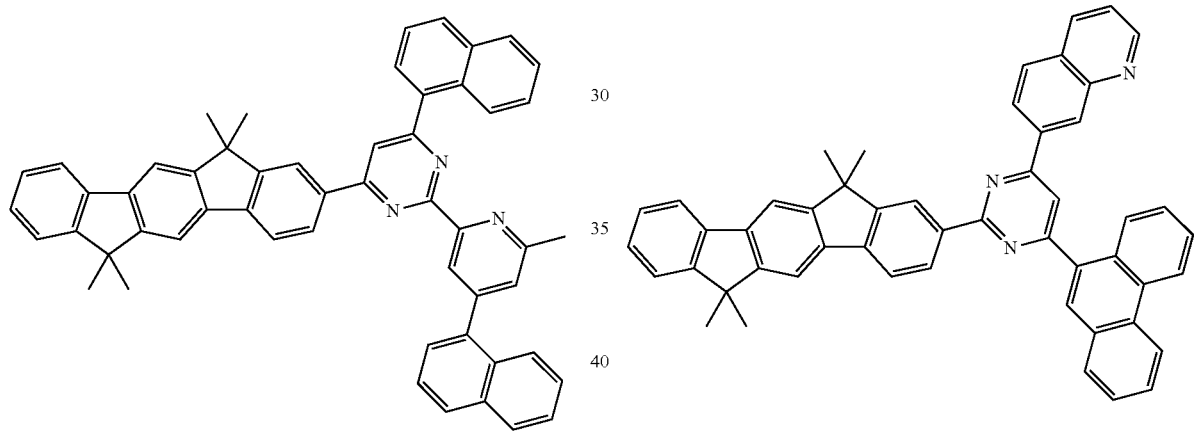
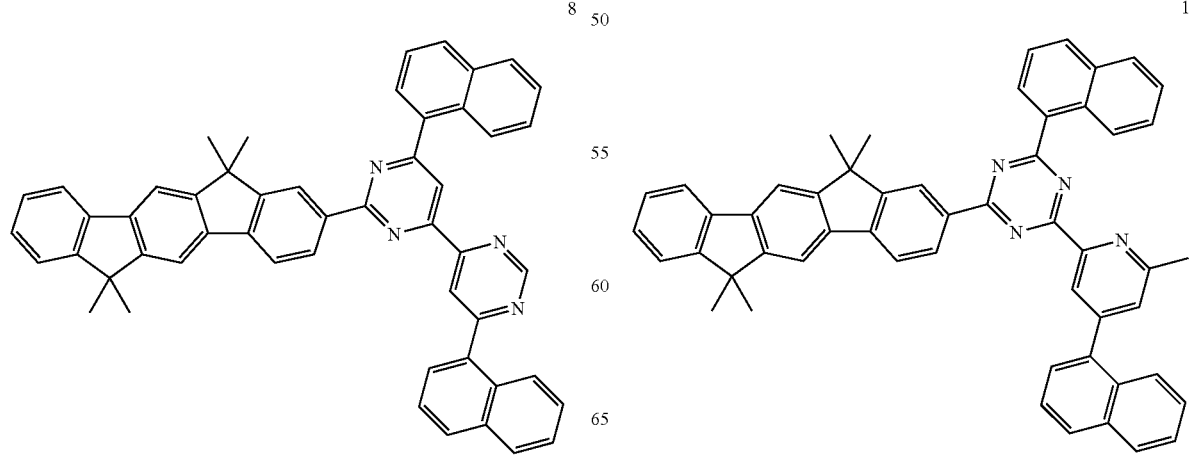

-continued
12
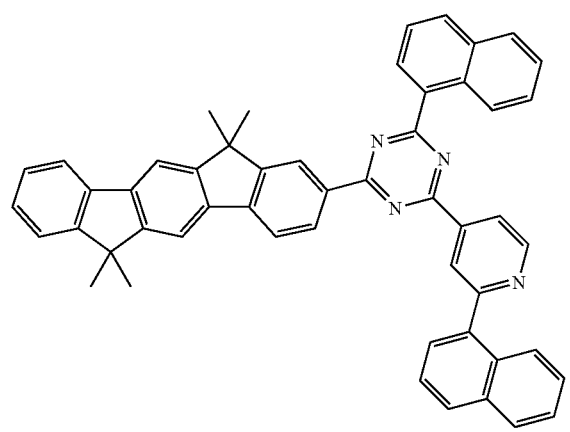
13
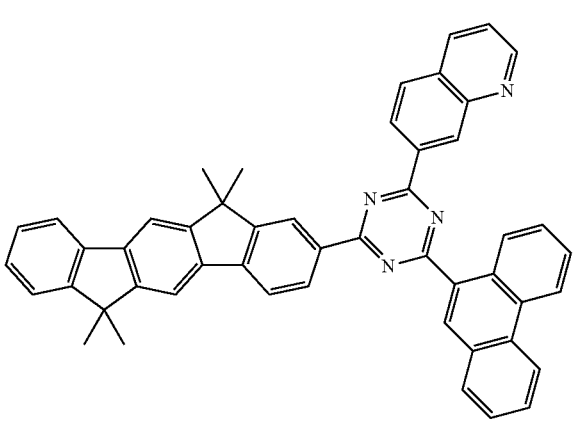
14
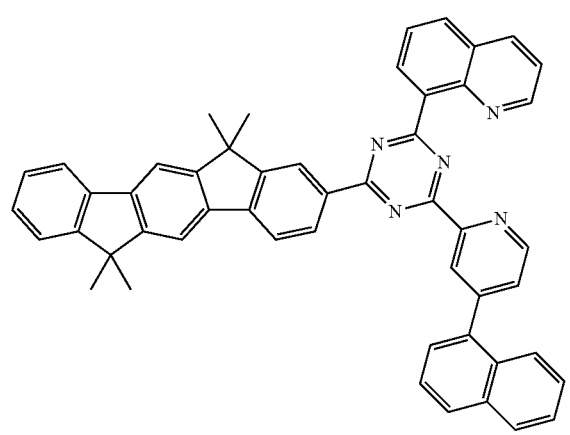
-continued
15
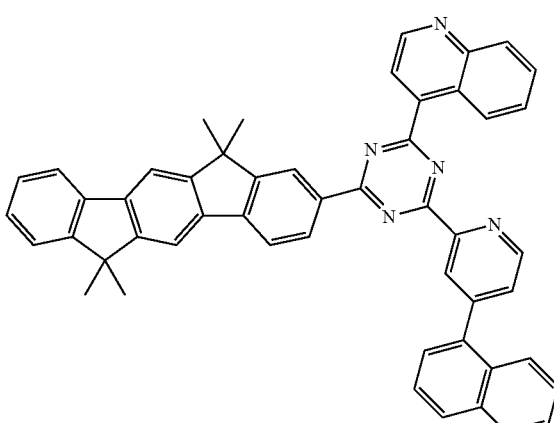
16
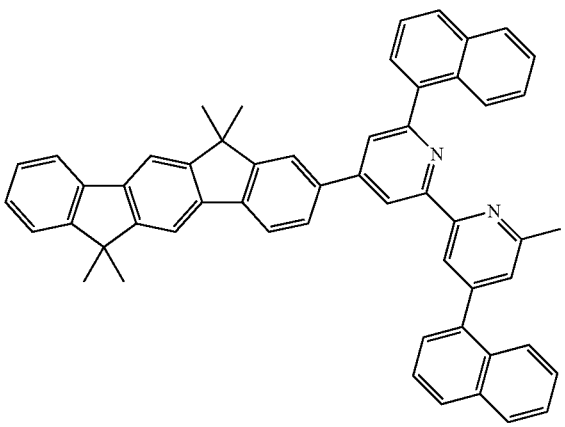
17
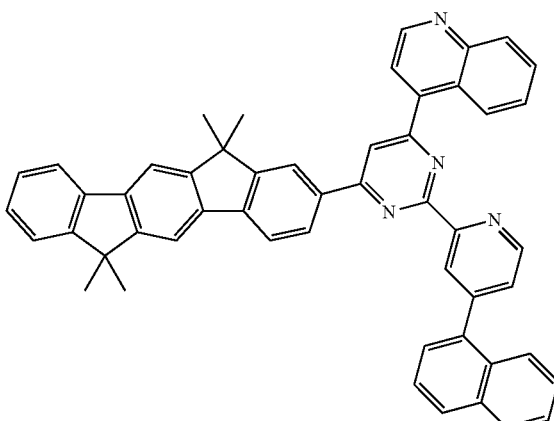

-continued

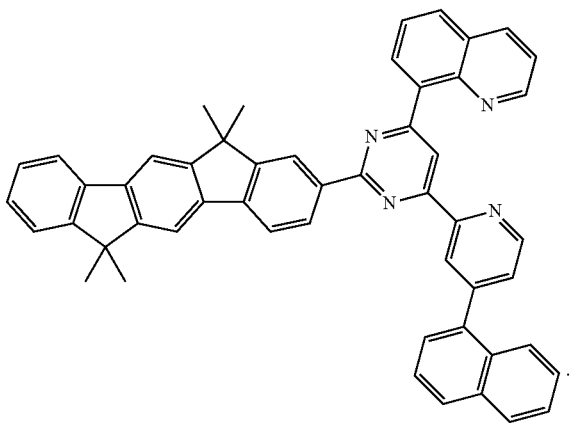

The thickness of the electron transport layer ETL may be from about 100 Å to about 1,000 Å, for example, from about 150 Å to about 500 Å. When the thickness of the electron transport layer ETL satisfies the above described range, satisfactory electron transport properties may be obtained without inducing substantial increase of a driving voltage.

When the electron transport region ETR includes the electron injection layer EIL, the electron transport region ETR may further include a metal compound, e.g., LiF, LiQ, $Li_2O$, BaO, NaCl, CsF, and Yb or a metal halide such as RbCl and RbI, without limitation. The electron injection layer EIL may be also formed using a mixture material of the electron transport material and an insulating organo metal salt. The organo metal salt may be a material having an energy band gap of more than about 4 eV. Particularly, the organo metal salt may include, for example, a metal acetate, a metal benzoate, a metal acetoacetate, a metal acetylacetonate or a metal stearate.

The thickness of the electron injection layer EIL may be from about 1 Å to about 100 Å, e.g., about 3 Å to about 90 Å. When the thickness of the electron injection layer EIL satisfies the above described range, satisfactory electron injection properties may be obtained without inducing the substantial increase of a driving voltage.

The electron transport region ETR may include a hole blocking layer, as described above. The hole blocking layer may include at least one of, for example, BCP and Bphen. The thickness of the hole blocking layer may be from about 20 Å to about 1,000 Å, e.g., from about 30 Å to about 300 Å. When the thickness of the hole blocking layer satisfies the above described range, satisfactory electron injection properties may be obtained without inducing the substantial increase of a driving voltage.

The second electrode EL2 is provided on the electron transport region ETR. The second electrode EL2 may be a common electrode or a cathode. The second electrode EL2 may be a transmissive type electrode, a transflective type electrode or a reflective type electrode.

When the second electrode EL2 is the transmissive type electrode, the second electrode EL2 may include Li, Ca, LiF/Ca, LiF/Al, Al, Mg, BaF, Ba, Ag, a compound thereof or a mixture thereof (for example, a mixture of Ag and Mg).

The second electrode EL2 may include an auxiliary electrode. The auxiliary electrode may include a layer formed by depositing the above-described material toward an emission layer EML, a transparent metal oxide on the layer, for example, ITO, IZO, ZnO, ITZO, Mo, Ti, etc.

When the second electrode EL2 is the transflective type electrode or the reflective type electrode, the second electrode EL2 may include Ag, Mg, Al, Pt, Pd, Au, Ni, Nd, Ir, Cr, Li, Ca, LiF/Ca, LiF/Al, Mo, Ti, a compound thereof or a mixture thereof (for example, a mixture of Ag and Mg). The second electrode EL2 may be a reflective layer or a transflective layer formed using the above materials and a multilayered structure including a transparent conductive layer formed using ITO, IZO, ZnO, ITZO, etc.

On the second electrode EL2, a sealing layer SL covering the second electrode EL2 is provided. The sealing layer SL may include at least one of an organic layer and an inorganic layer. The sealing layer SL passivates the organic light emitting device OEL.

The display device according to an embodiment may include an electron transport region containing a compound represented by the above Chemical Formula 1. The display device according to an embodiment may include an emission layer containing a compound represented by the above Chemical Formula 2. Thus, the band gap between the energy band of the hole transport region and the energy band of the emission layer may be decreased, and the hole injection to the emission layer may become easy in the organic light emitting device. In addition, the band gap between the energy band of the emission layer and the energy band of the electron transport region may be decreased, and the electron injection into the emission layer may become easy. Accordingly, the organic light emitting device according to an embodiment may realize high efficiency and long life.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Example 1

On a glass substrate, an anode was formed using ITO having a thickness of about 500 Å. On the anode, 2-TNATA for a hole injection layer (about 600 Å), NPB for a hole transport layer (about 300 Å), and the following compound H-1 as a host with 4 wt % of Ir(ppy)$_3$ as a dopant for an emission layer (about 400 Å) were vacuum deposited for forming organic layers. The following Compound 1 was deposited to form an electron transport layer (about 300 Å), and LiF was deposited to form an electron injection layer (about 10 Å). A cathode was formed using Al to a thickness of about 2,000 Å.

Examples 2 to 10

The same procedure was conducted as described in Example 1 except for using the compounds in the following Table 1 as the host and for forming the electron transport layer.

TABLE 1

| | Host | Electron transport layer |
|---|---|---|
| Example 1 | Compound H-1 | Compound 1 |
| Example 2 | Compound H-6 | Compound 3 |
| Example 3 | Compound H-2 | Compound 3 |
| Example 4 | Compound H-5 | Compound 7 |
| Example 5 | Compound H-3 | Compound 8 |
| Example 6 | Compound H-5 | Compound 10 |

TABLE 1-continued
| | Host | Electron transport layer |
|---|---|---|
| Example 7 | Compound H-2 | Compound 11 |
| Example 8 | Compound H-4 | Compound 11 |
| Example 9 | Compound H-6 | Compound 11 |
| Example 10 | Compound H-7 | Compound 11 |
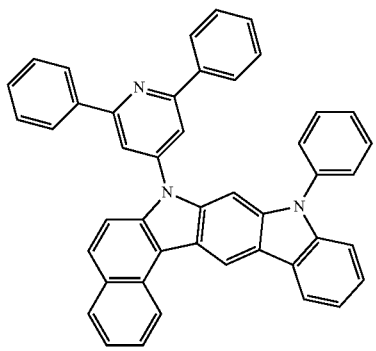
H-1
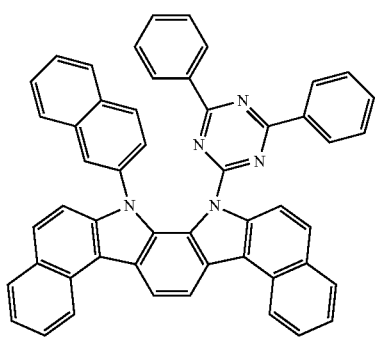
H-2
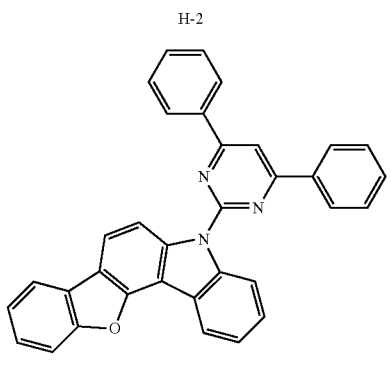
H-3
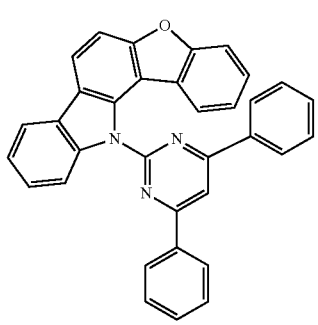
H-4
TABLE 1-continued
| | Host | Electron transport layer |
|---|---|---|
H-5
H-6
H-7
1

TABLE 1-continued

| Host | Electron transport layer |
|---|---|
| | 5 |
| 3 | |
| | 11 |
| 7 | |
| 8 | |
| 10 | |

Comparative Example 1

The same procedure was conducted as described in Example 1 except for using bis(2-methyl-8-quinolinato)(p-phenylphenolato)aluminum(III) (BAlq) as the host and depositing Alq3 as an electron transport layer.

Experimental Results

Current efficiency and life of the organic light emitting devices of Examples 1 to 10 and Comparative Example 1 were measured. The current efficiency of the organic light emitting device was measured in the conditions of the current density of 10 mA/cm$^2$.

TABLE 2

| | Efficiency (cd/A) | T90 (hr) |
|---|---|---|
| Example 1 | 54 | 71 |
| Example 2 | 57 | 70 |
| Example 3 | 61 | 68 |
| Example 4 | 58 | 77 |
| Example 5 | 67 | 73 |
| Example 6 | 53 | 69 |
| Example 7 | 69 | 76 |
| Example 8 | 66 | 81 |
| Example 9 | 58 | 68 |
| Example 10 | 63 | 73 |
| Comparative Example 1 | 42 | 47 |

Referring to the above Table 2, it may be seen that the organic light emitting devices of Examples 1 to 10 had higher efficiency and longer life than the organic light emitting device of Comparative Example 1.

The embodiments may provide an organic light emitting device having high efficiency and long life.

The embodiments may provide a display device including the organic light emitting device having high efficiency and long life.

According to the organic light emitting device according to an embodiment, efficiency may be increased, and life may be extended.

According to the display device according to an embodiment, efficiency may be increased, and life may be extended.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. An organic light emitting device, comprising:
   a first electrode;
   a hole transport region on the first electrode;
   an emission layer on the hole transport region;
   an electron transport region on the emission layer; and
   a second electrode on the electron transport region,
   wherein the electron transport region includes a compound represented by the following Chemical Formula 1:

[Chemical Formula 1]

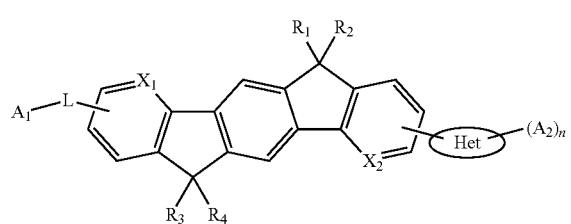

wherein, in the above Chemical Formula 1,
n is 1 or 2,
$X_1$ and $X_2$ are each independently $CR_5$ or N,
$R_1$ to $R_4$ are each independently selected from hydrogen, deuterium, an alkyl group having 1 to 40 carbon atoms, an aryl group having 6 to 40 carbon atoms, a heteroaryl group having 1 to 40 carbon atoms, an aryloxy group having 6 to 40 carbon atoms, an alkyloxy group having 1 to 40 carbon atoms, an arylamino group having 6 to 40 carbon atoms, a diarylamino group having 12 to 40 carbon atoms, an arylalkyl group having 7 to 40 carbon atoms, a cycloalkyl group having 3 to 40 carbon atoms and a heterocycloalkyl group having 3 to 40 carbon atoms, or a group forming a fused aliphatic ring, a fused aromatic ring, a fused heteroaliphatic ring or a fused heteroaromatic ring with an adjacent group, a halogen group, or a combination thereof,
$R_5$ is hydrogen,
L is selected from a direct linkage, a substituted or unsubstituted aryl group having 6 to 30 carbon atoms, a substituted or unsubstituted fused aryl group having 10 to 30 carbon atoms, a substituted or unsubstituted heteroaryl group including 1 to 30 carbon atoms and N, S or O, and a substituted or unsubstituted fused heteroarylene group having 1 to 30 carbon atoms and N, S or O,
Het is a substituted or unsubstituted heteroaryl group having 3 to 20 carbon atoms and N, and
$A_1$ is hydrogen, a substituted or unsubstituted aryl group having 6 to 40 carbon atoms, or a substituted or unsubstituted heteroaryl group having 1 to 40 carbon atoms and $A_2$ is a substituted or unsubstituted aryl group having 6 to 40 carbon atoms or a substituted or unsubstituted heteroaryl group having 1 to 40 carbon atoms, provided that $A_1$-L- is different from -Het-$A_2$.

2. The organic light emitting device as claimed in claim 1, wherein the compound represented by Chemical Formula 1 in the electron transport region includes at least one of the following Compounds 1 to 18:

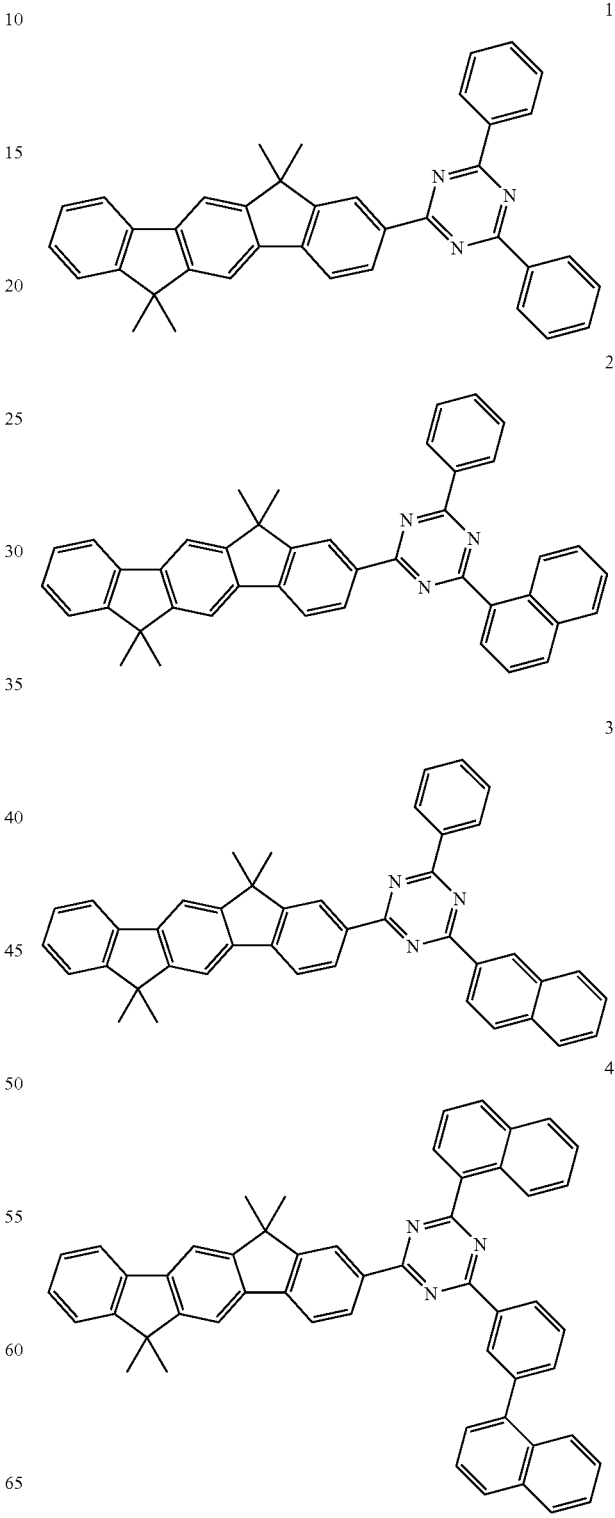

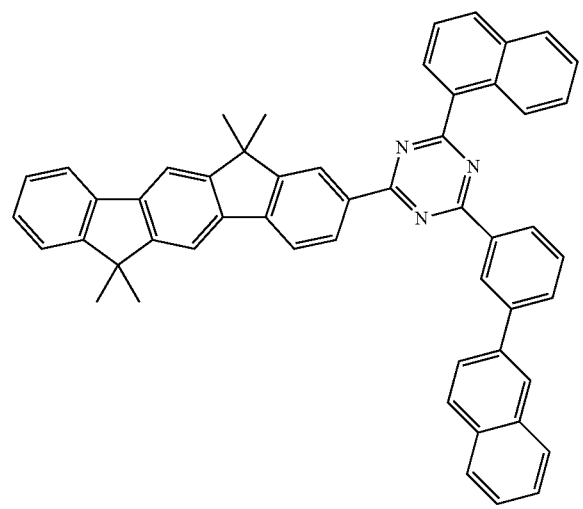
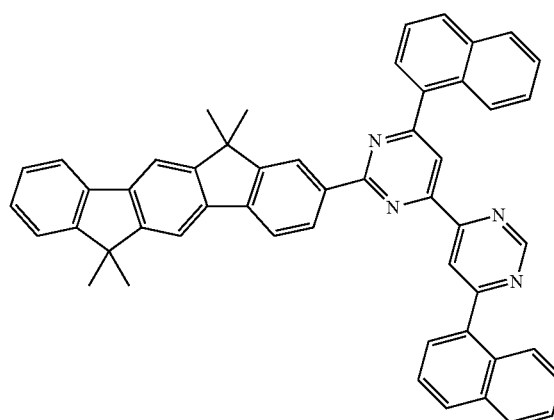
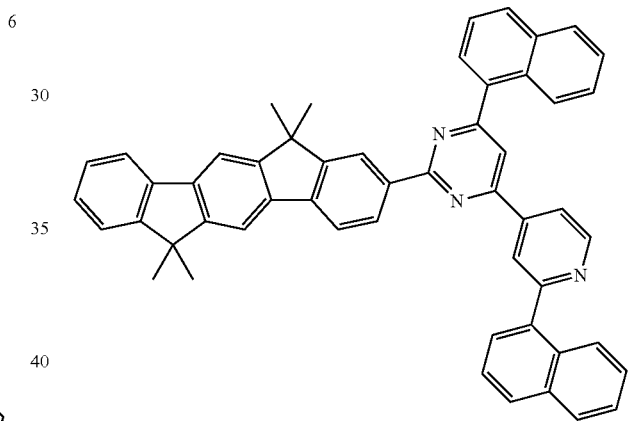
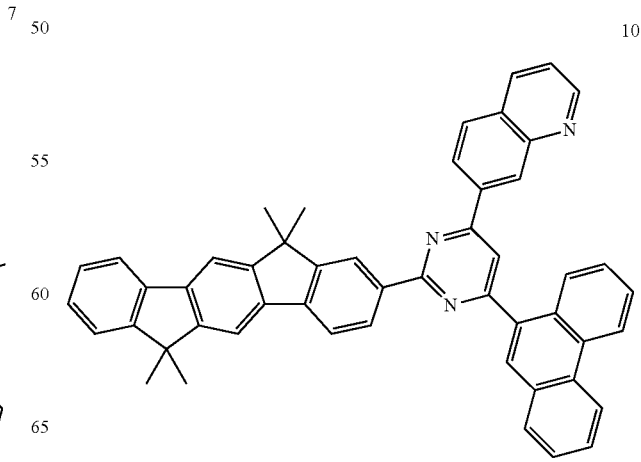

-continued
11
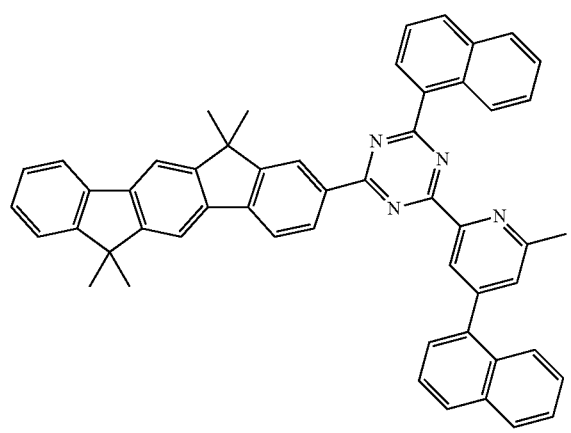
12
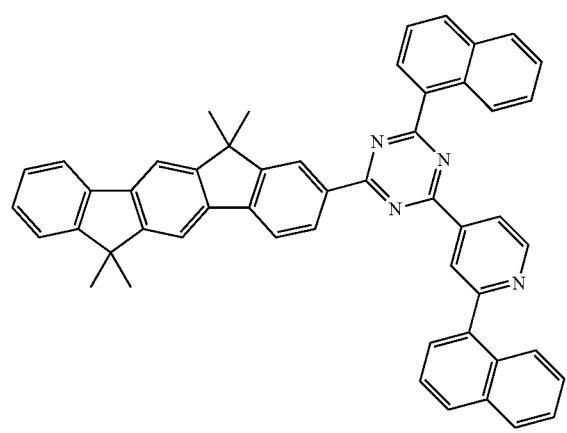
13
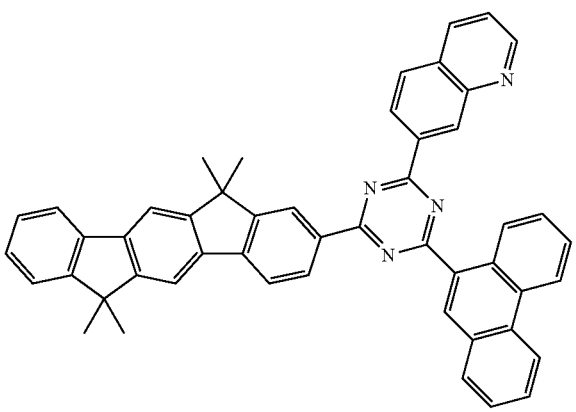
-continued
14
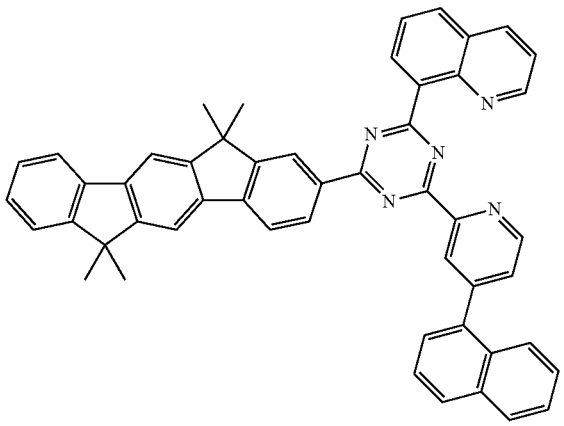
15
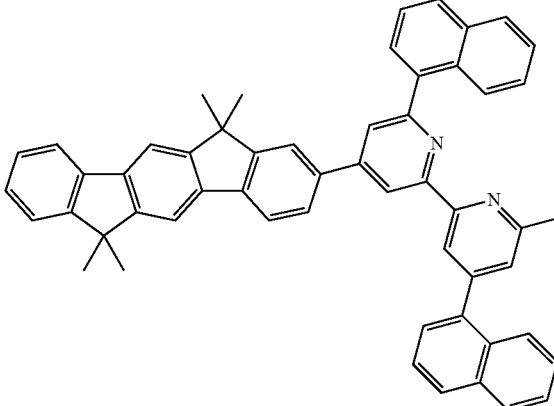
16

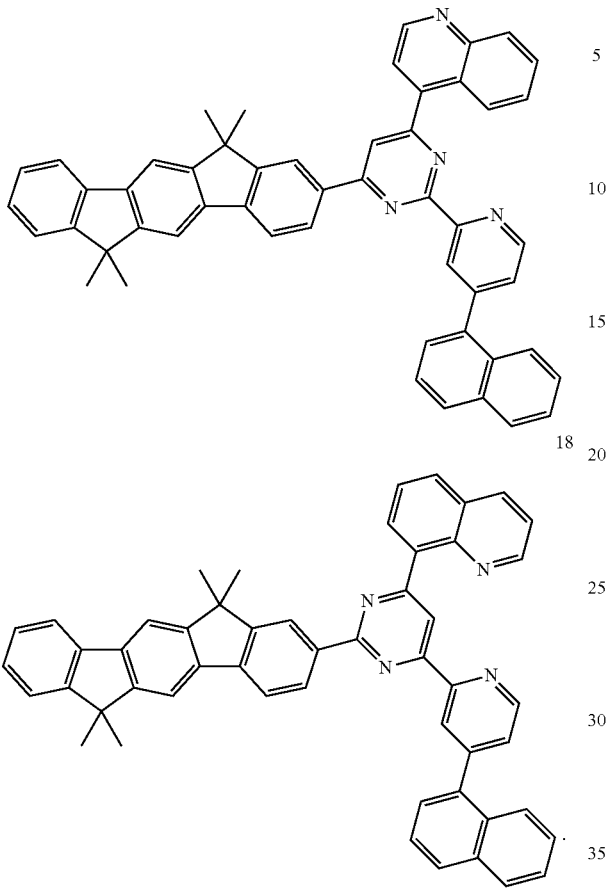

3. The organic light emitting device as claimed in claim 1, wherein the emission layer includes a compound represented by the following Chemical Formula 2:

[Chemical Formula 2]

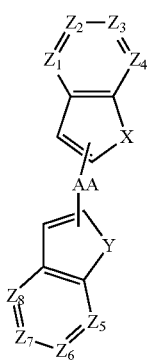

wherein, in Chemical Formula 2,

AA is selected from a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, and a heteroaryl group having 1 to 60 carbon atoms, or AA has a structure such that a ring including X and a ring including Y are fused to form a fused aliphatic ring, a fused aromatic ring, a fused heteroaliphatic ring, or a fused heteroaromatic ring, X is selected from $N(Ar_3)$, O and S, Y is selected from $N(Ar_4)$, O and S, $Ar_3$ and $Ar_4$ are each independently selected from an alkyl group having 1 to 60 carbon atoms, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms and a heteroaryl group having 1 to 60 carbon atoms, $Z_1$ to $Z_8$ are each independently selected from $C(Ar_5)$ and N, and adjacent ones of $Ar_5$ are separate or are combined to each other to form a ring, each $Ar_5$ is independently selected from hydrogen, an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, a heteroaryl group having 1 to 60 carbon atoms, an arylthio group having 6 to 60 carbon atoms, an alkylthio group having 1 to 60 carbon atoms, a mono- or di-alkylamino group having 1 to 60 carbon atoms, a monoarylamino group having 6 to 30 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group and a hydroxyl group, and the compound represented by Chemical Formula 2 does not include a compound in which X is $N(Ar_3)$, Y is $N(Ar_4)$, both $Ar_3$ and $Ar_4$ are the same, all $Z_1$ to $Z_8$ are $C(Ar_5)$, and $Ar_5$ included in each of $Z_1$ to $Z_8$ are the same.

4. The organic light emitting device as claimed in claim 3, wherein the alkyl group, the cycloalkyl group, the heterocycloalkyl group, the bicycloalkyl group, the adamantyl group, the alkenyl group, the alkynyl group, the aryl group, the alkoxy group, the aryloxy group, the heteroaryl group, the arylthio group, the alkylthio group, the alkylamino group, the arylamino group, the trialkylsilyl group, the dialkylarylsilyl group, the triarylsilyl group, the arylboranyl group, or the alkylboranyl group in $Ar_3$ to $Ar_5$ is substituted with at least one substituent selected from an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, an aryl group having 6 to 60 carbon atoms and substituted with $P(=O)RaRb$, in which Ra and Rb are independently an alkyl group having 1 to 60 carbon atoms or an aryl group having 6 to 60 carbon atoms, a heteroaryl group having 1 to 60 carbon atoms, a heteroaryl group having 1 to 60 carbon atoms and substituted with an aryl group having 6 to 60 carbon atoms, a heteroaryl group having 1 to 60 carbon atoms and substituted with an alkyl group having 1 to 60 carbon atoms, an aralkyl group having 7 to 120 carbon atoms, an arylthio group having 6 to 60 carbon atoms, an alkylthio group having 1 to 60 carbon atoms, a mono- or di-alkylamino group having 1 to 30 carbon atoms, a mono- or di-arylamino group having 6 to 60 carbon atoms, a trialkylsilyl group having 3 to 90 carbon atoms. a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group and a hydroxyl group.

5. The organic light emitting device as claimed in claim 4, wherein the emission layer includes at least one of the following compounds, in which X, Y, and $Z_1$ to $Z_8$ are defined the same as X, Y, and $Z_1$ to $Z_8$ of Chemical Formula 2:

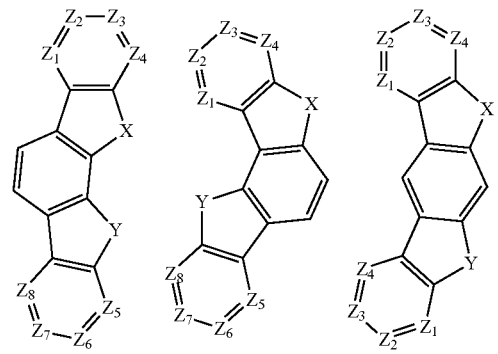

6. The organic light emitting device as claimed in claim 1, wherein the emission layer includes at least one of the following Compounds H-1 to H-7:

H-1

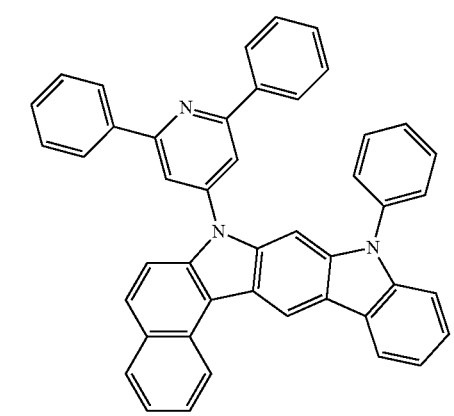

H-2

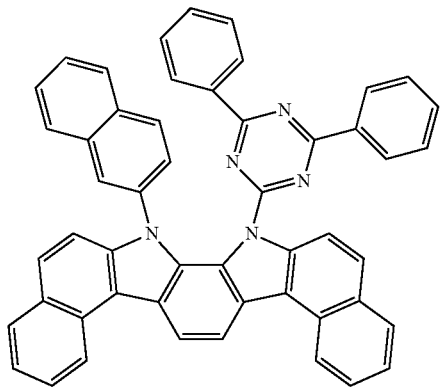

H-3

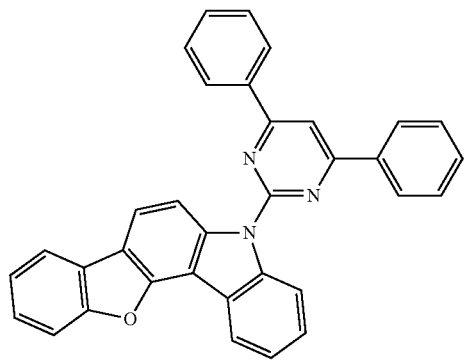

H-4

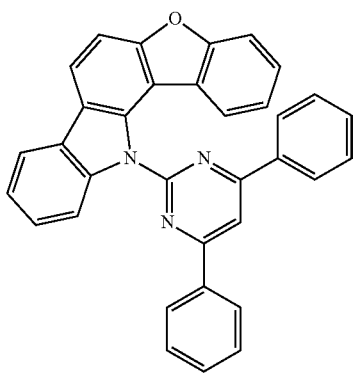

H-5

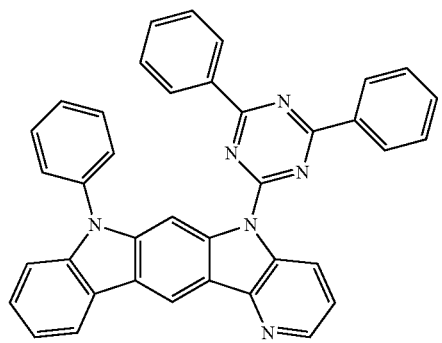

97
-continued
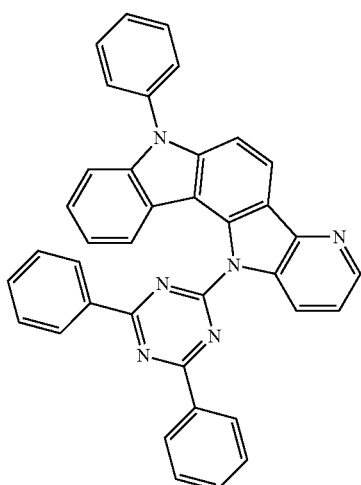
H-6
98
-continued
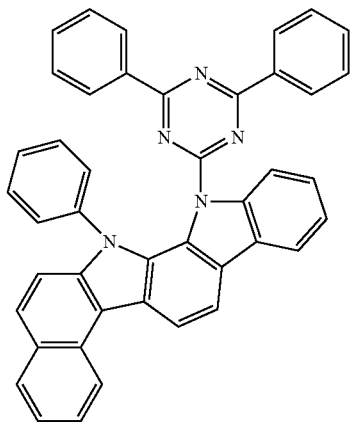
H-7
7. The organic light emitting device as claimed in claim 3, wherein the emission layer further includes an arylamine-containing compound.
8. The organic light emitting device as claimed in claim 7, wherein the arylamine-containing compound is one of the following compounds:
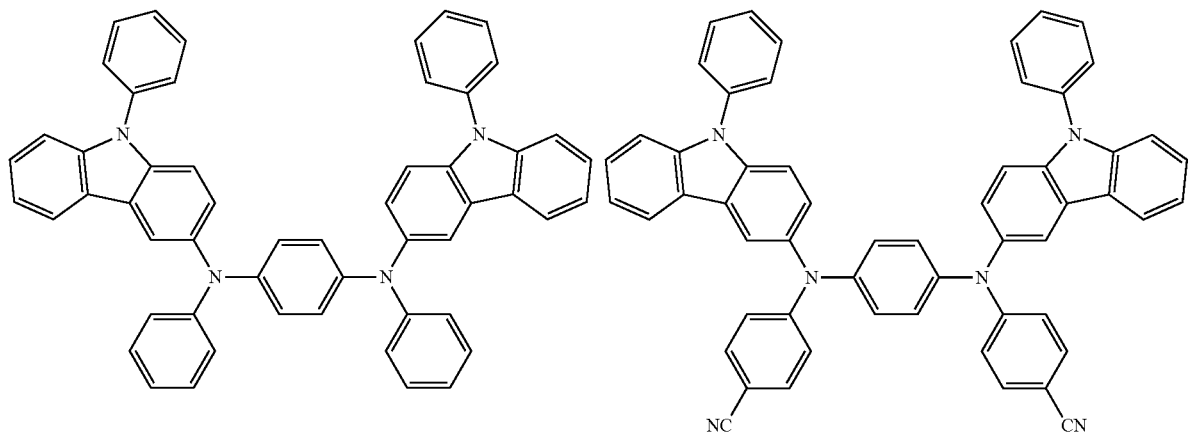
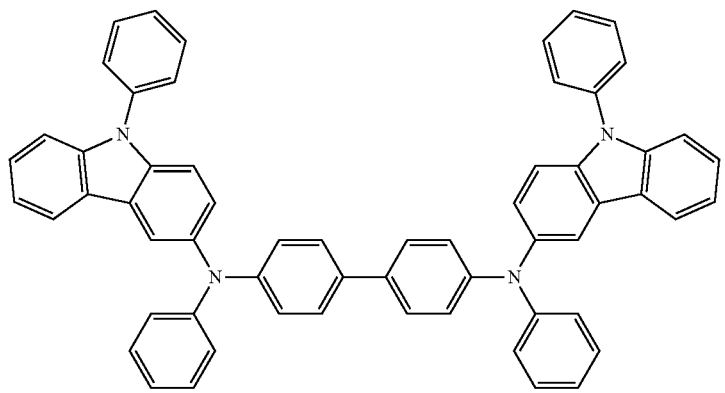

-continued
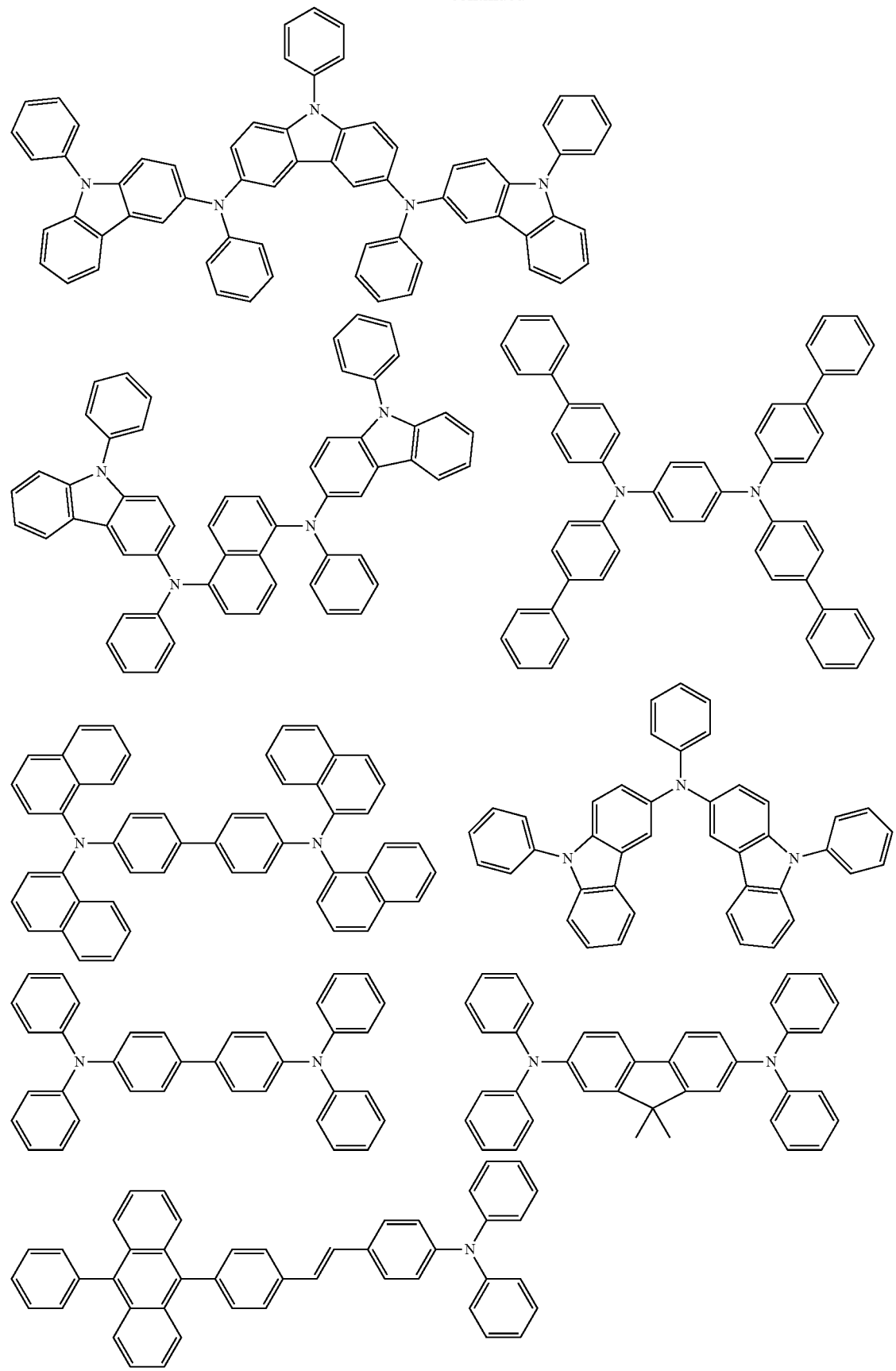

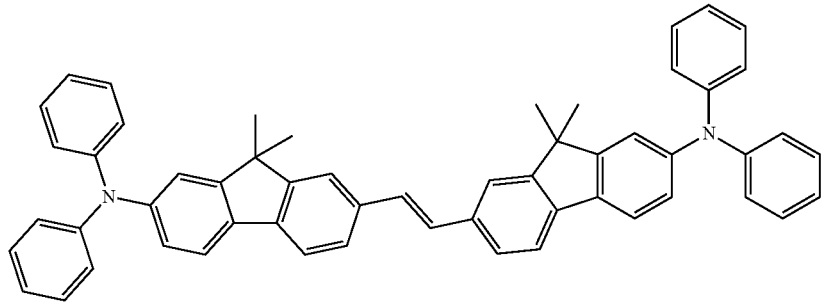
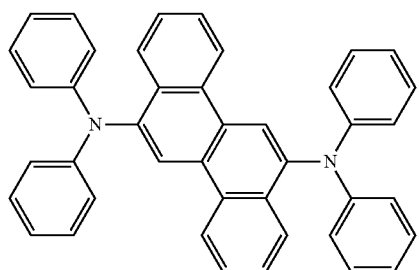
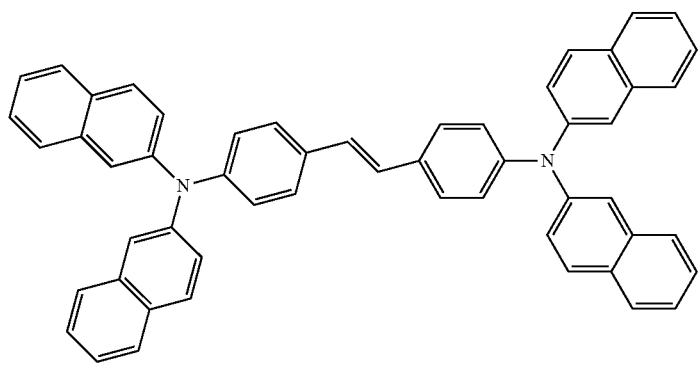
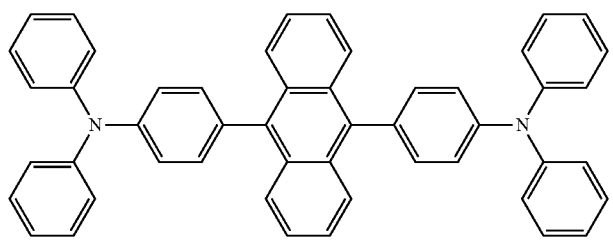
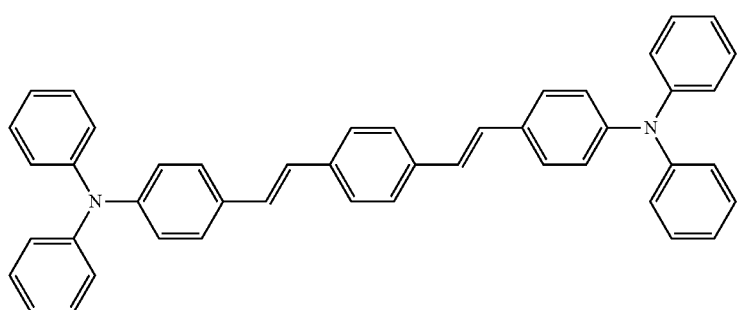

-continued

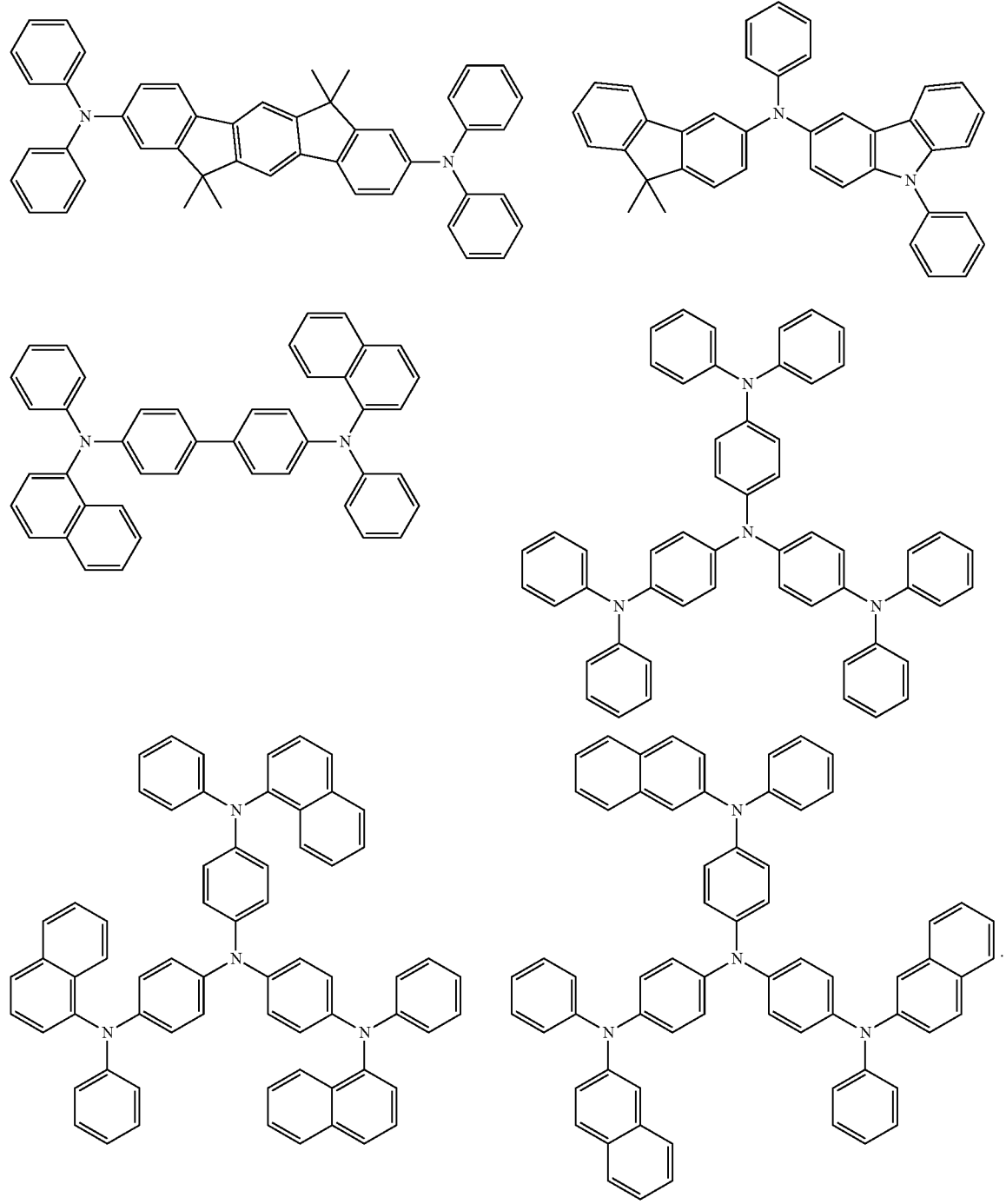

9. The organic light emitting device as claimed in claim 1, wherein the emission layer emits green light.

10. A display device comprising a plurality of pixels, at least one of the pixels including:
 a hole transport region on a first electrode;
 an emission layer on the hole transport region;
 an electron transport region on the emission layer; and
 a second electrode on the electron transport region,
 wherein the electron transport region includes a compound represented by the following Chemical Formula 1:

[Chemical Formula 1]

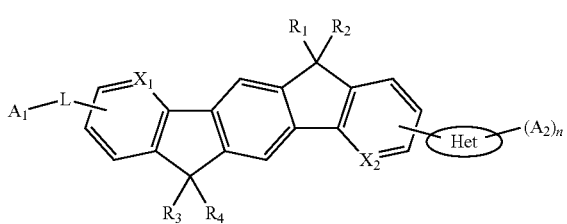

wherein, in Chemical Formula 1, n is 1 or 2, $X_1$ and $X_2$ are each independently $CR_5$ or N, $R_1$ to $R_4$ are each independently selected from hydrogen, deuterium, an alkyl group having 1 to 40 carbon atoms, an aryl group having 6 to 40 carbon atoms, a heteroaryl group having 1 to 40 carbon atoms, an aryloxy group having 6 to 40 carbon atoms, an alkyloxy group having 1 to 40 carbon atoms, an arylamino group having 6 to 40 carbon atoms, a diarylamino group having 12 to 40 carbon atoms, an arylalkyl group having 7 to 40 carbon atoms, a cycloalkyl group having 3 to 40 carbon atoms and a heterocycloalkyl group having 3 to 40 carbon atoms, or a group forming a fused aliphatic ring, a fused aromatic ring, a fused heteroaliphatic ring or a fused heteroaromatic ring with an adjacent group, a halogen group, or a combination thereof, $R_5$ is hydrogen., L is selected from a direct linkage, a substituted or unsubstituted aryl group having 6 to 30 carbon atoms, a substituted or unsubstituted fused aryl group having 10 to 30 carbon atoms, a substituted or unsubstituted heteroaryl group including 1 to 30 carbon atoms and N, S or O, and a substituted or unsubstituted fused heteroarylene group having 1 to 30 carbon atoms and N, S or O, Het is a substituted or unsubstituted heteroaryl group having 3 to 20 carbon atoms and N, and $A_1$ is hydrogen, a substituted or unsubstituted aryl group having 6 to 40 carbon atoms, or a substituted or unsubstituted heteroaryl group having 1 to 40 carbon atoms and $A_2$ is a substituted or unsubstituted aryl group having 6 to 40 carbon atoms or a substituted or unsubstituted heteroaryl group having 1 to 40 carbon atoms, provided that $A_1$-L- is different from -Het-$A_2$.

11. The display device as claimed in claim 10, wherein the compound represented by Chemical Formula 1 in the electron transport region includes at least one of the following Compounds 1 to 18:

1

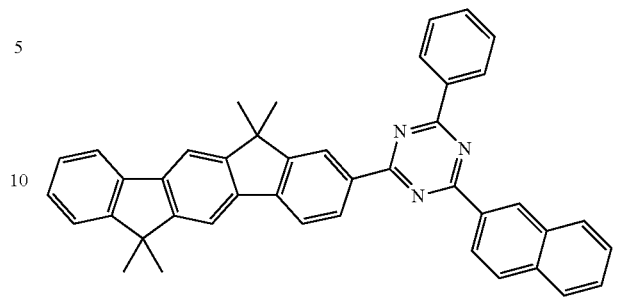

2

3

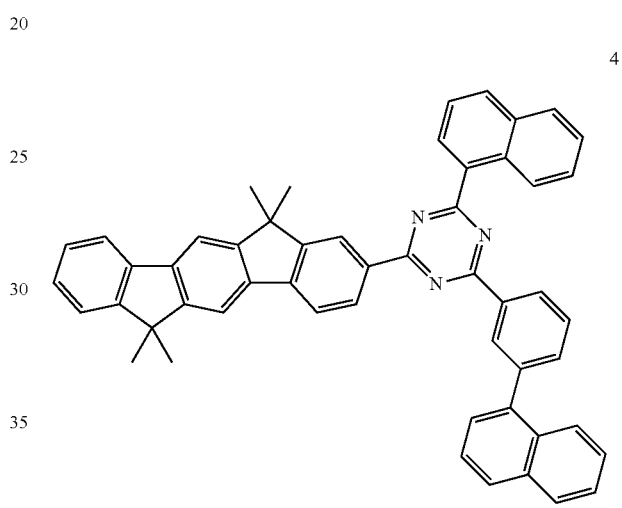

4

5

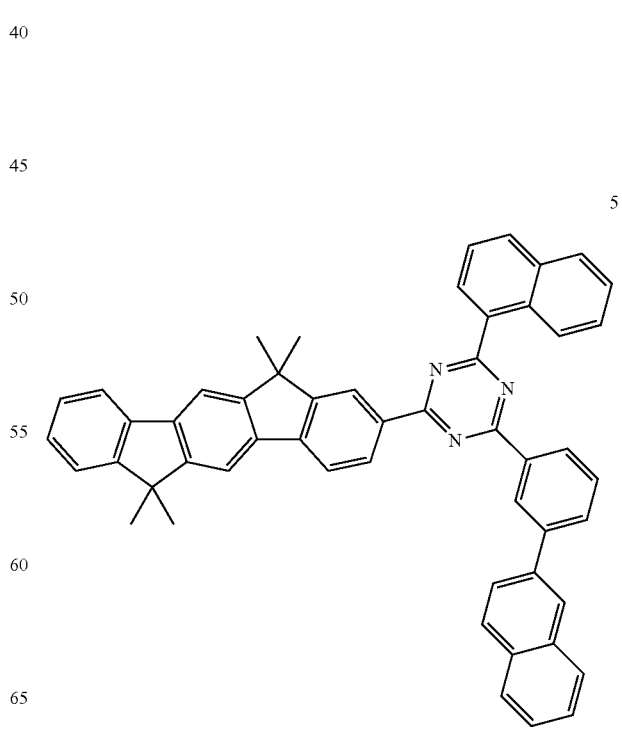

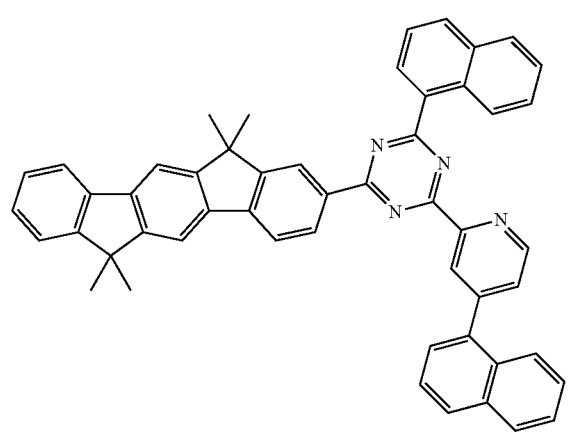
6
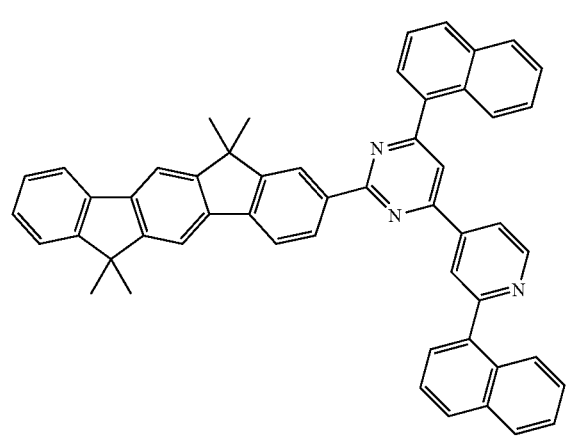
9
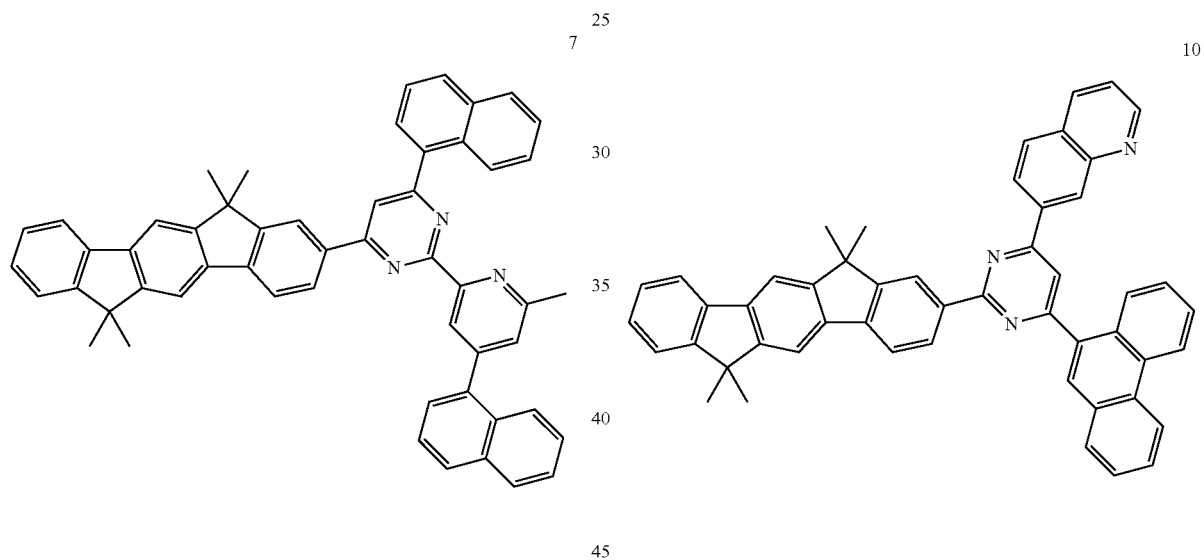
7
10
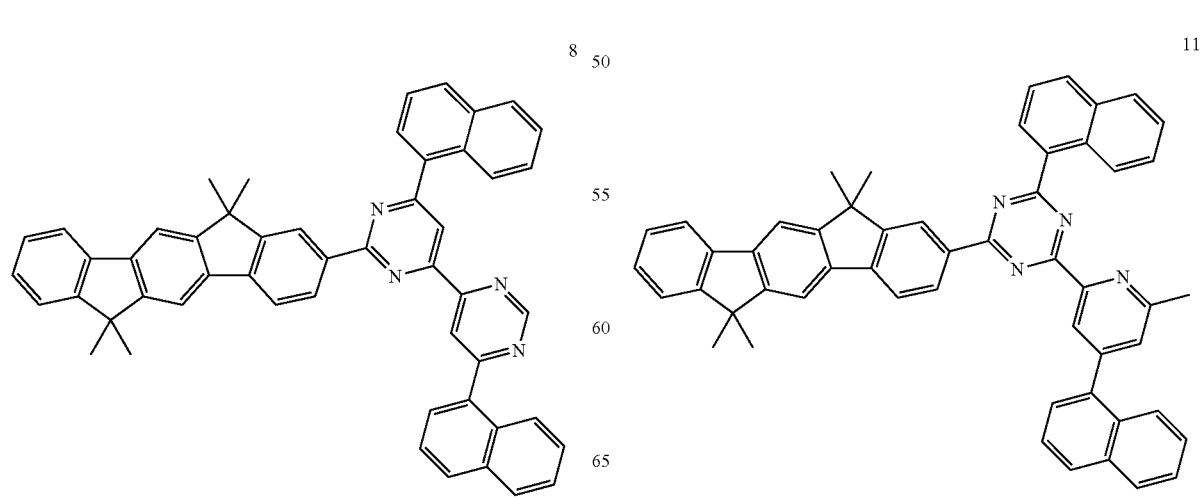
8
11

12
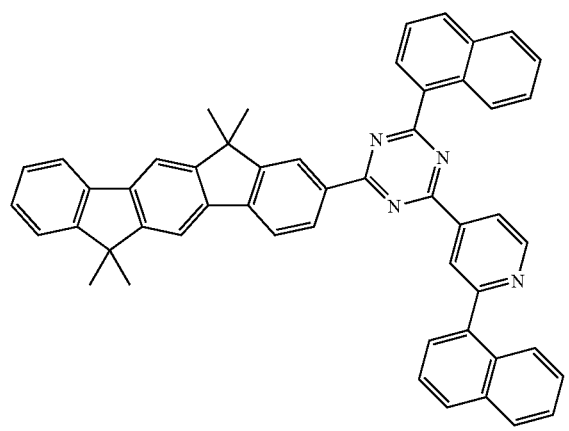
13
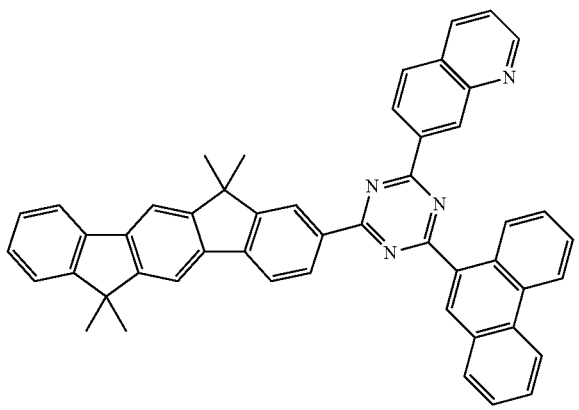
14
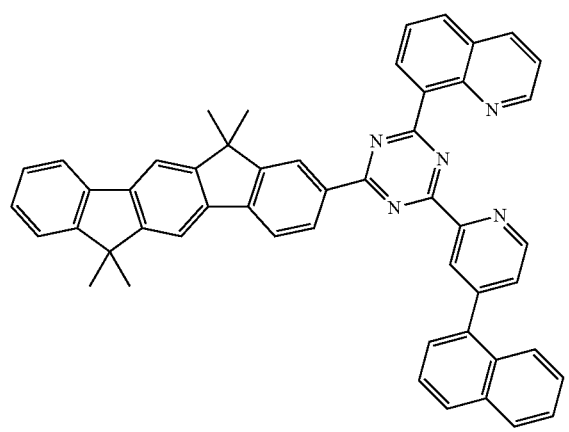
15
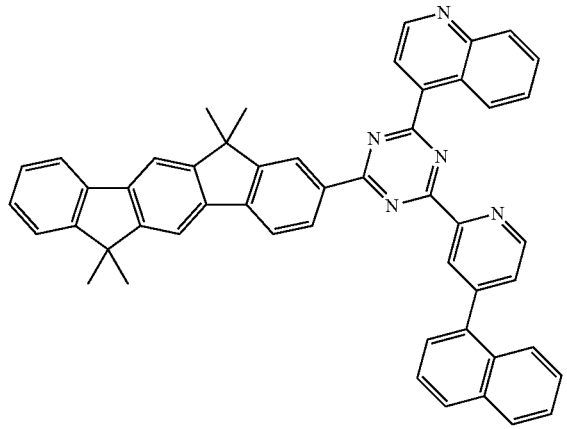
16
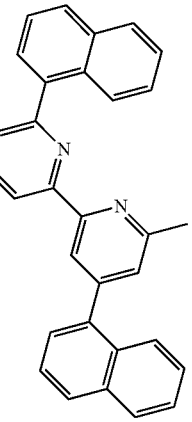
17
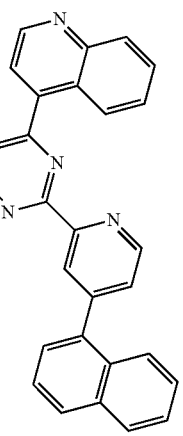

-continued

18

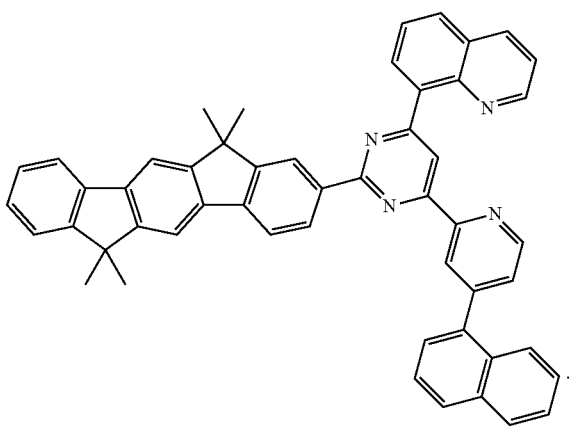

12. The display device as claimed in claim 10, wherein the emission layer includes a compound represented by the following Chemical Formula 2:

[Chemical Formula 2]

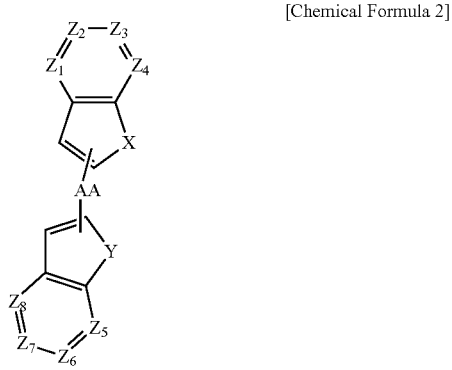

wherein, in Chemical Formula 2,
AA is selected from a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, and a heteroaryl group having 1 to 60 carbon atoms, or AA has a structure such that a ring including X and a ring including Y are fused to form a fused aliphatic ring, a fused aromatic ring, a fused heteroaliphatic ring, or a fused heteroaromatic ring,
X is selected from $N(Ar_3)$, O and S,
Y is selected from $N(Ar_4)$, O and S,
$Ar_3$ and $Ar_4$ are each independently selected from an alkyl group having 1 to 60 carbon atoms, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms and a heteroaryl group having 1 to 60 carbon atoms,
$Z_1$ to $Z_8$ are each independently selected from $C(Ar_5)$, and adjacent ones of $Ar_5$ are separate or are combined to each other to form a ring,
each $Ar_5$ is independently selected from hydrogen, an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, a heteroaryl group having 1 to 60 carbon atoms, an arylthio group having 6 to 60 carbon atoms, an alkylthio group having 1 to 60 carbon atoms, a mono- or di-alkylamino group having 1 to 60 carbon atoms, a monoarylamino group having 6 to 30 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group and a hydroxyl group, and
the compound represented by Chemical Formula 2 does not include a compound in which X is $N(Ar_3)$, Y is $N(Ar_4)$, both $Ar_3$ and $Ar_4$ are the same, all $Z_1$ to $Z_8$ are $C(Ar_5)$, and $Ar_5$ included in each of $Z_1$ to $Z_8$ are the same.

13. The display device as claimed in claim 12, wherein the alkyl group, the cycloalkyl group, the heterocycloalkyl group, the bicycloalkyl group, the adamantyl group, the alkenyl group, the alkynyl group, the aryl group, the alkoxy group, the aryloxy group, the heteroaryl group, the arylthio group, the alkylthio group, the alkylamino group, the arylamino group, the trialkylsilyl group, the dialkylarylsilyl group, the triarylsilyl group, the arylboranyl group, or the alkylboranyl group in $Ar_3$ to $Ar_5$ is substituted with at least one substituent selected from an alkyl group having 1 to 60 carbon atoms, a halogen group, a cyano group, a cycloalkyl group having 3 to 60 carbon atoms, a five-membered or six-membered heterocycloalkyl group including at least one selected from N, O, S, Si and P, a bicycloalkyl group having 7 to 60 carbon atoms, an adamantyl group, an alkenyl group having 2 to 60 carbon atoms, an alkynyl group having 2 to 60 carbon atoms, an aryl group having 6 to 60 carbon atoms, an alkoxy group having 1 to 60 carbon atoms, an aryloxy group having 6 to 60 carbon atoms, an aryl group having 6 to 60 carbon atoms and substituted with P(=O)RaRb, in which Ra and Rb are independently an alkyl group having 1 to 60 carbon atoms or an aryl group having 6 to 60 carbon atoms, a heteroaryl group having 1 to 60 carbon atoms, a heteroaryl group having 1 to 60 carbon atoms and substituted with an aryl group having 6 to 60 carbon atoms, a heteroaryl group having 1 to 60 carbon atoms and substituted with an alkyl group having 1 to 60 carbon atoms, an aralkyl group having 7 to 120 carbon atoms, an arylthio group having 6 to 60 carbon atoms, an alkylthio group having 1 to 60 carbon atoms, a mono- or di-alkylamino group having 1 to 30 carbon atoms, a mono- or di-arylamino group having 6 to 60 carbon atoms, a trialkylsilyl group having 3 to 90 carbon atoms, a dialkylarylsilyl group having 7 to 60 carbon atoms, a triarylsilyl group having 18 to 90 carbon atoms, a mono- or di-arylboranyl group having 6 to 60 carbon atoms, a mono- or di-alkylboranyl group having 1 to 120 carbon atoms, a nitro group and a hydroxyl group.

14. The display device as claimed in claim 12, wherein the emission layer includes at least one of the following compounds, in which X, Y, and $Z_1$ to $Z_8$ are defined the same as X, Y, and $Z_1$ to $Z_8$ of Chemical Formula 2:

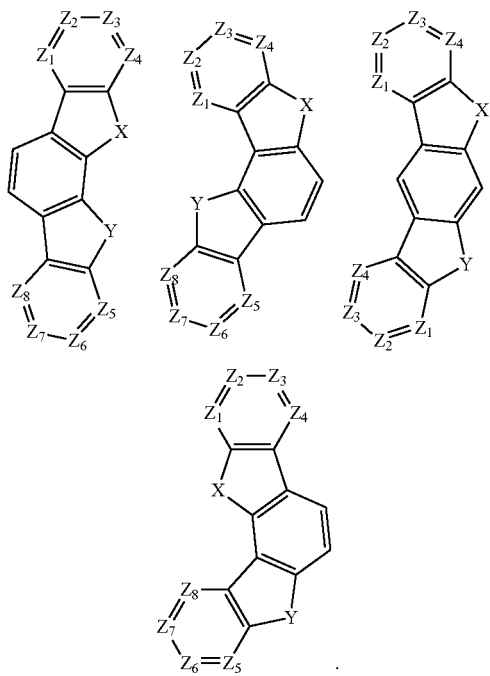

15. The display device as claimed in claim 10, wherein the emission layer includes at least one of the following Compounds H-1 to H-7:

H-1
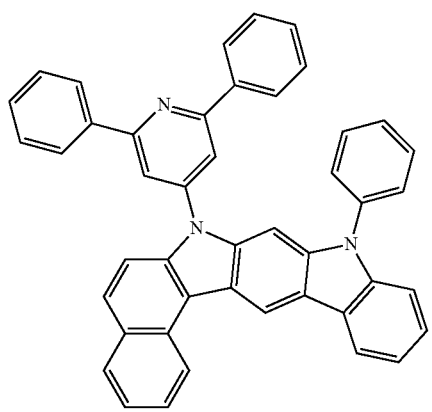

H-2
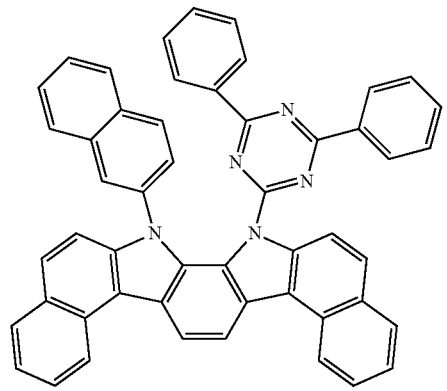

H-3
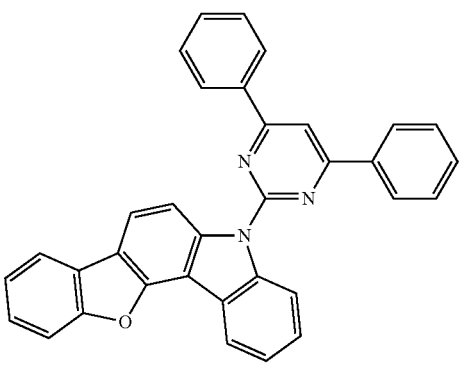

H-4
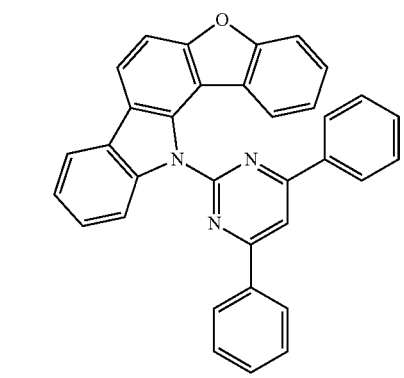

H-5
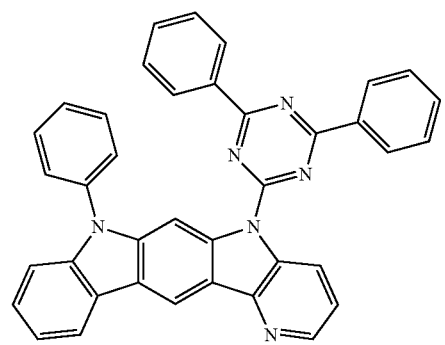

115
-continued
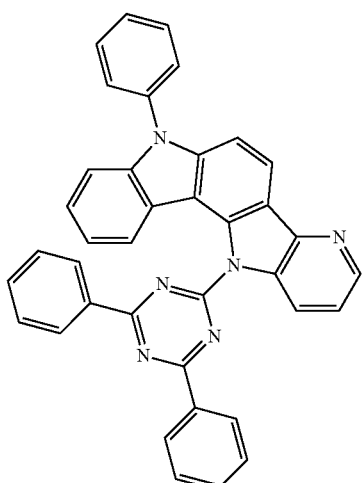
H-6
116
-continued
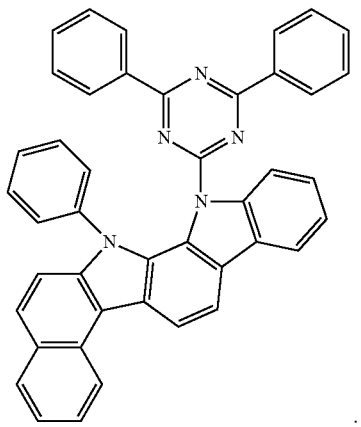
H-7
16. The display device as claimed in claim 12, wherein the emission layer further includes an arylamine-containing compound.
17. The display device as claimed in claim 16, wherein the arylamine-containing compound is one of the following compounds:
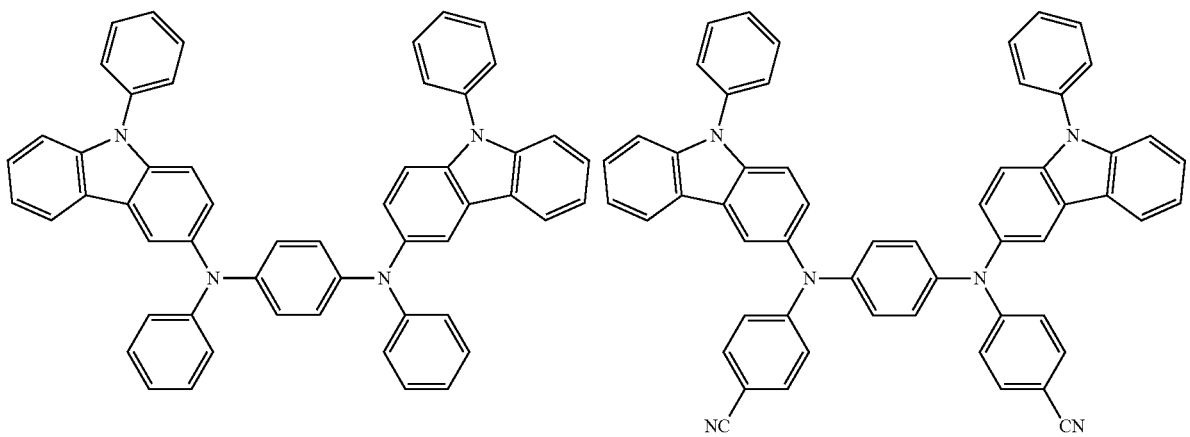
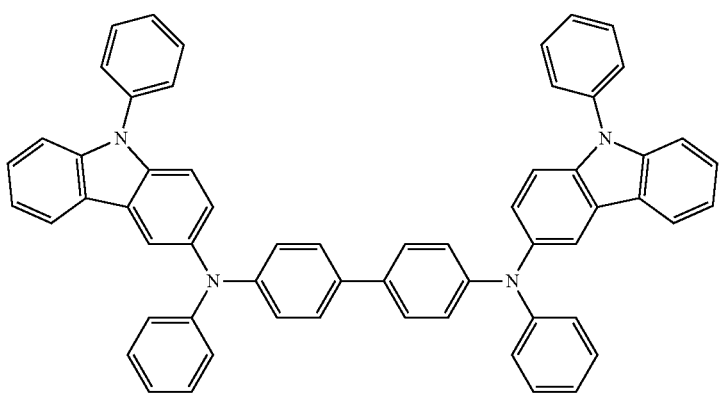

-continued
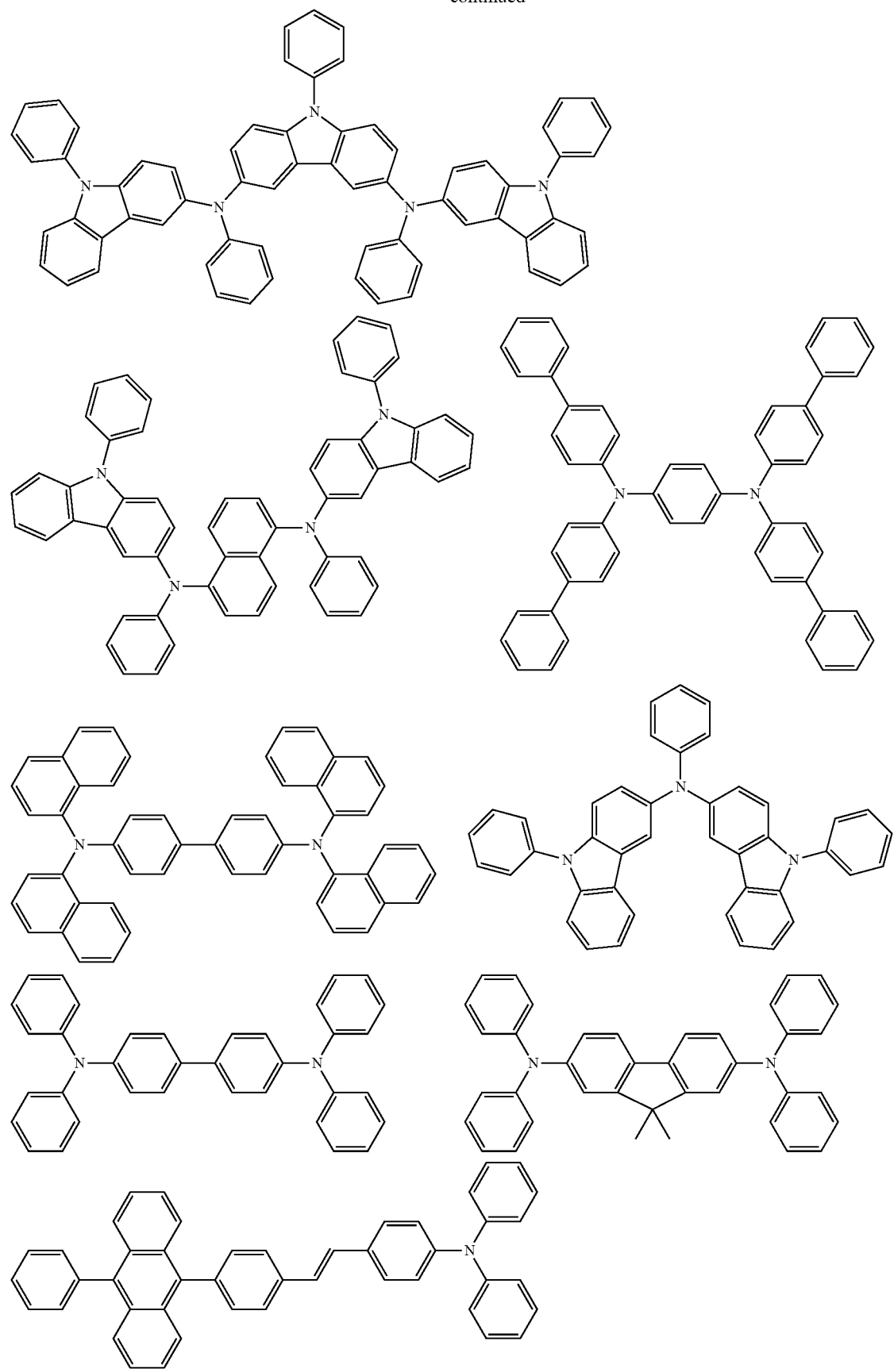

-continued
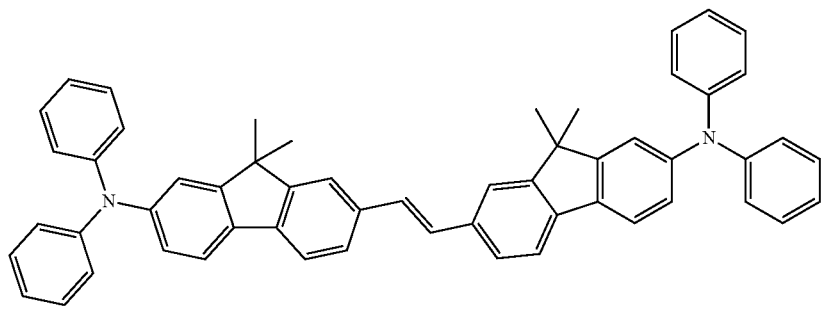

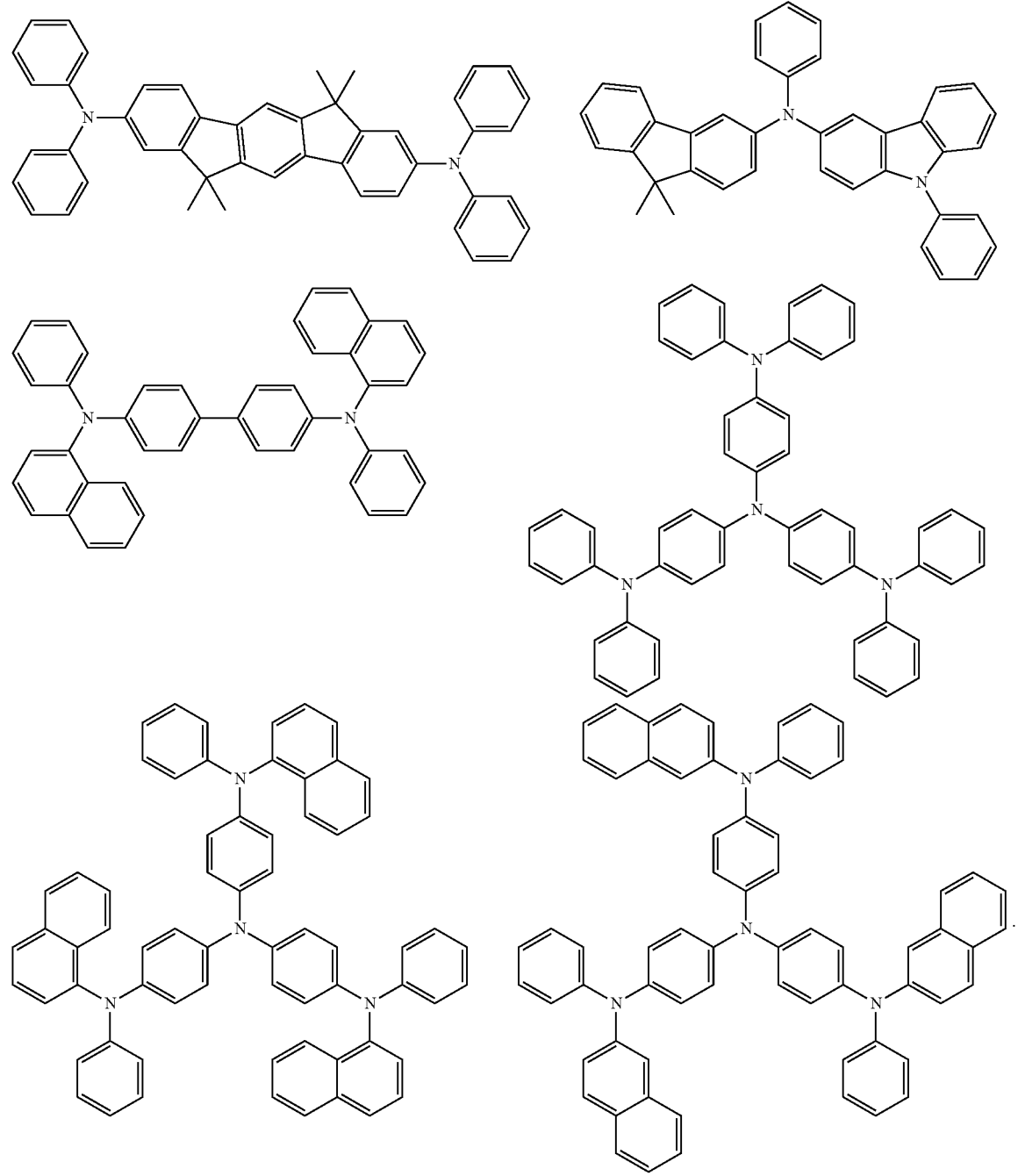
18. The display device as claimed in claim 10, wherein the emission layer emits green light.
* * * * *